US012233003B2

(12) United States Patent
Newton

(10) Patent No.: US 12,233,003 B2
(45) Date of Patent: Feb. 25, 2025

(54) FLUID COLLECTION ASSEMBLIES INCLUDING AT LEAST ONE LENGTH ADJUSTING FEATURE

(71) Applicant: PureWick Corporation, El Cajon, CA (US)

(72) Inventor: Camille Rose Newton, Bonsall, CA (US)

(73) Assignee: PureWick Corporation, Covington, GA (US)

( * ) Notice: Subject to any disclaimer, the term of this patent is extended or adjusted under 35 U.S.C. 154(b) by 8 days.

(21) Appl. No.: 17/661,090

(22) Filed: Apr. 28, 2022

(65) Prior Publication Data

US 2022/0347004 A1 Nov. 3, 2022

Related U.S. Application Data

(60) Provisional application No. 63/181,709, filed on Apr. 29, 2021.

(51) Int. Cl.
  *A61F 5/453* (2006.01)
  *A61F 5/44* (2006.01)
  *A61M 1/00* (2006.01)

(52) U.S. Cl.
  CPC ............ *A61F 5/453* (2013.01); *A61F 5/4404* (2013.01); *A61M 1/80* (2021.05)

(58) Field of Classification Search
  CPC .... A61F 5/453; A61F 5/4404; A61M 2210/16
  See application file for complete search history.

(56) References Cited

U.S. PATENT DOCUMENTS

| 737,443 A | 8/1903 | Mooers |
| 1,032,841 A | 7/1912 | Koenig |
| (Continued) | | |

FOREIGN PATENT DOCUMENTS

| AU | 2018216821 A1 | 8/2019 |
| AU | 2021299304 A1 | 2/2023 |
| (Continued) | | |

OTHER PUBLICATIONS

US 9,908,683 B2, 03/2018, Sandhausen et al. (withdrawn)
(Continued)

*Primary Examiner* — Rebecca E Eisenberg
*Assistant Examiner* — Matthew Wrubleski
(74) *Attorney, Agent, or Firm* — Dorsey & Whitney LLP

(57) ABSTRACT

Embodiments are directed towards fluid collection assemblies that include at least one length adjusting feature, fluid collection assemblies including the same, and methods of using the same. An example fluid collection assembly includes a fluid impermeable barrier. The fluid impermeable barrier includes a distal region, at least one distal end region spaced from the distal region, and at least one intermediate portion extending from the distal region to the distal region. The fluid impermeable barrier also defines at least one length adjusting feature ("LAF") extending from the distal end region to the distal region. The LAF allows the length of the fluid collection assembly to change. The ability of the fluid collection assembly to change the length thereof allows a penis of a patient to be disposed in preferential locations within the fluid collection assembly.

22 Claims, 10 Drawing Sheets

(56) References Cited

U.S. PATENT DOCUMENTS

| | | |
|---|---|---|
| 1,178,644 A | 4/1916 | Johnson |
| 1,387,726 A | 8/1921 | Karge |
| 1,742,080 A | 12/1929 | Jones |
| 1,979,899 A | 11/1934 | Obrien et al. |
| 2,241,010 A | 5/1941 | Chipley |
| 2,262,772 A | 11/1941 | Peder |
| 2,326,881 A | 8/1943 | Packer |
| 2,379,346 A | 6/1945 | Farrell |
| 2,485,555 A | 10/1949 | Bester |
| 2,571,357 A | 10/1951 | Charles |
| 2,613,670 A | 10/1952 | Edward |
| 2,616,426 A | 11/1952 | Adele |
| 2,644,234 A | 7/1953 | Earl |
| 2,648,335 A | 8/1953 | Chambers |
| 2,859,786 A | 11/1958 | Tupper |
| 2,944,551 A | 7/1960 | Carl |
| 2,968,046 A | 1/1961 | Duke |
| 2,971,512 A | 2/1961 | Reinhardt |
| 3,032,038 A | 5/1962 | Swinn |
| 3,077,883 A | 2/1963 | Hill |
| 3,087,938 A | 4/1963 | Hans et al. |
| 3,169,528 A | 2/1965 | Knox et al. |
| 3,171,506 A | 3/1965 | Therkel |
| 3,194,238 A | 7/1965 | Breece |
| 3,198,994 A | 8/1965 | Hildebrandt et al. |
| 3,221,742 A | 12/1965 | Egon |
| 3,312,221 A | 4/1967 | Overment |
| 3,312,981 A | 4/1967 | McGuire et al. |
| 3,349,768 A | 10/1967 | Keane |
| 3,362,590 A | 1/1968 | Gene |
| 3,366,116 A | 1/1968 | Huck |
| 3,398,848 A | 8/1968 | Donovan |
| 3,400,717 A | 9/1968 | Bruce et al. |
| 3,406,688 A | 10/1968 | Bruce |
| 3,424,163 A | 1/1969 | Gravdahl |
| 3,425,471 A | 2/1969 | Yates |
| 3,511,241 A | 5/1970 | Lee |
| 3,512,185 A | 5/1970 | Ellis |
| 3,520,300 A | 7/1970 | Flower |
| 3,528,423 A | 9/1970 | Lee |
| 3,613,123 A | 10/1971 | Langstrom |
| 3,648,700 A | 3/1972 | Warner |
| 3,651,810 A | 3/1972 | Ormerod |
| 3,661,155 A | 5/1972 | Lindan |
| 3,683,918 A | 8/1972 | Pizzella |
| 3,699,815 A | 10/1972 | Holbrook |
| 3,726,277 A | 4/1973 | Hirschman |
| 3,742,952 A | 7/1973 | Magers et al. |
| 3,757,355 A | 9/1973 | Allen et al. |
| 3,788,324 A * | 1/1974 | Lim .................. A61F 5/453 |
| | | 604/352 |
| 3,843,016 A | 10/1974 | Bornhorst et al. |
| 3,863,638 A | 2/1975 | Rogers et al. |
| 3,863,798 A | 2/1975 | Kurihara et al. |
| 3,864,759 A | 2/1975 | Horiuchi |
| 3,865,109 A | 2/1975 | Elmore et al. |
| 3,881,486 A | 5/1975 | Fenton |
| 3,881,489 A | 5/1975 | Hartwell |
| 3,915,189 A | 10/1975 | Holbrook et al. |
| 3,998,228 A | 12/1976 | Poidomani |
| 3,999,550 A | 12/1976 | Martin |
| 4,015,604 A | 4/1977 | Csillag |
| 4,020,843 A | 5/1977 | Kanall |
| 4,022,213 A | 5/1977 | Stein |
| 4,027,776 A | 6/1977 | Douglas |
| 4,064,962 A | 12/1977 | Hunt |
| 4,116,197 A | 9/1978 | Bermingham |
| 4,180,178 A | 12/1979 | Turner |
| 4,187,953 A | 2/1980 | Turner |
| 4,194,508 A | 3/1980 | Anderson |
| 4,200,102 A | 4/1980 | Duhamel et al. |
| 4,202,058 A | 5/1980 | Anderson |
| 4,203,503 A | 5/1980 | Bertotti et al. |
| 4,209,076 A | 6/1980 | Bertotti et al. |
| 4,223,677 A | 9/1980 | Anderson |
| 4,233,025 A | 11/1980 | Larson et al. |
| 4,233,978 A | 11/1980 | Hickey |
| 4,246,901 A | 1/1981 | Frosch et al. |
| 4,253,542 A | 3/1981 | Ruspa et al. |
| 4,257,418 A | 3/1981 | Hessner |
| 4,270,539 A | 6/1981 | Frosch et al. |
| 4,281,655 A | 8/1981 | Terauchi |
| 4,292,916 A | 10/1981 | Bradley et al. |
| 4,330,239 A | 5/1982 | Gannaway |
| 4,352,356 A | 10/1982 | Tong |
| 4,360,933 A | 11/1982 | Kimura et al. |
| 4,365,363 A | 12/1982 | Windauer |
| 4,375,841 A | 3/1983 | Vielbig |
| 4,387,726 A | 6/1983 | Denard |
| 4,403,991 A | 9/1983 | Hill |
| 4,425,130 A | 1/1984 | Desmarais |
| 4,446,986 A | 5/1984 | Bowen et al. |
| 4,453,938 A | 6/1984 | Brendling |
| 4,457,314 A | 7/1984 | Knowles |
| 4,476,879 A | 10/1984 | Jackson |
| 4,526,688 A | 7/1985 | Schmidt et al. |
| 4,528,703 A | 7/1985 | Kraus |
| D280,438 S | 9/1985 | Wendt |
| 4,551,141 A | 11/1985 | Mcneil |
| 4,553,968 A | 11/1985 | Komis |
| 4,581,026 A | 4/1986 | Schneider |
| 4,589,516 A | 5/1986 | Inoue et al. |
| 4,601,716 A | 7/1986 | Smith |
| 4,610,675 A | 9/1986 | Triunfol |
| 4,620,333 A | 11/1986 | Ritter |
| 4,626,250 A | 12/1986 | Schneider |
| 4,627,846 A | 12/1986 | Ternstroem |
| 4,631,061 A | 12/1986 | Martin |
| 4,650,477 A | 3/1987 | Johnson |
| 4,655,754 A | 4/1987 | Richmond et al. |
| 4,656,675 A | 4/1987 | Fajnsztajn |
| 4,681,570 A | 7/1987 | Dalton |
| 4,681,577 A | 7/1987 | Stern et al. |
| 4,692,160 A | 9/1987 | Nussbaumer |
| 4,707,864 A | 11/1987 | Ikematsu et al. |
| 4,713,065 A | 12/1987 | Koot |
| 4,713,066 A | 12/1987 | Komis |
| 4,723,953 A | 2/1988 | Pratt et al. |
| 4,735,841 A | 4/1988 | Sourdet |
| 4,743,236 A | 5/1988 | Manschot |
| 4,747,166 A | 5/1988 | Kuntz |
| 4,752,944 A | 6/1988 | Conrads et al. |
| 4,769,215 A | 9/1988 | Ehrenkranz |
| 4,771,484 A | 9/1988 | Mozell |
| 4,772,280 A | 9/1988 | Rooyakkers |
| 4,784,654 A | 11/1988 | Beecher |
| 4,790,830 A | 12/1988 | Hamacher |
| 4,790,835 A | 12/1988 | Elias |
| 4,791,686 A | 12/1988 | Taniguchi et al. |
| 4,795,449 A | 1/1989 | Schneider et al. |
| 4,798,603 A | 1/1989 | Meyer et al. |
| 4,799,928 A | 1/1989 | Crowley |
| 4,804,377 A | 2/1989 | Hanifl et al. |
| 4,812,053 A | 3/1989 | Bhattacharjee |
| 4,813,943 A | 3/1989 | Smith |
| 4,820,297 A | 4/1989 | Kaufman et al. |
| 4,846,818 A | 7/1989 | Keldahl et al. |
| 4,846,909 A | 7/1989 | Klug et al. |
| 4,865,595 A | 9/1989 | Heyden |
| 4,880,417 A | 11/1989 | Yabrov et al. |
| 4,882,794 A | 11/1989 | Stewart |
| 4,883,465 A | 11/1989 | Brennan |
| 4,886,498 A | 12/1989 | Newton |
| 4,886,508 A | 12/1989 | Washington |
| 4,886,509 A | 12/1989 | Mattsson |
| 4,889,532 A | 12/1989 | Metz et al. |
| 4,889,533 A | 12/1989 | Beecher |
| 4,890,691 A | 1/1990 | Ching-Ho |
| 4,903,254 A | 2/1990 | Haas |
| 4,904,248 A | 2/1990 | Vaillancourt |
| 4,905,692 A | 3/1990 | More |
| 4,936,838 A | 6/1990 | Cross et al. |
| 4,955,922 A | 9/1990 | Terauchi |
| 4,957,487 A | 9/1990 | Gerow |

(56) References Cited

U.S. PATENT DOCUMENTS

| | | | |
|---|---|---|---|
| 4,965,460 A | 10/1990 | Tanaka et al. | |
| 4,986,823 A | 1/1991 | Anderson et al. | |
| 4,987,849 A | 1/1991 | Sherman | |
| 5,002,541 A | 3/1991 | Conkling et al. | |
| 5,004,463 A | 4/1991 | Nigay | |
| 5,031,248 A | 7/1991 | Kemper | |
| 5,045,077 A | 9/1991 | Blake | |
| 5,045,283 A | 9/1991 | Patel | |
| 5,049,144 A | 9/1991 | Payton | |
| 5,053,339 A | 10/1991 | Patel | |
| 5,057,092 A | 10/1991 | Webster | |
| 5,058,088 A | 10/1991 | Haas et al. | |
| 5,071,347 A | 12/1991 | McGuire | |
| 5,078,707 A * | 1/1992 | Peter Klug | A61F 5/453 604/349 |
| 5,084,037 A | 1/1992 | Barnett | |
| 5,100,396 A | 3/1992 | Zamierowski | |
| 5,112,324 A * | 5/1992 | Wallace | A61G 9/006 604/349 |
| 5,147,301 A | 9/1992 | Ruvio | |
| 5,176,667 A | 1/1993 | Debring | |
| 5,195,997 A | 3/1993 | Carns | |
| 5,196,654 A | 3/1993 | Diflora et al. | |
| 5,203,699 A | 4/1993 | McGuire | |
| 5,244,458 A | 9/1993 | Takasu | |
| 5,246,454 A | 9/1993 | Peterson | |
| 5,267,988 A | 12/1993 | Farkas | |
| 5,275,307 A | 1/1994 | Freese | |
| 5,282,795 A | 2/1994 | Finney | |
| 5,294,983 A | 3/1994 | Ersoz et al. | |
| 5,295,983 A | 3/1994 | Kubo | |
| 5,300,052 A | 4/1994 | Kubo | |
| 5,304,749 A | 4/1994 | Crandell | |
| 5,312,383 A | 5/1994 | Kubalak | |
| 5,318,550 A | 6/1994 | Cermak et al. | |
| 5,330,459 A | 7/1994 | Lavon et al. | |
| 5,340,840 A | 8/1994 | Park et al. | |
| 5,382,244 A | 1/1995 | Telang | |
| 5,409,014 A | 4/1995 | Napoli et al. | |
| 5,411,495 A | 5/1995 | Willingham | |
| 5,423,784 A | 6/1995 | Metz | |
| 5,456,246 A | 10/1995 | Schmieding et al. | |
| 5,466,229 A | 11/1995 | Elson et al. | |
| 5,478,334 A | 12/1995 | Bernstein | |
| 5,499,977 A | 3/1996 | Marx | |
| 5,543,042 A | 8/1996 | Filan et al. | |
| D373,928 S | 9/1996 | Green | |
| 5,582,604 A | 12/1996 | Ahr et al. | |
| 5,592,950 A | 1/1997 | Kopelowicz | |
| 5,605,161 A | 2/1997 | Cross | |
| 5,618,277 A | 4/1997 | Goulter | |
| 5,628,735 A | 5/1997 | Skow | |
| 5,636,643 A | 6/1997 | Argenta et al. | |
| 5,637,104 A | 6/1997 | Ball et al. | |
| 5,674,212 A | 10/1997 | Osborn et al. | |
| 5,678,564 A | 10/1997 | Lawrence et al. | |
| 5,678,654 A | 10/1997 | Uzawa | |
| 5,687,429 A | 11/1997 | Rahlff | |
| 5,695,485 A | 12/1997 | Duperret et al. | |
| 5,700,254 A | 12/1997 | Mcdowall et al. | |
| 5,701,612 A | 12/1997 | Daneshvar | |
| 5,705,777 A | 1/1998 | Flanigan et al. | |
| 5,752,944 A | 5/1998 | Dann et al. | |
| 5,763,333 A | 6/1998 | Suzuki et al. | |
| 5,772,644 A | 6/1998 | Bark et al. | |
| 5,792,132 A | 8/1998 | Garcia | |
| 5,827,243 A | 10/1998 | Palestrant | |
| 5,827,247 A | 10/1998 | Kay | |
| 5,827,250 A | 10/1998 | Fujioka et al. | |
| 5,827,257 A | 10/1998 | Fujioka et al. | |
| D401,699 S | 11/1998 | Herchenbach et al. | |
| 5,859,393 A | 1/1999 | Cummins et al. | |
| 5,865,378 A | 2/1999 | Hollinshead et al. | |
| 5,876,393 A | 3/1999 | Ahr et al. | |
| 5,887,291 A | 3/1999 | Bellizzi | |
| 5,891,125 A | 4/1999 | Plumley | |
| 5,894,608 A | 4/1999 | Birbara | |
| D409,303 S | 5/1999 | Oepping | |
| 5,911,222 A | 6/1999 | Lawrence et al. | |
| 5,957,904 A | 9/1999 | Holland | |
| 5,968,026 A | 10/1999 | Osborn et al. | |
| 5,972,505 A | 10/1999 | Phillips et al. | |
| 6,007,526 A | 12/1999 | Passalaqua et al. | |
| 6,039,060 A | 3/2000 | Rower | |
| 6,050,983 A | 4/2000 | Moore et al. | |
| 6,059,762 A | 5/2000 | Boyer et al. | |
| 6,063,064 A | 5/2000 | Tuckey et al. | |
| 6,098,625 A | 8/2000 | Winkler | |
| 6,105,174 A | 8/2000 | Karlsten et al. | |
| 6,113,582 A | 9/2000 | Dwork | |
| 6,117,163 A | 9/2000 | Bierman | |
| 6,123,398 A | 9/2000 | Arai et al. | |
| 6,129,718 A | 10/2000 | Wada et al. | |
| 6,131,964 A | 10/2000 | Sareshwala | |
| 6,152,902 A | 11/2000 | Christian et al. | |
| 6,164,569 A | 12/2000 | Hollinshead et al. | |
| 6,177,606 B1 | 1/2001 | Etheredge et al. | |
| 6,209,142 B1 | 4/2001 | Mattsson et al. | |
| 6,220,050 B1 | 4/2001 | Cooksey | |
| 6,244,311 B1 | 6/2001 | Hand et al. | |
| 6,248,096 B1 | 6/2001 | Dwork et al. | |
| 6,263,887 B1 | 7/2001 | Dunn | |
| 6,283,246 B1 | 9/2001 | Nishikawa | |
| 6,311,339 B1 | 11/2001 | Kraus | |
| 6,336,919 B1 | 1/2002 | Davis et al. | |
| 6,338,729 B1 | 1/2002 | Wada et al. | |
| 6,352,525 B1 | 3/2002 | Wakabayashi | |
| 6,394,988 B1 | 5/2002 | Hashimoto | |
| 6,398,742 B1 | 6/2002 | Kim | |
| 6,406,463 B1 | 6/2002 | Brown | |
| 6,409,712 B1 | 6/2002 | Dutari et al. | |
| 6,416,500 B1 | 7/2002 | Wada et al. | |
| 6,423,045 B1 | 7/2002 | Wise et al. | |
| 6,428,521 B1 | 8/2002 | Droll | |
| 6,428,522 B1 | 8/2002 | Dipalma et al. | |
| 6,446,454 B1 | 9/2002 | Lee et al. | |
| 6,475,198 B1 | 11/2002 | Lipman et al. | |
| 6,479,726 B1 | 11/2002 | Cole et al. | |
| 6,491,673 B1 | 12/2002 | Palumbo et al. | |
| 6,508,794 B1 | 1/2003 | Palumbo et al. | |
| 6,524,292 B1 | 2/2003 | Dipalma et al. | |
| 6,540,729 B1 | 4/2003 | Wada et al. | |
| 6,547,771 B2 | 4/2003 | Robertson et al. | |
| 6,569,133 B2 | 5/2003 | Cheng et al. | |
| D476,518 S | 7/2003 | Doppelt | |
| 6,592,560 B2 | 7/2003 | Snyder et al. | |
| 6,610,038 B1 | 8/2003 | Dipalma et al. | |
| 6,618,868 B2 | 9/2003 | Minnick | |
| 6,620,142 B1 | 9/2003 | Flueckiger | |
| 6,629,651 B1 | 10/2003 | Male et al. | |
| 6,635,038 B2 | 10/2003 | Scovel | |
| 6,652,495 B1 | 11/2003 | Walker | |
| 6,666,850 B1 | 12/2003 | Ahr et al. | |
| 6,685,684 B1 | 2/2004 | Falconer | |
| 6,695,828 B1 | 2/2004 | Dipalma et al. | |
| 6,699,174 B1 | 3/2004 | Bennett | |
| 6,700,034 B1 | 3/2004 | Lindsay et al. | |
| 6,702,793 B1 | 3/2004 | Sweetser et al. | |
| 6,706,027 B2 | 3/2004 | Harvie et al. | |
| 6,732,384 B2 | 5/2004 | Scott | |
| 6,736,977 B1 | 5/2004 | Hall et al. | |
| 6,740,066 B2 | 5/2004 | Wolff et al. | |
| 6,764,477 B1 | 7/2004 | Chen et al. | |
| 6,783,519 B2 | 8/2004 | Samuelsson | |
| 6,796,974 B2 | 9/2004 | Palumbo et al. | |
| 6,814,547 B2 | 11/2004 | Childers et al. | |
| 6,849,065 B2 | 2/2005 | Schmidt et al. | |
| 6,857,137 B2 | 2/2005 | Otto | |
| 6,885,690 B2 | 4/2005 | Aggerstam et al. | |
| 6,888,044 B2 | 5/2005 | Fell et al. | |
| 6,893,425 B2 | 5/2005 | Dunn et al. | |
| 6,912,737 B2 | 7/2005 | Ernest et al. | |
| 6,918,899 B2 | 7/2005 | Harvie | |
| 6,979,324 B2 | 12/2005 | Byrodi et al. | |

(56) References Cited

U.S. PATENT DOCUMENTS

| | | |
|---|---|---|
| 7,018,366 B2 | 3/2006 | Easter |
| 7,066,411 B2 | 6/2006 | Male et al. |
| 7,122,023 B1 | 10/2006 | Hinoki |
| 7,125,399 B2 | 10/2006 | Miskie |
| 7,131,964 B2 | 11/2006 | Harvie |
| 7,135,012 B2 | 11/2006 | Harvie |
| 7,141,043 B2 | 11/2006 | Harvie |
| D533,972 S | 12/2006 | La |
| 7,160,273 B2 | 1/2007 | Greter et al. |
| 7,171,699 B2 | 2/2007 | Ernest et al. |
| 7,171,871 B2 | 2/2007 | Kozak |
| 7,179,951 B2 | 2/2007 | Krishnaswamy-Mirle et al. |
| 7,181,781 B1 | 2/2007 | Trabold et al. |
| 7,186,245 B1 | 3/2007 | Cheng et al. |
| 7,192,424 B2 | 3/2007 | Cooper |
| 7,219,764 B1 | 5/2007 | Forbes |
| 7,220,250 B2 | 5/2007 | Suzuki et al. |
| D562,975 S | 2/2008 | Otto |
| 7,335,189 B2 | 2/2008 | Harvie |
| 7,358,282 B2 | 4/2008 | Krueger et al. |
| 7,390,320 B2 | 6/2008 | Machida et al. |
| 7,438,706 B2 | 10/2008 | Koizumi et al. |
| 7,488,310 B2 | 2/2009 | Yang |
| 7,491,194 B1 | 2/2009 | Oliwa |
| D591,106 S | 4/2009 | Dominique et al. |
| 7,513,381 B2 | 4/2009 | Heng et al. |
| 7,520,872 B2 | 4/2009 | Biggie et al. |
| D593,801 S | 6/2009 | Wilson et al. |
| 7,540,364 B2 | 6/2009 | Sanderson |
| 7,549,511 B2 | 6/2009 | Marocco |
| 7,549,512 B2 | 6/2009 | Newberry |
| 7,585,293 B2 | 9/2009 | Vermaak |
| 7,588,560 B1 | 9/2009 | Dunlop |
| 7,637,905 B2 | 12/2009 | Saadat et al. |
| 7,665,359 B2 | 2/2010 | Barber |
| 7,682,347 B2 | 3/2010 | Parks et al. |
| 7,687,004 B2 | 3/2010 | Allen |
| 7,695,459 B2 | 4/2010 | Gilbert et al. |
| 7,695,460 B2 | 4/2010 | Wada et al. |
| 7,699,818 B2 | 4/2010 | Gilbert |
| 7,699,831 B2 | 4/2010 | Bengtson et al. |
| 7,722,584 B2 | 5/2010 | Tanaka et al. |
| 7,727,206 B2 | 6/2010 | Gorres |
| 7,740,620 B2 | 6/2010 | Gilbert et al. |
| 7,749,205 B2 | 7/2010 | Tazoe et al. |
| 7,755,497 B2 | 7/2010 | Wada et al. |
| 7,766,887 B2 | 8/2010 | Burns et al. |
| D625,407 S | 10/2010 | Koizumi et al. |
| 7,806,879 B2 | 10/2010 | Brooks et al. |
| 7,811,272 B2 | 10/2010 | Lindsay et al. |
| 7,815,067 B2 | 10/2010 | Matsumoto et al. |
| 7,833,169 B2 | 11/2010 | Hannon |
| 7,857,806 B2 | 12/2010 | Karpowicz et al. |
| 7,866,942 B2 | 1/2011 | Harvie |
| 7,871,385 B2 | 1/2011 | Levinson et al. |
| 7,875,010 B2 | 1/2011 | Frazier et al. |
| 7,901,389 B2 | 3/2011 | Mombrinie |
| 7,927,320 B2 | 4/2011 | Goldwasser et al. |
| 7,927,321 B2 | 4/2011 | Marland |
| 7,931,634 B2 | 4/2011 | Swiecicki et al. |
| 7,939,706 B2 | 5/2011 | Okabe et al. |
| 7,946,443 B2 | 5/2011 | Stull et al. |
| 7,947,025 B2 | 5/2011 | Buglino et al. |
| 7,963,419 B2 | 6/2011 | Burney et al. |
| 7,976,519 B2 | 7/2011 | Bubb et al. |
| 7,993,318 B2 | 8/2011 | Olsson et al. |
| 8,015,627 B2 | 9/2011 | Baker et al. |
| 8,016,071 B1 | 9/2011 | Martinus et al. |
| 8,028,460 B2 | 10/2011 | Williams |
| 8,047,398 B2 | 11/2011 | Dimartino et al. |
| 8,083,094 B2 | 12/2011 | Caulfield et al. |
| 8,128,608 B2 | 3/2012 | Thevenin |
| 8,181,651 B2 | 5/2012 | Pinel |
| 8,181,819 B2 | 5/2012 | Burney et al. |
| 8,211,063 B2 | 7/2012 | Bierman et al. |
| 8,221,369 B2 | 7/2012 | Parks et al. |
| 8,241,262 B2 | 8/2012 | Mahnensmith |
| 8,277,426 B2 | 10/2012 | Wilcox et al. |
| 8,287,508 B1 | 10/2012 | Sanchez |
| 8,303,554 B2 | 11/2012 | Tsai et al. |
| 8,322,565 B2 | 12/2012 | Caulfield et al. |
| 8,337,477 B2 | 12/2012 | Parks et al. |
| D674,241 S | 1/2013 | Bickert et al. |
| 8,343,122 B2 | 1/2013 | Gorres |
| 8,343,125 B2 | 1/2013 | Kawazoe et al. |
| 8,353,074 B2 | 1/2013 | Krebs |
| 8,353,886 B2 | 1/2013 | Bester et al. |
| D676,241 S | 2/2013 | Merrill |
| 8,388,588 B2 | 3/2013 | Wada et al. |
| D679,807 S | 4/2013 | Burgess et al. |
| 8,425,482 B2 | 4/2013 | Khoubnazar |
| 8,434,586 B2 | 5/2013 | Pawelski et al. |
| 8,449,510 B2 | 5/2013 | Martini et al. |
| D684,260 S | 6/2013 | Lund et al. |
| 8,470,230 B2 | 6/2013 | Caulfield et al. |
| 8,479,941 B2 | 7/2013 | Matsumoto et al. |
| 8,479,949 B2 | 7/2013 | Henkel |
| 8,500,719 B1 | 8/2013 | Simpson et al. |
| 8,512,301 B2 | 8/2013 | Ma |
| 8,529,530 B2 | 9/2013 | Koch et al. |
| 8,535,284 B2 | 9/2013 | Joder et al. |
| 8,546,639 B2 | 10/2013 | Wada et al. |
| 8,551,075 B2 | 10/2013 | Bengtson |
| 8,568,376 B2 | 10/2013 | Delattre et al. |
| D694,404 S | 11/2013 | Burgess et al. |
| 8,585,683 B2 | 11/2013 | Bengtson et al. |
| 8,652,112 B2 | 2/2014 | Johannison et al. |
| 8,669,412 B2 | 3/2014 | Fernkvist et al. |
| D702,973 S | 4/2014 | Norland et al. |
| 8,703,032 B2 | 4/2014 | Menon et al. |
| D704,330 S | 5/2014 | Cicatelli |
| D704,510 S | 5/2014 | Mason et al. |
| D705,423 S | 5/2014 | Walsh Cutler |
| D705,926 S | 5/2014 | Burgess et al. |
| 8,714,394 B2 | 5/2014 | Wulf |
| 8,715,267 B2 | 5/2014 | Bengtson et al. |
| 8,757,425 B2 | 6/2014 | Copeland |
| 8,777,032 B2 | 7/2014 | Biesecker et al. |
| 8,808,260 B2 | 8/2014 | Koch et al. |
| 8,864,730 B2 | 10/2014 | Conway et al. |
| 8,881,923 B2 | 11/2014 | Higginson |
| 8,882,731 B2 | 11/2014 | Suzuki et al. |
| 8,936,585 B2 | 1/2015 | Carson et al. |
| D729,581 S | 5/2015 | Boroski |
| 9,028,460 B2 | 5/2015 | Medeiros |
| 9,056,698 B2 | 6/2015 | Noer |
| 9,078,792 B2 | 7/2015 | Ruiz |
| 9,145,879 B2 | 9/2015 | Pirovano et al. |
| 9,173,602 B2 | 11/2015 | Gilbert |
| 9,173,799 B2 | 11/2015 | Tanimoto et al. |
| 9,187,220 B2 | 11/2015 | Biesecker et al. |
| 9,199,772 B2 | 12/2015 | Krippendorf |
| 9,233,020 B2 | 1/2016 | Matsumiya |
| 9,248,058 B2 | 2/2016 | Conway et al. |
| 9,308,118 B1 | 4/2016 | Dupree et al. |
| 9,309,029 B2 | 4/2016 | Incorvia et al. |
| 9,333,281 B2 | 5/2016 | Giezendanner et al. |
| 9,381,108 B2 | 7/2016 | Longoni et al. |
| 9,382,047 B2 | 7/2016 | Schmidtner et al. |
| 9,402,424 B2 | 8/2016 | Roy |
| 9,456,937 B2 | 10/2016 | Ellis |
| 9,480,595 B2 | 11/2016 | Baham et al. |
| 9,517,865 B2 | 12/2016 | Albers et al. |
| D777,941 S | 1/2017 | Piramoon |
| 9,533,806 B2 | 1/2017 | Ding et al. |
| 9,550,611 B2 | 1/2017 | Hodge |
| 9,555,930 B2 | 1/2017 | Campbell et al. |
| 9,623,159 B2 | 4/2017 | Locke |
| D789,522 S | 6/2017 | Burgess et al. |
| 9,687,849 B2 | 6/2017 | Bruno et al. |
| 9,694,949 B2 | 7/2017 | Hendricks et al. |
| 9,709,048 B2 | 7/2017 | Kinjo |
| 9,713,547 B2 | 7/2017 | Lee et al. |
| 9,732,754 B2 | 8/2017 | Huang et al. |

(56) References Cited

U.S. PATENT DOCUMENTS

| | | |
|---|---|---|
| 9,752,564 B2 | 9/2017 | Arceno et al. |
| 9,788,992 B2 | 10/2017 | Harvie |
| D804,907 S | 12/2017 | Sandoval |
| 9,868,564 B2 | 1/2018 | McGirr et al. |
| D814,239 S | 4/2018 | Arora |
| D817,484 S | 5/2018 | Lafond |
| 10,037,640 B2 | 7/2018 | Gordon |
| 10,058,470 B2 | 8/2018 | Phillips |
| 10,098,990 B2 | 10/2018 | Koch et al. |
| D835,264 S | 12/2018 | Mozzicato et al. |
| D835,779 S | 12/2018 | Mozzicato et al. |
| D840,533 S | 2/2019 | Mozzicato et al. |
| D840,534 S | 2/2019 | Mozzicato et al. |
| 10,225,376 B2 | 3/2019 | Perez Martinez |
| 10,226,376 B2 | 3/2019 | Sanchez et al. |
| 10,258,517 B1 | 4/2019 | Maschino et al. |
| D848,612 S | 5/2019 | Mozzicato et al. |
| 10,307,305 B1 | 6/2019 | Hodges |
| 10,335,121 B2 | 7/2019 | Desai |
| D856,512 S | 8/2019 | Cowart et al. |
| 10,376,406 B2 | 8/2019 | Newton |
| 10,376,407 B2 | 8/2019 | Newton |
| 10,390,989 B2 | 8/2019 | Sanchez et al. |
| D858,144 S | 9/2019 | Fu |
| 10,406,039 B2 | 9/2019 | Mllarreal |
| 10,407,222 B2 | 9/2019 | Allen |
| 10,478,356 B2 | 11/2019 | Griffin |
| 10,500,108 B1 | 12/2019 | Maschino et al. |
| 10,538,366 B2 | 1/2020 | Pentelovitch et al. |
| 10,569,938 B2 | 2/2020 | Zhao et al. |
| 10,577,156 B2 | 3/2020 | Dagnelie et al. |
| RE47,930 E | 4/2020 | Cho |
| 10,618,721 B2 | 4/2020 | Vazin |
| D884,390 S | 5/2020 | Wang |
| 10,669,079 B2 | 6/2020 | Freedman et al. |
| D892,315 S | 8/2020 | Airy |
| 10,730,672 B2 | 8/2020 | Bertram et al. |
| 10,737,848 B2 | 8/2020 | Philip et al. |
| 10,765,854 B2 | 9/2020 | Law et al. |
| 10,766,670 B2 | 9/2020 | Kittmann |
| 10,799,386 B1 | 10/2020 | Harrison |
| 10,806,642 B2 | 10/2020 | Tagomori et al. |
| D901,214 S | 11/2020 | Hu |
| 10,849,799 B2 | 12/2020 | Nishikawa et al. |
| 10,857,025 B2 | 12/2020 | Davis et al. |
| 10,865,017 B1 | 12/2020 | Cowart et al. |
| 10,889,412 B2 | 1/2021 | West et al. |
| 10,913,581 B2 | 2/2021 | Stahlecker |
| D912,244 S | 3/2021 | Rehm et al. |
| 10,952,889 B2 | 3/2021 | Newton et al. |
| 10,973,378 B2 | 4/2021 | Ryu et al. |
| 10,973,678 B2 | 4/2021 | Newton et al. |
| 10,974,874 B2 | 4/2021 | Ragias et al. |
| 11,000,401 B2 | 5/2021 | Ecklund et al. |
| D923,365 S | 6/2021 | Wang |
| 11,026,829 B2 | 6/2021 | Harvie |
| 11,027,900 B2 | 6/2021 | Liu |
| 11,045,346 B2 | 6/2021 | Argent et al. |
| D928,946 S | 8/2021 | Sanchez et al. |
| 11,090,183 B2 | 8/2021 | Sanchez et al. |
| 11,160,695 B2 | 11/2021 | Febo et al. |
| 11,160,697 B2 | 11/2021 | Maschino et al. |
| 11,168,420 B2 | 11/2021 | Kinugasa et al. |
| 11,179,506 B2 | 11/2021 | Barr et al. |
| 11,226,376 B2 | 1/2022 | Yamauchi et al. |
| 11,253,407 B2 | 2/2022 | Miao et al. |
| 11,326,586 B2 | 5/2022 | Milner et al. |
| 11,369,508 B2 | 6/2022 | Ecklund et al. |
| 11,369,524 B2 | 6/2022 | Hubbard et al. |
| 11,376,152 B2 | 7/2022 | Sanchez et al. |
| 11,382,786 B2 | 7/2022 | Sanchez et al. |
| 11,382,788 B2 | 7/2022 | Hjorth et al. |
| 11,389,318 B2 | 7/2022 | Radl et al. |
| 11,395,871 B2 | 7/2022 | Radl et al. |
| 11,399,990 B2 | 8/2022 | Suyama |
| 11,426,303 B2 | 8/2022 | Davis et al. |
| 11,504,265 B2 | 11/2022 | Godinez et al. |
| 11,529,252 B2 | 12/2022 | Glithero et al. |
| 11,547,788 B2 | 1/2023 | Radl et al. |
| 11,806,266 B2 | 11/2023 | Sanchez et al. |
| 11,839,567 B2 | 12/2023 | Davis et al. |
| D1,010,109 S | 1/2024 | Ecklund et al. |
| 11,857,716 B2 | 1/2024 | Lee et al. |
| 11,865,030 B2 | 1/2024 | Davis et al. |
| 11,890,221 B2 | 2/2024 | Ulreich et al. |
| 11,925,575 B2 | 3/2024 | Newton |
| 11,938,053 B2 | 3/2024 | Austermann et al. |
| 11,944,740 B2 | 4/2024 | Hughett et al. |
| 12,023,457 B2 | 7/2024 | Mann et al. |
| 12,042,422 B2 | 7/2024 | Davis et al. |
| 2001/0037097 A1 | 11/2001 | Cheng et al. |
| 2001/0054426 A1 | 12/2001 | Knudson et al. |
| 2002/0019614 A1 | 2/2002 | Woon |
| 2002/0026161 A1 | 2/2002 | Grundke |
| 2002/0087131 A1 | 7/2002 | Wolff et al. |
| 2002/0091364 A1 | 7/2002 | Prabhakar |
| 2002/0189992 A1 | 12/2002 | Schmidt et al. |
| 2002/0193760 A1 | 12/2002 | Thompson |
| 2003/0004436 A1 | 1/2003 | Schmidt et al. |
| 2003/0032931 A1 | 2/2003 | Grundke et al. |
| 2003/0032944 A1 | 2/2003 | Cawood |
| 2003/0073964 A1 | 4/2003 | Palumbo et al. |
| 2003/0120178 A1 | 6/2003 | Heki |
| 2003/0157859 A1 | 8/2003 | Ishikawa |
| 2003/0181880 A1 | 9/2003 | Schwartz |
| 2003/0195484 A1 | 10/2003 | Harvie |
| 2003/0204173 A1 | 10/2003 | Burns et al. |
| 2003/0233079 A1 | 12/2003 | Parks et al. |
| 2004/0006321 A1 | 1/2004 | Cheng et al. |
| 2004/0015141 A1 | 1/2004 | Cheng et al. |
| 2004/0056122 A1 | 3/2004 | Male et al. |
| 2004/0084465 A1 | 5/2004 | Luburic |
| 2004/0127872 A1 | 7/2004 | Petryk et al. |
| 2004/0128749 A1 | 7/2004 | Scott |
| 2004/0143229 A1 | 7/2004 | Easter |
| 2004/0147863 A1 | 7/2004 | Diaz et al. |
| 2004/0147894 A1 | 7/2004 | Mizutani et al. |
| 2004/0158221 A1 | 8/2004 | Mizutani et al. |
| 2004/0176731 A1 | 9/2004 | Cheng et al. |
| 2004/0176746 A1 | 9/2004 | Forral |
| 2004/0191919 A1 | 9/2004 | Unger et al. |
| 2004/0200936 A1 | 10/2004 | Opperthauser |
| 2004/0207530 A1 | 10/2004 | Nielsen |
| 2004/0236292 A1 | 11/2004 | Tazoe et al. |
| 2004/0243075 A1 | 12/2004 | Harvie |
| 2004/0254547 A1 | 12/2004 | Okabe et al. |
| 2005/0010182 A1 | 1/2005 | Parks et al. |
| 2005/0033248 A1 | 2/2005 | Machida et al. |
| 2005/0065471 A1 | 3/2005 | Kuntz |
| 2005/0070861 A1 | 3/2005 | Okabe et al. |
| 2005/0070862 A1 | 3/2005 | Tazoe et al. |
| 2005/0082300 A1 | 4/2005 | Modrell et al. |
| 2005/0097662 A1 | 5/2005 | Leimkuhler et al. |
| 2005/0101924 A1 | 5/2005 | Elson et al. |
| 2005/0119630 A1 | 6/2005 | Harvie |
| 2005/0137557 A1 | 6/2005 | Swiecicki et al. |
| 2005/0154360 A1 | 7/2005 | Harvie |
| 2005/0177070 A1 | 8/2005 | Levinson et al. |
| 2005/0197639 A1 | 9/2005 | Mombrinie |
| 2005/0273920 A1 | 12/2005 | Marinas |
| 2005/0277904 A1 | 12/2005 | Chase et al. |
| 2005/0279359 A1 | 12/2005 | Leblanc et al. |
| 2006/0004332 A1 | 1/2006 | Marx |
| 2006/0015080 A1 | 1/2006 | Mahnensmith |
| 2006/0015081 A1 | 1/2006 | Suzuki et al. |
| 2006/0016778 A1 | 1/2006 | Park |
| 2006/0069359 A1 | 3/2006 | Dipalma et al. |
| 2006/0079854 A1 | 4/2006 | Kay et al. |
| 2006/0111648 A1 | 5/2006 | Vermaak |
| 2006/0155214 A1 | 7/2006 | Wightman |
| 2006/0171997 A1 | 8/2006 | Gruenbacher et al. |
| 2006/0200102 A1 | 9/2006 | Cooper |
| 2006/0229575 A1 | 10/2006 | Boiarski |
| 2006/0229576 A1 | 10/2006 | Conway et al. |

(56) References Cited

U.S. PATENT DOCUMENTS

| | | |
|---|---|---|
| 2006/0231648 A1 | 10/2006 | Male et al. |
| 2006/0235266 A1 | 10/2006 | Nan |
| 2006/0235359 A1 | 10/2006 | Marland |
| 2006/0241553 A1 | 10/2006 | Harvie |
| 2006/0269439 A1 | 11/2006 | White |
| 2006/0277670 A1 | 12/2006 | Baker et al. |
| 2007/0006368 A1 | 1/2007 | Key et al. |
| 2007/0010797 A1 | 1/2007 | Nishtala et al. |
| 2007/0016152 A1 | 1/2007 | Karpowicz et al. |
| 2007/0038194 A1 | 2/2007 | Wada et al. |
| 2007/0055209 A1 | 3/2007 | Patel et al. |
| 2007/0073252 A1* | 3/2007 | Forgrave ............... A61F 5/453 604/347 |
| 2007/0117880 A1 | 5/2007 | Elson et al. |
| 2007/0118993 A1 | 5/2007 | Bates |
| 2007/0135786 A1 | 6/2007 | Schmidt et al. |
| 2007/0137718 A1 | 6/2007 | Rushlander et al. |
| 2007/0149935 A1 | 6/2007 | Dirico |
| 2007/0191804 A1 | 8/2007 | Coley |
| 2007/0203464 A1 | 8/2007 | Green et al. |
| 2007/0214553 A1 | 9/2007 | Carromba et al. |
| 2007/0225663 A1 | 9/2007 | Watt et al. |
| 2007/0225666 A1 | 9/2007 | Otto |
| 2007/0225668 A1 | 9/2007 | Otto |
| 2007/0266486 A1 | 11/2007 | Ramirez |
| 2007/0282309 A1 | 12/2007 | Bengtson et al. |
| 2008/0004576 A1 | 1/2008 | Tanaka et al. |
| 2008/0015526 A1 | 1/2008 | Reiner et al. |
| 2008/0015527 A1 | 1/2008 | House |
| 2008/0033386 A1 | 2/2008 | Okabe et al. |
| 2008/0041869 A1 | 2/2008 | Backaert |
| 2008/0091153 A1 | 4/2008 | Harvie |
| 2008/0091158 A1 | 4/2008 | Yang |
| 2008/0114327 A1 | 5/2008 | Barge |
| 2008/0167634 A1 | 7/2008 | Kouta et al. |
| 2008/0183157 A1* | 7/2008 | Walters ............... A61F 5/453 604/544 |
| 2008/0215031 A1 | 9/2008 | Belfort et al. |
| 2008/0234642 A1 | 9/2008 | Patterson et al. |
| 2008/0269703 A1 | 10/2008 | Collins et al. |
| 2008/0281282 A1 | 11/2008 | Finger et al. |
| 2008/0287894 A1 | 11/2008 | Van Den Heuvel et al. |
| 2008/0312550 A1 | 12/2008 | Nishtala et al. |
| 2009/0025717 A1 | 1/2009 | Pinel |
| 2009/0048570 A1 | 2/2009 | Jensen |
| 2009/0056003 A1 | 3/2009 | Ivie et al. |
| 2009/0069761 A1 | 3/2009 | Vogel |
| 2009/0069765 A1 | 3/2009 | Wortham |
| 2009/0120179 A1 | 5/2009 | Nylander et al. |
| 2009/0192482 A1 | 7/2009 | Dodge et al. |
| 2009/0234312 A1 | 9/2009 | OToole et al. |
| 2009/0251510 A1 | 10/2009 | Noro et al. |
| 2009/0264840 A1 | 10/2009 | Mrginio |
| 2009/0270822 A1 | 10/2009 | Medeiros |
| 2009/0281510 A1 | 11/2009 | Fisher |
| 2010/0004612 A1 | 1/2010 | Thevenin |
| 2010/0058660 A1 | 3/2010 | Williams |
| 2010/0121289 A1 | 5/2010 | Parks et al. |
| 2010/0158168 A1 | 6/2010 | Murthy et al. |
| 2010/0160882 A1 | 6/2010 | Lowe |
| 2010/0174250 A1 | 7/2010 | Hu et al. |
| 2010/0185168 A1 | 7/2010 | Graauw et al. |
| 2010/0198172 A1 | 8/2010 | Wada et al. |
| 2010/0211032 A1 | 8/2010 | Tsai et al. |
| 2010/0234820 A1 | 9/2010 | Tsai et al. |
| 2010/0241104 A1 | 9/2010 | Gilbert |
| 2010/0263113 A1 | 10/2010 | Shelton et al. |
| 2010/0310845 A1 | 12/2010 | Bond et al. |
| 2011/0028920 A1 | 2/2011 | Johannison |
| 2011/0028922 A1 | 2/2011 | Kay et al. |
| 2011/0034889 A1 | 2/2011 | Smith |
| 2011/0036837 A1 | 2/2011 | Shang |
| 2011/0040267 A1 | 2/2011 | Wada et al. |
| 2011/0040271 A1 | 2/2011 | Rogers et al. |
| 2011/0054426 A1 | 3/2011 | Stewart et al. |
| 2011/0060299 A1 | 3/2011 | Wada et al. |
| 2011/0060300 A1 | 3/2011 | Weig et al. |
| 2011/0077495 A1 | 3/2011 | Gilbert |
| 2011/0077606 A1 | 3/2011 | Wilcox et al. |
| 2011/0087337 A1 | 4/2011 | Forsell |
| 2011/0137273 A1 | 6/2011 | Muellejans et al. |
| 2011/0145993 A1 | 6/2011 | Rader et al. |
| 2011/0152802 A1 | 6/2011 | Dicamillo et al. |
| 2011/0164147 A1 | 7/2011 | Takahashi et al. |
| 2011/0172620 A1 | 7/2011 | Khambatta |
| 2011/0172625 A1 | 7/2011 | Wada et al. |
| 2011/0202024 A1 | 8/2011 | Cozzens |
| 2011/0238023 A1 | 9/2011 | Slayton |
| 2011/0240648 A1 | 10/2011 | Tucker |
| 2011/0251572 A1 | 10/2011 | Nishtala et al. |
| 2011/0265889 A1 | 11/2011 | Tanaka et al. |
| 2011/0276020 A1 | 11/2011 | Mitsui |
| 2012/0029452 A1 | 2/2012 | Roedsten |
| 2012/0035577 A1 | 2/2012 | Tomes et al. |
| 2012/0041400 A1 | 2/2012 | Christensen |
| 2012/0059328 A1 | 3/2012 | Dikeman et al. |
| 2012/0066825 A1 | 3/2012 | Birbara et al. |
| 2012/0103347 A1 | 5/2012 | Wheaton et al. |
| 2012/0137420 A1 | 6/2012 | Gordon et al. |
| 2012/0165768 A1 | 6/2012 | Sekiyama et al. |
| 2012/0165786 A1 | 6/2012 | Chappa et al. |
| 2012/0210503 A1 | 8/2012 | Anzivino et al. |
| 2012/0233761 A1 | 9/2012 | Huang |
| 2012/0245541 A1 | 9/2012 | Suzuki et al. |
| 2012/0245542 A1 | 9/2012 | Suzuki et al. |
| 2012/0245547 A1 | 9/2012 | Wilcox et al. |
| 2012/0253303 A1 | 10/2012 | Suzuki et al. |
| 2012/0271259 A1 | 10/2012 | Ulert |
| 2012/0296305 A1 | 11/2012 | Barraza Khaled et al. |
| 2012/0316522 A1 | 12/2012 | Carter et al. |
| 2012/0330256 A1 | 12/2012 | Wilcox et al. |
| 2013/0006206 A1 | 1/2013 | Wada et al. |
| 2013/0045651 A1 | 2/2013 | Esteves et al. |
| 2013/0053804 A1 | 2/2013 | Soerensen et al. |
| 2013/0096523 A1 | 4/2013 | Chang et al. |
| 2013/0110059 A1 | 5/2013 | Kossow et al. |
| 2013/0138064 A1 | 5/2013 | Stroebech et al. |
| 2013/0150813 A1 | 6/2013 | Gordon et al. |
| 2013/0218112 A1 | 8/2013 | Thompson |
| 2013/0245496 A1 | 9/2013 | Wells et al. |
| 2013/0245586 A1 | 9/2013 | Jha |
| 2013/0292537 A1 | 11/2013 | Dirico |
| 2013/0330501 A1 | 12/2013 | Aizenberg et al. |
| 2014/0005647 A1 | 1/2014 | Shuffler et al. |
| 2014/0031774 A1 | 1/2014 | Bengtson |
| 2014/0039432 A1 | 2/2014 | Dunbar et al. |
| 2014/0157499 A1 | 6/2014 | Suzuki et al. |
| 2014/0171889 A1 | 6/2014 | Hopman et al. |
| 2014/0182051 A1 | 7/2014 | Tanimoto et al. |
| 2014/0196189 A1 | 7/2014 | Lee et al. |
| 2014/0276501 A1 | 9/2014 | Cisko |
| 2014/0303582 A1 | 10/2014 | Wright et al. |
| 2014/0316381 A1 | 10/2014 | Reglin |
| 2014/0325746 A1 | 11/2014 | Block |
| 2014/0348139 A1 | 11/2014 | Gomez Martinez |
| 2014/0352050 A1 | 12/2014 | Yao et al. |
| 2014/0371628 A1 | 12/2014 | Desai |
| 2015/0045757 A1* | 2/2015 | Lee ............... A61F 5/4401 604/385.03 |
| 2015/0047114 A1 | 2/2015 | Ramirez |
| 2015/0048089 A1 | 2/2015 | Robertson |
| 2015/0135423 A1 | 5/2015 | Sharpe et al. |
| 2015/0157300 A1 | 6/2015 | Ealovega et al. |
| 2015/0209194 A1 | 7/2015 | Heyman |
| 2015/0290425 A1 | 10/2015 | Macy et al. |
| 2015/0320583 A1 | 11/2015 | Harvie |
| 2015/0329255 A1 | 11/2015 | Rzepecki |
| 2015/0342799 A1 | 12/2015 | Michiels et al. |
| 2015/0359660 A1 | 12/2015 | Harvie |
| 2015/0366699 A1 | 12/2015 | Nelson |
| 2016/0029998 A1 | 2/2016 | Brister et al. |
| 2016/0030228 A1 | 2/2016 | Jones |
| 2016/0038356 A1 | 2/2016 | Yao et al. |
| 2016/0058322 A1 | 3/2016 | Brister et al. |

(56) References Cited

U.S. PATENT DOCUMENTS

| | | |
|---|---|---|
| 2016/0060001 A1 | 3/2016 | Wada et al. |
| 2016/0100976 A1 | 4/2016 | Conway et al. |
| 2016/0106604 A1 | 4/2016 | Timm |
| 2016/0113809 A1 | 4/2016 | Kim |
| 2016/0183689 A1 | 6/2016 | Miner |
| 2016/0256022 A1 | 9/2016 | Le |
| 2016/0270982 A1 | 9/2016 | Raycheck et al. |
| 2016/0278662 A1 | 9/2016 | Brister et al. |
| 2016/0357400 A1 | 12/2016 | Penha et al. |
| 2016/0366699 A1 | 12/2016 | Zhang et al. |
| 2016/0367226 A1 | 12/2016 | Newton et al. |
| 2016/0367411 A1 | 12/2016 | Justiz et al. |
| 2016/0367726 A1 | 12/2016 | Gratzer |
| 2016/0374848 A1 | 12/2016 | Sanchez et al. |
| 2017/0007438 A1 | 1/2017 | Harvie |
| 2017/0014560 A1 | 1/2017 | Minskoff et al. |
| 2017/0100276 A1 | 4/2017 | Joh |
| 2017/0128638 A1 | 5/2017 | Giezendanner et al. |
| 2017/0136209 A1 | 5/2017 | Burnett et al. |
| 2017/0143534 A1 | 5/2017 | Sanchez |
| 2017/0165100 A1 | 6/2017 | Jackson et al. |
| 2017/0165405 A1 | 6/2017 | Muser et al. |
| 2017/0189225 A1 | 7/2017 | Voorhees et al. |
| 2017/0202692 A1 | 7/2017 | Laniado |
| 2017/0216081 A1 | 8/2017 | Accosta |
| 2017/0246026 A1 | 8/2017 | Laniado |
| 2017/0252014 A1 | 9/2017 | Siller Gonzalez et al. |
| 2017/0252202 A9 | 9/2017 | Sanchez et al. |
| 2017/0266031 A1 | 9/2017 | Sanchez et al. |
| 2017/0266658 A1 | 9/2017 | Bruno et al. |
| 2017/0281399 A1 | 10/2017 | Vanmiddendorp et al. |
| 2017/0312116 A1 | 11/2017 | Laniado |
| 2017/0325788 A1 | 11/2017 | Ealovega et al. |
| 2017/0333244 A1 | 11/2017 | Laniado |
| 2017/0042748 A1 | 12/2017 | Griffin |
| 2017/0348139 A1 | 12/2017 | Newton et al. |
| 2017/0354532 A1 | 12/2017 | Holt |
| 2017/0354551 A1 | 12/2017 | Gawley et al. |
| 2017/0367873 A1 | 12/2017 | Grannum |
| 2018/0002075 A1 | 1/2018 | Lee |
| 2018/0008451 A1 | 1/2018 | Stroebech |
| 2018/0008804 A1 | 1/2018 | Laniado |
| 2018/0021218 A1 | 1/2018 | Brosch et al. |
| 2018/0028349 A1 | 2/2018 | Newton et al. |
| 2018/0037384 A1 | 2/2018 | Archeny et al. |
| 2018/0049910 A1 | 2/2018 | Newton |
| 2018/0064572 A1 | 3/2018 | Wiltshire |
| 2018/0104131 A1 | 4/2018 | Killian |
| 2018/0127187 A1 | 5/2018 | Sewell |
| 2018/0193215 A1 | 7/2018 | Davies et al. |
| 2018/0200101 A1 | 7/2018 | Su |
| 2018/0228642 A1 | 8/2018 | Davis et al. |
| 2018/0256384 A1 | 9/2018 | Kasirye |
| 2018/0271694 A1 | 9/2018 | Fernandez et al. |
| 2018/0317892 A1 | 11/2018 | Catlin |
| 2018/0325748 A1 | 11/2018 | Sharma et al. |
| 2019/0001030 A1 | 1/2019 | Braga et al. |
| 2019/0021899 A1 | 1/2019 | Vlet |
| 2019/0038451 A1 | 2/2019 | Harvie |
| 2019/0046102 A1 | 2/2019 | Kushnir et al. |
| 2019/0059938 A1 | 2/2019 | Holsten |
| 2019/0091059 A1 | 3/2019 | Gabriel |
| 2019/0100362 A1 | 4/2019 | Meyers et al. |
| 2019/0133814 A1 | 5/2019 | Tammen et al. |
| 2019/0142624 A1 | 5/2019 | Sanchez et al. |
| 2019/0224036 A1 | 7/2019 | Sanchez et al. |
| 2019/0247222 A1 | 8/2019 | Ecklund et al. |
| 2019/0247223 A1 | 8/2019 | Brun et al. |
| 2019/0282391 A1 | 9/2019 | Johannes et al. |
| 2019/0314189 A1 | 10/2019 | Acosta |
| 2019/0314190 A1 | 10/2019 | Sanchez et al. |
| 2019/0321587 A1 | 10/2019 | Mcmenamin et al. |
| 2019/0344934 A1 | 11/2019 | Faerber et al. |
| 2019/0365307 A1 | 12/2019 | Laing et al. |
| 2019/0365561 A1 | 12/2019 | Newton et al. |
| 2020/0008985 A1 | 1/2020 | Nguyen et al. |
| 2020/0016012 A1 | 1/2020 | Dutkiewicz |
| 2020/0030595 A1 | 1/2020 | Boukidjian et al. |
| 2020/0046544 A1 | 2/2020 | Godinez et al. |
| 2020/0055638 A1 | 2/2020 | Lau et al. |
| 2020/0070392 A1 | 3/2020 | Huber et al. |
| 2020/0085609 A1 | 3/2020 | Schelch et al. |
| 2020/0085610 A1 | 3/2020 | Cohn et al. |
| 2020/0086090 A1 | 3/2020 | Von Weymarn-schärli et al. |
| 2020/0107518 A1 | 4/2020 | Hiroshima et al. |
| 2020/0129322 A1* | 4/2020 | Leuckel ............... A61F 5/4556 |
| 2020/0171217 A9 | 6/2020 | Braga et al. |
| 2020/0206039 A1 | 7/2020 | Mclain |
| 2020/0214910 A1 | 7/2020 | Varona et al. |
| 2020/0216898 A1 | 7/2020 | Hubbell |
| 2020/0216989 A1 | 7/2020 | Kinugasa et al. |
| 2020/0229964 A1 | 7/2020 | Staali et al. |
| 2020/0231343 A1 | 7/2020 | Freedman et al. |
| 2020/0232841 A1 | 7/2020 | Satish et al. |
| 2020/0246172 A1 | 8/2020 | Ho |
| 2020/0246203 A1 | 8/2020 | Tulk et al. |
| 2020/0255189 A1 | 8/2020 | Liu |
| 2020/0261280 A1 | 8/2020 | Heyman |
| 2020/0276046 A1 | 9/2020 | Staali et al. |
| 2020/0306075 A1 | 10/2020 | Newton et al. |
| 2020/0315837 A1 | 10/2020 | Radl et al. |
| 2020/0315838 A1 | 10/2020 | Eckert |
| 2020/0315872 A1 | 10/2020 | Viens et al. |
| 2020/0315874 A1 | 10/2020 | Viens et al. |
| 2020/0331672 A1 | 10/2020 | Bertram et al. |
| 2020/0345332 A1 | 11/2020 | Duval |
| 2020/0353135 A1 | 11/2020 | Gregory et al. |
| 2020/0367677 A1 | 11/2020 | Silsby et al. |
| 2020/0369444 A1 | 11/2020 | Silsby et al. |
| 2020/0375781 A1 | 12/2020 | Staali et al. |
| 2020/0375810 A1 | 12/2020 | Carlin et al. |
| 2020/0385179 A1 | 12/2020 | McCourt |
| 2020/0390591 A1 | 12/2020 | Glithero et al. |
| 2020/0390592 A1 | 12/2020 | Merrill |
| 2020/0405521 A1 | 12/2020 | Glasroe |
| 2021/0008771 A1 | 1/2021 | Huber et al. |
| 2021/0009323 A1 | 1/2021 | Markarian et al. |
| 2021/0020072 A1 | 1/2021 | Moehring et al. |
| 2021/0059853 A1 | 3/2021 | Davis et al. |
| 2021/0061523 A1 | 3/2021 | Bytheway |
| 2021/0069005 A1 | 3/2021 | Sanchez et al. |
| 2021/0069008 A1 | 3/2021 | Blabas et al. |
| 2021/0069009 A1 | 3/2021 | Im |
| 2021/0069030 A1 | 3/2021 | Nishikawa et al. |
| 2021/0077993 A1 | 3/2021 | Nazareth et al. |
| 2021/0113749 A1 | 4/2021 | Radl et al. |
| 2021/0121318 A1 | 4/2021 | Pinlac |
| 2021/0137724 A1 | 5/2021 | Ecklund et al. |
| 2021/0138190 A1 | 5/2021 | Erbey et al. |
| 2021/0154055 A1 | 5/2021 | Mllarreal |
| 2021/0170079 A1 | 6/2021 | Radl et al. |
| 2021/0178390 A1 | 6/2021 | Oueslati et al. |
| 2021/0186742 A1 | 6/2021 | Newton et al. |
| 2021/0212865 A1 | 7/2021 | Wallajapet et al. |
| 2021/0220162 A1 | 7/2021 | Jamison |
| 2021/0220163 A1 | 7/2021 | Mayrand |
| 2021/0228400 A1 | 7/2021 | Glithero |
| 2021/0228401 A1 | 7/2021 | Becker et al. |
| 2021/0228795 A1 | 7/2021 | Hughett et al. |
| 2021/0229877 A1 | 7/2021 | Ragias et al. |
| 2021/0236323 A1 | 8/2021 | Austermann et al. |
| 2021/0236324 A1 | 8/2021 | Sweeney |
| 2021/0251814 A1 | 8/2021 | Jönegren et al. |
| 2021/0267787 A1 | 9/2021 | Nazemi |
| 2021/0275343 A1 | 9/2021 | Sanchez et al. |
| 2021/0275344 A1 | 9/2021 | Wing |
| 2021/0290454 A1 | 9/2021 | Yamada |
| 2021/0315727 A1 | 10/2021 | Jiang |
| 2021/0353450 A1 | 11/2021 | Sharma et al. |
| 2021/0361469 A1 | 11/2021 | Liu et al. |
| 2021/0369495 A1 | 12/2021 | Cheng et al. |
| 2021/0386925 A1 | 12/2021 | Hartwell et al. |
| 2021/0393433 A1 | 12/2021 | Godinez et al. |
| 2022/0023091 A1 | 1/2022 | Ecklund et al. |

(56) References Cited

U.S. PATENT DOCUMENTS

| | | |
|---|---|---|
| 2022/0031523 A1 | 2/2022 | Pierpoint |
| 2022/0039995 A1 | 2/2022 | Johannes et al. |
| 2022/0047410 A1 | 2/2022 | Walthall |
| 2022/0062027 A1 | 3/2022 | Mitchell et al. |
| 2022/0062028 A1 | 3/2022 | Mitchell et al. |
| 2022/0062029 A1 | 3/2022 | Johannes et al. |
| 2022/0066825 A1 | 3/2022 | Saraf et al. |
| 2022/0071811 A1 | 3/2022 | Cheng et al. |
| 2022/0071826 A1 | 3/2022 | Kulkarni et al. |
| 2022/0104965 A1 | 4/2022 | Vaninetti et al. |
| 2022/0104976 A1 | 4/2022 | Hoeger et al. |
| 2022/0104981 A1 | 4/2022 | Jones |
| 2022/0117773 A1 | 4/2022 | Davis et al. |
| 2022/0117774 A1 | 4/2022 | Meyer et al. |
| 2022/0117775 A1 | 4/2022 | Jones et al. |
| 2022/0133524 A1 | 5/2022 | Davis |
| 2022/0151817 A1 | 5/2022 | Mann |
| 2022/0160949 A1 | 5/2022 | Simiele et al. |
| 2022/0168159 A1 | 6/2022 | Triado et al. |
| 2022/0193312 A1 | 6/2022 | Lee et al. |
| 2022/0211536 A1 | 7/2022 | Johannes et al. |
| 2022/0218510 A1 | 7/2022 | Metzger et al. |
| 2022/0229053 A1 | 7/2022 | Levin et al. |
| 2022/0241106 A1 | 8/2022 | Johannes et al. |
| 2022/0247407 A1 | 8/2022 | Yamamoto et al. |
| 2022/0248836 A1 | 8/2022 | Cagle et al. |
| 2022/0257407 A1 | 8/2022 | Johannes et al. |
| 2022/0265460 A1 | 8/2022 | Coker |
| 2022/0265462 A1 | 8/2022 | Alder et al. |
| 2022/0270711 A1 | 8/2022 | Feala et al. |
| 2022/0273482 A1 | 9/2022 | Johannes et al. |
| 2022/0280357 A1 | 9/2022 | Jagannathan et al. |
| 2022/0287689 A1 | 9/2022 | Johannes |
| 2022/0296408 A1 | 9/2022 | Evans et al. |
| 2022/0305191 A1 | 9/2022 | Joseph et al. |
| 2022/0313222 A1 | 10/2022 | Austermann et al. |
| 2022/0313474 A1 | 10/2022 | Kriscovich et al. |
| 2022/0331170 A1 | 10/2022 | Erdem et al. |
| 2022/0339024 A1 | 10/2022 | Johannes et al. |
| 2022/0354685 A1 | 11/2022 | Davis et al. |
| 2022/0362049 A1 | 11/2022 | Austermann et al. |
| 2022/0370231 A1 | 11/2022 | Wang et al. |
| 2022/0370234 A1 | 11/2022 | Hughett et al. |
| 2022/0370235 A1 | 11/2022 | Johannes et al. |
| 2022/0370237 A1 | 11/2022 | Parmar et al. |
| 2022/0387001 A1 | 12/2022 | Askenazi et al. |
| 2022/0395390 A1 | 12/2022 | Brooks |
| 2022/0395391 A1 | 12/2022 | Saunders et al. |
| 2023/0018845 A1 | 1/2023 | Lee |
| 2023/0020563 A1 | 1/2023 | Sharma et al. |
| 2023/0031640 A1 | 2/2023 | Hughett et al. |
| 2023/0037159 A1 | 2/2023 | Brennan et al. |
| 2023/0052238 A1 | 2/2023 | Oluwasogo |
| 2023/0062994 A1 | 3/2023 | Ecklund et al. |
| 2023/0070347 A1 | 3/2023 | Watson et al. |
| 2023/0073708 A1 | 3/2023 | Xu et al. |
| 2023/0089032 A1 | 3/2023 | Hughett et al. |
| 2023/0099821 A1 | 3/2023 | Radl et al. |
| 2023/0099991 A1 | 3/2023 | Bianchi et al. |
| 2023/0105001 A1 | 4/2023 | Whittome et al. |
| 2023/0110577 A1 | 4/2023 | Choi |
| 2023/0138269 A1 | 5/2023 | Abdelal et al. |
| 2023/0145365 A1 | 5/2023 | Martin et al. |
| 2023/0155253 A1 | 5/2023 | Mn et al. |
| 2023/0210504 A1 | 7/2023 | Kuroda et al. |
| 2023/0210685 A1 | 7/2023 | Fallows et al. |
| 2023/0218426 A1 | 7/2023 | Hughett |
| 2023/0240884 A1 | 8/2023 | Davis et al. |
| 2023/0248562 A1 | 8/2023 | Sanchez et al. |
| 2023/0248564 A1 | 8/2023 | Mann et al. |
| 2023/0255812 A1 | 8/2023 | Sanchez et al. |
| 2023/0255813 A1 | 8/2023 | Sanchez et al. |
| 2023/0255815 A1 | 8/2023 | Newton |
| 2023/0263650 A1 | 8/2023 | Sanchez et al. |
| 2023/0263655 A1 | 8/2023 | Johannes et al. |
| 2023/0277362 A1 | 9/2023 | Davis et al. |
| 2023/0285178 A1 | 9/2023 | Sanchez et al. |
| 2023/0293339 A1 | 9/2023 | James |
| 2023/0301846 A1 | 9/2023 | Greenwood |
| 2023/0355423 A1 | 11/2023 | Stevenson et al. |
| 2023/0404791 A1 | 12/2023 | Ecklund et al. |
| 2024/0008444 A1 | 1/2024 | Su et al. |
| 2024/0009023 A1 | 1/2024 | Johannes et al. |
| 2024/0024170 A1 | 1/2024 | Scott |
| 2024/0041638 A1 | 2/2024 | Johannes et al. |
| 2024/0058161 A1 | 2/2024 | Ulreich et al. |
| 2024/0065881 A1 | 2/2024 | Kuroda et al. |
| 2024/0099874 A1 | 3/2024 | Sanchez et al. |
| 2024/0110318 A1 | 4/2024 | Bendt et al. |
| 2024/0123134 A1 | 4/2024 | Kharkar et al. |

FOREIGN PATENT DOCUMENTS

| | | |
|---|---|---|
| CA | 2165286 C | 9/1999 |
| CA | 2354132 A1 | 6/2000 |
| CA | 2359091 C | 9/2003 |
| CA | 2488867 C | 8/2007 |
| CA | 3050918 A1 | 8/2018 |
| CA | 3098571 A1 | 11/2019 |
| CN | 2269203 Y | 12/1997 |
| CN | 1332620 A | 1/2002 |
| CN | 1434693 A | 8/2003 |
| CN | 1533755 A | 10/2004 |
| CN | 1602825 A | 4/2005 |
| CN | 1720888 A | 1/2006 |
| CN | 2936204 Y | 8/2007 |
| CN | 101262836 A | 9/2008 |
| CN | 101522148 A | 9/2009 |
| CN | 102159159 A | 8/2011 |
| CN | 202184840 U | 4/2012 |
| CN | 102481441 A | 5/2012 |
| CN | 202463712 U | 10/2012 |
| CN | 103533968 A | 1/2014 |
| CN | 103717180 A | 4/2014 |
| CN | 204562697 U | 8/2015 |
| CN | 105411783 A | 3/2016 |
| CN | 105451693 A | 3/2016 |
| CN | 105534632 A | 5/2016 |
| CN | 205849719 U | 1/2017 |
| CN | 106726089 A | 5/2017 |
| CN | 107847384 A | 3/2018 |
| CN | 107920912 A | 4/2018 |
| CN | 108420590 A | 8/2018 |
| CN | 209285902 U | 8/2019 |
| CN | 110381883 A | 10/2019 |
| CN | 211198839 U | 8/2020 |
| CN | 112566550 A | 3/2021 |
| CN | 112603184 A | 4/2021 |
| CN | 114007493 A | 2/2022 |
| CN | 114375187 A | 4/2022 |
| CN | 116096332 A | 5/2023 |
| DE | 79818 C | 10/1893 |
| DE | 1516466 A1 | 6/1969 |
| DE | 2721330 A1 | 11/1977 |
| DE | 2742298 A1 | 3/1978 |
| DE | 9407554.9 U1 | 5/1995 |
| DE | 4443710 A1 | 6/1995 |
| DE | 4416094 A1 | 11/1995 |
| DE | 4236097 C2 | 10/1996 |
| DE | 19619597 A1 | 11/1997 |
| DE | 102005037762 B3 | 9/2006 |
| DE | 102011103783 A1 | 12/2012 |
| DE | 202015104597 U1 | 7/2016 |
| DE | 102020121462 B3 | 1/2022 |
| DK | 9600118 | 11/1996 |
| EP | 0032138 A2 | 7/1981 |
| EP | 0066070 B1 | 12/1982 |
| EP | 0068712 A1 | 1/1983 |
| EP | 0140470 A1 | 5/1985 |
| EP | 0140471 B1 | 5/1988 |
| EP | 0274753 A2 | 7/1988 |
| EP | 0119143 B1 | 11/1988 |
| EP | 0483592 A1 | 5/1992 |
| EP | 0610638 A1 | 8/1994 |

(56) References Cited

FOREIGN PATENT DOCUMENTS

| | | |
|---|---|---|
| EP | 0613355 A1 | 9/1994 |
| EP | 0613355 B1 | 1/1997 |
| EP | 0787472 A1 | 8/1997 |
| EP | 0966936 A1 | 12/1999 |
| EP | 0987293 A1 | 3/2000 |
| EP | 1063953 A1 | 1/2001 |
| EP | 0653928 B1 | 10/2002 |
| EP | 1332738 A1 | 8/2003 |
| EP | 1382318 A1 | 1/2004 |
| EP | 1089684 B1 | 10/2004 |
| EP | 1616542 A1 | 1/2006 |
| EP | 1382318 B1 | 5/2006 |
| EP | 1063953 B1 | 1/2007 |
| EP | 1872752 A1 | 1/2008 |
| EP | 2180907 A1 | 5/2010 |
| EP | 2380532 A1 | 10/2011 |
| EP | 2389908 A1 | 11/2011 |
| EP | 2601916 A1 | 6/2013 |
| EP | 2676643 A1 | 12/2013 |
| EP | 2997950 A2 | 3/2016 |
| EP | 2879534 B1 | 3/2017 |
| EP | 3424471 A1 | 1/2019 |
| EP | 3169292 B1 | 11/2019 |
| EP | 3753492 A1 | 12/2020 |
| EP | 3788992 A1 | 3/2021 |
| EP | 3576689 B1 | 3/2022 |
| EP | 3752110 B1 | 3/2022 |
| EP | 3787570 B1 | 3/2022 |
| EP | 4025163 A1 | 7/2022 |
| EP | 3463180 B1 | 3/2023 |
| EP | 3569205 B1 | 6/2023 |
| EP | 4382082 A2 | 6/2024 |
| GB | 871820 A | 7/1961 |
| GB | 1011517 A | 12/1965 |
| GB | 1467144 A | 3/1977 |
| GB | 2106395 A | 4/1983 |
| GB | 2106784 A | 4/1983 |
| GB | 2148126 A | 5/1985 |
| GB | 2171315 A | 8/1986 |
| GB | 2181953 A | 5/1987 |
| GB | 2148126 B | 7/1987 |
| GB | 2191095 A | 12/1987 |
| GB | 2199750 A | 7/1988 |
| GB | 2260907 A | 5/1993 |
| GB | 2462267 A | 2/2010 |
| GB | 2469496 A | 10/2010 |
| GB | 2490327 A | 10/2012 |
| GB | 2507318 A | 4/2014 |
| GB | 2612752 A | 5/2023 |
| IT | 201800009129 A1 | 4/2020 |
| JP | S498638 U | 1/1974 |
| JP | S5410596 A | 1/1979 |
| JP | S5410596 Y2 | 5/1979 |
| JP | S55155618 A | 12/1980 |
| JP | S5888596 U | 6/1983 |
| JP | S63107780 U | 7/1988 |
| JP | H0267530 A | 3/1990 |
| JP | H02103871 A | 4/1990 |
| JP | H02131422 A | 5/1990 |
| JP | H02131422 U | 11/1990 |
| JP | H0460220 A | 2/1992 |
| JP | H05123349 A | 5/1993 |
| JP | H05123350 A | 5/1993 |
| JP | 3087938 B2 | 10/1995 |
| JP | H085630 A | 1/1996 |
| JP | H1040141 A | 2/1998 |
| JP | H10225430 A | 8/1998 |
| JP | H11113946 A | 4/1999 |
| JP | H11290365 A | 10/1999 |
| JP | 2000116690 A | 4/2000 |
| JP | 2000185068 A | 7/2000 |
| JP | 2001054531 A | 2/2001 |
| JP | 2001070331 A | 3/2001 |
| JP | 2001224616 A | 8/2001 |
| JP | 2001276107 A | 10/2001 |
| JP | 2001276108 A | 10/2001 |
| JP | 2002028173 A | 1/2002 |
| JP | 2003505152 A | 2/2003 |
| JP | 2003126242 A | 5/2003 |
| JP | 2003180722 A | 7/2003 |
| JP | 2003528691 A | 9/2003 |
| JP | 2004057578 A | 2/2004 |
| JP | 2004130056 A | 4/2004 |
| JP | 2004267530 A | 9/2004 |
| JP | 2005052219 A | 3/2005 |
| JP | 2005066011 A | 3/2005 |
| JP | 2005066325 A | 3/2005 |
| JP | 2005102978 A | 4/2005 |
| JP | 2005518237 A | 6/2005 |
| JP | 3749097 B2 | 12/2005 |
| JP | 2006026108 A | 2/2006 |
| JP | 3123547 B2 | 6/2006 |
| JP | 2006136492 A | 6/2006 |
| JP | 2006204868 A | 8/2006 |
| JP | 2007044494 A | 2/2007 |
| JP | 3132659 B2 | 5/2007 |
| JP | 2007209687 A | 8/2007 |
| JP | 4039641 B2 | 11/2007 |
| JP | 2008005975 A | 1/2008 |
| JP | 2009509570 A | 3/2009 |
| JP | 2009165887 A | 7/2009 |
| JP | 2010504150 A | 2/2010 |
| JP | 2010081981 A | 4/2010 |
| JP | 4640772 B2 | 12/2010 |
| JP | 2010536439 A | 12/2010 |
| JP | 2011500225 A | 1/2011 |
| JP | 2011030962 A | 2/2011 |
| JP | 4747166 B2 | 5/2011 |
| JP | 2011087823 A | 5/2011 |
| JP | 4801218 B1 | 8/2011 |
| JP | 2011218130 A | 11/2011 |
| JP | 2011224070 A | 11/2011 |
| JP | 3175719 U | 4/2012 |
| JP | 2012523869 A | 10/2012 |
| JP | 2013238608 A | 11/2013 |
| JP | 2014521960 A | 8/2014 |
| JP | 2015092945 A | 5/2015 |
| JP | 3198994 B2 | 7/2015 |
| JP | 2016521191 A | 7/2016 |
| JP | 2017014698 A | 1/2017 |
| JP | 2019525811 A | 9/2019 |
| JP | 2019170942 A | 10/2019 |
| JP | 2019533492 A | 11/2019 |
| JP | 2021120686 A | 8/2021 |
| JP | 2021522009 A | 8/2021 |
| JP | 2021522013 A | 8/2021 |
| JP | 7129493 B2 | 8/2022 |
| JP | 2023532132 A | 7/2023 |
| KR | 200290061 Y1 | 9/2002 |
| KR | 20030047451 A | 6/2003 |
| KR | 20140039485 A | 4/2014 |
| KR | 101432639 B1 | 8/2014 |
| KR | 20180106659 A | 10/2018 |
| KR | 20180108774 A | 10/2018 |
| PT | 2068717 E | 6/2013 |
| SE | 505542 C2 | 9/1997 |
| WO | 8101957 A1 | 7/1981 |
| WO | 8804558 A1 | 6/1988 |
| WO | 9104714 A2 | 4/1991 |
| WO | 9104714 A3 | 6/1991 |
| WO | 9220299 A3 | 2/1993 |
| WO | 9307839 A1 | 4/1993 |
| WO | 9309736 A2 | 5/1993 |
| WO | 9309736 A3 | 6/1993 |
| WO | 9514448 A2 | 6/1995 |
| WO | 9600096 A1 | 1/1996 |
| WO | 9634636 A1 | 11/1996 |
| WO | 9817211 A1 | 4/1998 |
| WO | 9830336 A1 | 7/1998 |
| WO | 0000112 A1 | 1/2000 |
| WO | 0000113 A1 | 1/2000 |
| WO | 0025651 A1 | 5/2000 |
| WO | 0033773 A1 | 6/2000 |
| WO | 0057784 A1 | 10/2000 |

(56) References Cited

FOREIGN PATENT DOCUMENTS

| | | |
|---|---|---|
| WO | 0069377 A1 | 11/2000 |
| WO | 0079497 A1 | 12/2000 |
| WO | 0145618 A1 | 6/2001 |
| WO | 0145621 A1 | 6/2001 |
| WO | 02094160 A1 | 11/2002 |
| WO | 03013967 A1 | 2/2003 |
| WO | 03024824 A1 | 3/2003 |
| WO | 03055423 A1 | 7/2003 |
| WO | 03071931 A2 | 9/2003 |
| WO | 03079942 A1 | 10/2003 |
| WO | 03071931 A3 | 2/2004 |
| WO | 2004019836 A1 | 3/2004 |
| WO | 2004024046 A1 | 3/2004 |
| WO | 2004026195 A1 | 4/2004 |
| WO | 2005051252 A1 | 6/2005 |
| WO | 2005074571 A3 | 9/2005 |
| WO | 2005089687 A2 | 9/2005 |
| WO | 2005107661 A2 | 11/2005 |
| WO | 2006021220 A1 | 3/2006 |
| WO | 2006037140 A2 | 4/2006 |
| WO | 2007005851 A2 | 1/2007 |
| WO | 2007007845 A1 | 1/2007 |
| WO | 2007042823 A2 | 4/2007 |
| WO | 2007055651 A1 | 5/2007 |
| WO | 2006098950 A3 | 11/2007 |
| WO | 2007134608 A2 | 11/2007 |
| WO | 2007128156 A3 | 2/2008 |
| WO | 2008026106 A2 | 3/2008 |
| WO | 2008078117 A1 | 7/2008 |
| WO | 2008104019 A1 | 9/2008 |
| WO | 2008141471 A1 | 11/2008 |
| WO | 2009004368 A1 | 1/2009 |
| WO | 2009004369 A1 | 1/2009 |
| WO | 2009052496 A1 | 4/2009 |
| WO | 2009052502 A1 | 4/2009 |
| WO | 2009007702 A4 | 7/2009 |
| WO | 2009101738 A1 | 8/2009 |
| WO | 2010058192 A1 | 5/2010 |
| WO | 2010030122 A3 | 7/2010 |
| WO | 2010101915 A3 | 1/2011 |
| WO | 2011018132 A1 | 2/2011 |
| WO | 2011018133 A1 | 2/2011 |
| WO | 2011024864 A1 | 3/2011 |
| WO | 2011054118 A1 | 5/2011 |
| WO | 2011079132 A1 | 6/2011 |
| WO | 2011107972 A1 | 9/2011 |
| WO | 2011108972 A1 | 9/2011 |
| WO | 2011117292 A1 | 9/2011 |
| WO | 2011123219 A1 | 10/2011 |
| WO | 2011132043 A1 | 10/2011 |
| WO | 2012012908 A1 | 2/2012 |
| WO | 2012065274 A1 | 5/2012 |
| WO | 2012097462 A1 | 7/2012 |
| WO | 2012098796 A1 | 7/2012 |
| WO | 2012101288 A1 | 8/2012 |
| WO | 2012175916 A1 | 12/2012 |
| WO | 2013018435 A1 | 2/2013 |
| WO | 2013033429 A1 | 3/2013 |
| WO | 2013055434 A1 | 4/2013 |
| WO | 2013082397 A1 | 6/2013 |
| WO | 2013103291 A2 | 7/2013 |
| WO | 2013131109 A1 | 9/2013 |
| WO | 2013167478 A1 | 11/2013 |
| WO | 2013177716 A1 | 12/2013 |
| WO | 2014041534 A1 | 3/2014 |
| WO | 2014046420 A1 | 3/2014 |
| WO | 2014118518 A1 | 8/2014 |
| WO | 2014160852 A1 | 10/2014 |
| WO | 2015023599 A1 | 2/2015 |
| WO | 2015052348 A1 | 4/2015 |
| WO | 2015068384 A1 | 5/2015 |
| WO | 2015169403 A1 | 11/2015 |
| WO | 2015170307 A1 | 11/2015 |
| WO | 2015197462 A1 | 12/2015 |
| WO | 2016051385 A1 | 4/2016 |
| WO | 2016055989 A1 | 4/2016 |
| WO | 2016071894 A1 | 5/2016 |
| WO | 2016103242 A1 | 6/2016 |
| WO | 2016116915 A1 | 7/2016 |
| WO | 2016124203 A1 | 8/2016 |
| WO | 2016139448 A1 | 9/2016 |
| WO | 2016166562 A1 | 10/2016 |
| WO | 2016167535 A1 | 10/2016 |
| WO | 2016191574 A1 | 12/2016 |
| WO | 2016200088 A1 | 12/2016 |
| WO | 2016200361 A1 | 12/2016 |
| WO | 2016204731 A1 | 12/2016 |
| WO | 2017001532 A2 | 1/2017 |
| WO | 2017001846 A1 | 1/2017 |
| WO | 2017075226 A1 | 5/2017 |
| WO | 2017152198 A1 | 9/2017 |
| WO | 2017153357 A1 | 9/2017 |
| WO | 2017162559 A1 | 9/2017 |
| WO | 2017205446 A1 | 11/2017 |
| WO | 2017209779 A1 | 12/2017 |
| WO | 2017210524 A1 | 12/2017 |
| WO | 2018022414 A1 | 2/2018 |
| WO | 2018044781 A1 | 3/2018 |
| WO | 2018056953 A1 | 3/2018 |
| WO | 2018090550 A1 | 5/2018 |
| WO | 2018138513 A1 | 8/2018 |
| WO | 2018144318 A1 | 8/2018 |
| WO | 2018144463 A1 | 8/2018 |
| WO | 2018150263 A1 | 8/2018 |
| WO | 2018150268 A1 | 8/2018 |
| WO | 2018152156 A1 | 8/2018 |
| WO | 2018183791 A1 | 10/2018 |
| WO | 2018150267 A3 | 11/2018 |
| WO | 2018235026 A1 | 12/2018 |
| WO | 2018235065 A1 | 12/2018 |
| WO | 2019004404 A1 | 1/2019 |
| WO | 2019041005 A1 | 3/2019 |
| WO | 2019044217 A1 | 3/2019 |
| WO | 2019044218 A1 | 3/2019 |
| WO | 2019044219 A1 | 3/2019 |
| WO | 2019050959 A1 | 3/2019 |
| WO | 2019065541 A1 | 4/2019 |
| WO | 2019096845 A1 | 5/2019 |
| WO | 2019150385 A1 | 8/2019 |
| WO | 2019161094 A1 | 8/2019 |
| WO | 2019188566 A1 | 10/2019 |
| WO | 2019190593 A1 | 10/2019 |
| WO | 2019212949 A1 | 11/2019 |
| WO | 2019212950 A1 | 11/2019 |
| WO | 2019212951 A1 | 11/2019 |
| WO | 2019212952 A1 | 11/2019 |
| WO | 2019212954 A1 | 11/2019 |
| WO | 2019212955 A1 | 11/2019 |
| WO | 2019212956 A1 | 11/2019 |
| WO | 2019214787 A1 | 11/2019 |
| WO | 2019214788 A1 | 11/2019 |
| WO | 2019226826 A1 | 11/2019 |
| WO | 2019239433 A1 | 12/2019 |
| WO | 2020000994 A1 | 1/2020 |
| WO | 2020020618 A1 | 1/2020 |
| WO | 2020038822 A1 | 2/2020 |
| WO | 2020088409 A1 | 5/2020 |
| WO | 2020049394 A3 | 6/2020 |
| WO | 2020120657 A1 | 6/2020 |
| WO | 2020152575 A1 | 7/2020 |
| WO | 2020182923 A1 | 9/2020 |
| WO | 2020204967 A1 | 10/2020 |
| WO | 2020205939 A1 | 10/2020 |
| WO | 2020209898 A1 | 10/2020 |
| WO | 2020242790 A1 | 12/2020 |
| WO | 2020251893 A1 | 12/2020 |
| WO | 2020256865 A1 | 12/2020 |
| WO | 2021007144 A1 | 1/2021 |
| WO | 2021007345 A1 | 1/2021 |
| WO | 2021010844 A1 | 1/2021 |
| WO | 2021016026 A1 | 1/2021 |
| WO | 2021016300 A1 | 1/2021 |
| WO | 2021025919 A1 | 2/2021 |
| WO | 2021034886 A1 | 2/2021 |

(56) References Cited

FOREIGN PATENT DOCUMENTS

| | | | |
|---|---|---|---|
| WO | 2021041123 | A1 | 3/2021 |
| WO | 2021046501 | A1 | 3/2021 |
| WO | 2021086868 | A1 | 5/2021 |
| WO | 2021094352 | A1 | 5/2021 |
| WO | 2021094639 | A1 | 5/2021 |
| WO | 2021097067 | A1 | 5/2021 |
| WO | 2021102296 | A1 | 5/2021 |
| WO | 2021107025 | A1 | 6/2021 |
| WO | 2021138411 | A1 | 7/2021 |
| WO | 2021138414 | A1 | 7/2021 |
| WO | 2021154686 | A1 | 8/2021 |
| WO | 2021155206 | A1 | 8/2021 |
| WO | 2021170075 | A1 | 9/2021 |
| WO | 2021173436 | A1 | 9/2021 |
| WO | 2021188817 | A1 | 9/2021 |
| WO | 2021195384 | A1 | 9/2021 |
| WO | 2021205995 | A1 | 10/2021 |
| WO | 2021207621 | A1 | 10/2021 |
| WO | 2021211568 | A1 | 10/2021 |
| WO | 2021211801 | A1 | 10/2021 |
| WO | 2021211914 | A1 | 10/2021 |
| WO | 2021216419 | A1 | 10/2021 |
| WO | 2021216422 | A1 | 10/2021 |
| WO | 2021231532 | A1 | 11/2021 |
| WO | 2021247523 | A1 | 12/2021 |
| WO | 2021257202 | A1 | 12/2021 |
| WO | 2022006256 | A1 | 1/2022 |
| WO | 2022031943 | A1 | 2/2022 |
| WO | 2022035745 | A1 | 2/2022 |
| WO | 2022051360 | A1 | 3/2022 |
| WO | 2022054613 | A1 | 3/2022 |
| WO | 2022066704 | A1 | 3/2022 |
| WO | 2022067392 | A1 | 4/2022 |
| WO | 2022069950 | A1 | 4/2022 |
| WO | 2022071429 | A1 | 4/2022 |
| WO | 2022076322 | A1 | 4/2022 |
| WO | 2022076427 | A2 | 4/2022 |
| WO | 2022086898 | A1 | 4/2022 |
| WO | 2022090199 | A1 | 5/2022 |
| WO | 2022098536 | A1 | 5/2022 |
| WO | 2022099087 | A1 | 5/2022 |
| WO | 2022101999 | A1 | 5/2022 |
| WO | 2022115692 | A1 | 6/2022 |
| WO | 2022125685 | A1 | 6/2022 |
| WO | 2022140545 | A1 | 6/2022 |
| WO | 2022145231 | A1 | 7/2022 |
| WO | 2022150360 | A1 | 7/2022 |
| WO | 2022150463 | A1 | 7/2022 |
| WO | 2022159392 | A1 | 7/2022 |
| WO | 2022170182 | A1 | 8/2022 |
| WO | 2022182385 | A1 | 9/2022 |
| WO | 2022187152 | A1 | 9/2022 |
| WO | 2022192188 | A1 | 9/2022 |
| WO | 2022192347 | A1 | 9/2022 |
| WO | 2022204000 | A1 | 9/2022 |
| WO | 2022216507 | A1 | 10/2022 |
| WO | 2022222030 | A1 | 10/2022 |
| WO | 2023286058 | A1 | 1/2023 |
| WO | 2023014639 | A1 | 2/2023 |
| WO | 2023014641 | A1 | 2/2023 |
| WO | 2023018475 | A2 | 2/2023 |
| WO | 2023023777 | A1 | 3/2023 |
| WO | 2023034453 | A1 | 3/2023 |
| WO | 2023038945 | A1 | 3/2023 |
| WO | 2023038950 | A1 | 3/2023 |
| WO | 2023049109 | A1 | 3/2023 |
| WO | 2023049175 | A1 | 3/2023 |
| WO | 2023086394 | A1 | 5/2023 |
| WO | 2023149884 | A1 | 8/2023 |
| WO | 2023149902 | A1 | 8/2023 |
| WO | 2023149903 | A1 | 8/2023 |
| WO | 2023154390 | A1 | 8/2023 |
| WO | 2023191764 | A1 | 10/2023 |
| WO | 2023244238 | A1 | 12/2023 |
| WO | 2024058788 | A1 | 3/2024 |

OTHER PUBLICATIONS

U.S. Appl. No. 17/662,700, filed May 10, 2022.
U.S. Appl. No. 63/008,112, filed Apr. 10, 2020.
Advisory Action for U.S. Appl. No. 14/722,613 mailed Mar. 4, 2019.
Advisory Action for U.S. Appl. No. 14/952,591 mailed Jun. 1, 2018.
Advisory Action for U.S. Appl. No. 15/238,427 mailed Apr. 10, 2019.
Advisory Action for U.S. Appl. No. 16/899,956 mailed Jul. 9, 2021.
Advisory Action for U.S. Appl. No. 16/904,868 mailed Jul. 2, 2021.
Advisory Action for U.S. Appl. No. 16/905,400 mailed Feb. 16, 2022.
Advisory Action for U.S. Appl. No. 16/905,400 mailed Jun. 9, 2021.
Corrected International Search Report and Written Opinion for International Application No. PCT/US2017/043025 mailed Jan. 11, 2018.
Corrected Notice of Allowability for U.S. Appl. No. 15/221,106 mailed Jul. 2, 2019.
Corrected Notice of Allowability for U.S. Appl. No. 15/612,325 mailed Mar. 17, 2021.
Corrected Notice of Allowability for U.S. Appl. No. 17/330,657 mailed Dec. 9, 2021.
Final Office Action for U.S. Appl. No. 14/722,613 mailed on Nov. 29, 2018.
Final Office Action for U.S. Appl. No. 14/947,759 mailed Apr. 8, 2016.
Final Office Action for U.S. Appl. No. 14/952,591 mailed Feb. 23, 2018.
Final Office Action for U.S. Appl. No. 14/952,591 mailed Nov. 1, 2019.
Final Office Action for U.S. Appl. No. 14/952,591 mailed Nov. 27, 2020.
Final Office Action for U.S. Appl. No. 15/171,968 mailed Feb. 14, 2020.
Final Office Action for U.S. Appl. No. 15/171,968 mailed Mar. 19, 2019.
Final Office Action for U.S. Appl. No. 15/221,106 mailed Jan. 23, 2019.
Final Office Action for U.S. Appl. No. 15/238,427 mailed Jan. 2, 2019.
Final Office Action for U.S. Appl. No. 15/260,103 mailed Feb. 14, 2019.
Final Office Action for U.S. Appl. No. 15/612,325 mailed Sep. 17, 2020.
Final Office Action for U.S. Appl. No. 16/452,145 mailed Mar. 25, 2022.
Final Office Action for U.S. Appl. No. 16/899,956 mailed Apr. 19, 2021.
Final Office Action for U.S. Appl. No. 16/904,868 mailed Mar. 10, 2022.
Final Office Action for U.S. Appl. No. 16/904,868 mailed Mar. 26, 2021.
Final Office Action for U.S. Appl. No. 16/905,400 mailed Apr. 6, 2021.
Final Office Action for U.S. Appl. No. 16/905,400 mailed Dec. 9, 2021.
Final Office Action for U.S. Appl. No. 17/088,272 mailed May 25, 2021.
Final Office Action for U.S. Appl. No. 29/624,661 mailed Feb. 18, 2020.
International Search Report and Written Opinion from International Application No. PCT/US2016/049274 mailed Dec. 1, 2016.
International Search Report and Written Opinion from International Application No. PCT/US2017/035625 mailed Aug. 15, 2017.
International Search Report and Written Opinion from International Application No. PCT/US2017/043025 mailed Oct. 18, 2017.
International Search Report and Written Opinion from International Application No. PCT/US2018/015968 mailed Apr. 6, 2018.
International Search Report and Written Opinion from International Application No. PCT/US2019/029608 mailed Sep. 3, 2019.
International Search Report and Written Opinion from International Application No. PCT/US2019/029609 mailed Sep. 3, 2019.

(56) References Cited

OTHER PUBLICATIONS

International Search Report and Written Opinion from International Application No. PCT/US2019/029610 mailed Sep. 3, 2019.
International Search Report and Written Opinion from International Application No. PCT/US2019/029611 mailed Jul. 3, 2019.
International Search Report and Written Opinion from International Application No. PCT/US2019/029613 mailed Jul. 3, 2019.
International Search Report and Written Opinion from International Application No. PCT/US2019/029614 mailed Sep. 26, 2019.
International Search Report and Written Opinion from International Application No. PCT/US2019/029616 mailed Aug. 30, 2019.
International Search Report and Written Opinion from International Application No. PCT/US2020/023572 mailed Jul. 6, 2020.
International Search Report and Written Opinion from International Application No. PCT/US2020/033064 mailed Aug. 31, 2020.
International Search Report and Written Opinion from International Application No. PCT/US2020/033122 mailed Aug. 31, 2020.
International Search Report and Written Opinion from International Application No. PCT/US2020/040860 mailed Oct. 2, 2020.
International Search Report and Written Opinion from International Application No. PCT/US2020/041242 mailed Nov. 17, 2020.
International Search Report and Written Opinion from International Application No. PCT/US2020/041249 mailed Oct. 2, 2020.
International Search Report and Written Opinion from International Application No. PCT/US2020/042262 mailed Oct. 14, 2020.
International Search Report and Written Opinion from International Application No. PCT/US2020/043059 mailed Oct. 6, 2020.
International Search Report and Written Opinion from International Application No. PCT/US2020/044024 mailed Nov. 12, 2020.
International Search Report and Written Opinion from International Application No. PCT/US2020/046914 mailed Dec. 1, 2020.
International Search Report and Written Opinion from International Application No. PCT/US2020/055680 mailed Dec. 15, 2020.
International Search Report and Written Opinion from International Application No. PCT/US2020/057562 mailed Jan. 27, 2021.
International Search Report and Written Opinion from International Application No. PCT/US2020/061563 mailed Feb. 19, 2021.
International Search Report and Written Opinion from International Application No. PCT/US2020/065234 mailed Apr. 12, 2021.
International Search Report and Written Opinion from International Application No. PCT/US2020/067451 mailed Mar. 25, 2021.
International Search Report and Written Opinion from International Application No. PCT/US2020/067454 mailed Mar. 29, 2021.
International Search Report and Written Opinion from International Application No. PCT/US2020/067455 mailed Mar. 26, 2021.
International Search Report and Written Opinion from International Application No. PCT/US2021/015024 mailed May 18, 2021.
International Search Report and Written Opinion from International Application No. PCT/US2021/015787 mailed May 27, 2021.
International Search Report and Written Opinion from International Application No. PCT/US2021/023001 mailed Jun. 21, 2021.
International Search Report and Written Opinion from International Application No. PCT/US2021/024162 mailed Jul. 8, 2021.
International Search Report and Written Opinion from International Application No. PCT/US2021/026607 mailed Jul. 29, 2021.
International Search Report and Written Opinion from International Application No. PCT/US2021/027061 mailed Jul. 19, 2021.
International Search Report and Written Opinion from International Application No. PCT/US2021/027104 mailed Jul. 6, 2021.
International Search Report and Written Opinion from International Application No. PCT/US2021/027314 mailed Jul. 6, 2021.
International Search Report and Written Opinion from International Application No. PCT/US2021/027422 mailed Aug. 12, 2021.
International Search Report and Written Opinion from International Application No. PCT/US2021/027425 mailed Aug. 11, 2021.
International Search Report and Written Opinion from International Application No. PCT/US2021/027913 mailed Jul. 12, 2021.
International Search Report and Written Opinion from International Application No. PCT/US2021/027917 mailed Aug. 19, 2021.
International Search Report and Written Opinion from International Application No. PCT/US2021/035181 mailed Sep. 16, 2021.
International Search Report and Written Opinion from International Application No. PCT/US2021/043893 mailed Nov. 22, 2021.
International Search Report and Written Opinion from International Application No. PCT/US2021/044699 mailed Nov. 22, 2021.
International Search Report and Written Opinion from International Application No. PCT/US2021/045188 mailed Jan. 26, 2022.
International Search Report and Written Opinion from International Application No. PCT/US2021/047536 mailed Dec. 23, 2021.
International Search Report and Written Opinion from International Application No. PCT/US2021/048211 mailed Dec. 22, 2021.
International Search Report and Written Opinion from International Application No. PCT/US2021/048661 mailed Feb. 14, 2022.
International Search Report and Written Opinion from International Application No. PCT/US2021/056566 mailed Feb. 11, 2022.
International Search Report and Written Opinion from International Application No. PCT/US2021/060993 mailed Mar. 18, 2022.
International Search Report and Written Opinion from International Application No. PCT/US2021/062440 mailed Mar. 28, 2022.
Issue Notification for U.S. Appl. No. 14/952,591 mailed Jul. 28, 2021.
Issue Notification for U.S. Appl. No. 15/171,968 mailed Mar. 3, 2021.
Issue Notification for U.S. Appl. No. 15/221,106 mailed Jul. 24, 2019.
Issue Notification for U.S. Appl. No. 15/238,427 mailed Jul. 24, 2019.
Issue Notification for U.S. Appl. No. 15/260,103 mailed Aug. 7, 2019.
Issue Notification for U.S. Appl. No. 15/611,587 mailed Feb. 20, 2019.
Issue Notification for U.S. Appl. No. 15/612,325 mailed Mar. 24, 2021.
Issue Notification for U.S. Appl. No. 29/624,661 mailed Aug. 4, 2021.
Non-Final Office Action for U.S. Appl. No. 14/592,591 mailed Mar. 20, 2020.
Non-Final Office Action for U.S. Appl. No. 14/722,613 mailed Jun. 13, 2019.
Non-Final Office Action for U.S. Appl. No. 14/947,759 mailed Mar. 17, 2016.
Non-Final Office Action for U.S. Appl. No. 14/952,591 mailed Aug. 1, 2017.
Non-Final Office Action for U.S. Appl. No. 14/952,591 mailed Mar. 20, 2020.
Non-Final Office Action for U.S. Appl. No. 14/952,591 mailed Mar. 21, 2019.
Non-Final Office Action for U.S. Appl. No. 14/952,591 mailed Sep. 28, 2018.
Non-Final Office Action for U.S. Appl. No. 15/171,968 mailed May 11, 2020.
Non-Final Office Action for U.S. Appl. No. 15/171,968 mailed Aug. 20, 2019.
Non-Final Office Action for U.S. Appl. No. 15/171,968 mailed Jun. 12, 2018.
Non-Final Office Action for U.S. Appl. No. 15/221,106 mailed Jun. 5, 2018.
Non-Final Office Action for U.S. Appl. No. 15/238,427 mailed Aug. 8, 2018.
Non-Final Office Action for U.S. Appl. No. 15/260,103 mailed Sep. 26, 2018.
Non-Final Office Action for U.S. Appl. No. 15/611,587 mailed Dec. 29, 2017.
Non-Final Office Action for U.S. Appl. No. 15/611,587 mailed Jul. 13, 2018.
Non-Final Office Action for U.S. Appl. No. 15/612,325 mailed Mar. 19, 2020.
Non-Final Office Action for U.S. Appl. No. 16/245,726 mailed Jan. 21, 2022.
Non-Final Office Action for U.S. Appl. No. 16/369,676 mailed Mar. 31, 2022.

(56) References Cited

OTHER PUBLICATIONS

Non-Final Office Action for U.S. Appl. No. 16/433,773 mailed Apr. 21, 2022.
Non-Final Office Action for U.S. Appl. No. 16/449,039 mailed Dec. 8, 2021.
Non-Final Office Action for U.S. Appl. No. 16/452,145 mailed Sep. 28, 2021.
Non-Final Office Action for U.S. Appl. No. 16/452,258 mailed Sep. 28, 2021.
Non-Final Office Action for U.S. Appl. No. 16/478,180 mailed Oct. 22, 2021.
Non-Final Office Action for U.S. Appl. No. 16/899,956 mailed Oct. 16, 2020.
Non-Final Office Action for U.S. Appl. No. 16/899,956 mailed Sep. 2, 2021.
Non-Final Office Action for U.S. Appl. No. 16/904,868 mailed Nov. 25, 2020.
Non-Final Office Action for U.S. Appl. No. 16/904,868 mailed Oct. 5, 2021.
Non-Final Office Action for U.S. Appl. No. 16/905,400 mailed Apr. 27, 2022.
Non-Final Office Action for U.S. Appl. No. 16/905,400 mailed Dec. 2, 2020.
Non-Final Office Action for U.S. Appl. No. 16/905,400 mailed Jul. 22, 2021.
Non-Final Office Action for U.S. Appl. No. 17/088,272 mailed Jan. 25, 2021.
Non-Final Office Action for U.S. Appl. No. 17/330,657 mailed Aug. 11, 2021.
Non-Final Office Action for U.S. Appl. No. 29/624,661 mailed Jul. 18, 2019.
Non-Final Office Action for U.S. Appl. No. 29/694,002 mailed Jun. 24, 2020.
Non-Final Office Action for U.S. Appl. No. 29/741,751 mailed Jan. 18, 2022.
Notice of Allowance for U.S. Appl. No. 14/952,591 mailed Apr. 5, 2021.
Notice of Allowance for U.S. Appl. No. 14/952,591 mailed Jul. 8, 2021.
Notice of Allowance for U.S. Appl. No. 15/171,968 mailed Feb. 16, 2021.
Notice of Allowance for U.S. Appl. No. 15/171,968 mailed Nov. 6, 2020.
Notice of Allowance for U.S. Appl. No. 15/221,106 mailed May 1, 2019.
Notice of Allowance for U.S. Appl. No. 15/238,427 mailed May 23, 2019.
Notice of Allowance for U.S. Appl. No. 15/260,103 mailed Jun. 7, 2019.
Notice of Allowance for U.S. Appl. No. 15/611,587 mailed Dec. 21, 2018.
Notice of Allowance for U.S. Appl. No. 15/612,325 mailed Feb. 19, 2021.
Notice of Allowance for U.S. Appl. No. 15/612,325 mailed Jan. 21, 2021.
Notice of Allowance for U.S. Appl. No. 16/899,956 mailed Apr. 19, 2022.
Notice of Allowance for U.S. Appl. No. 16/899,956 mailed Dec. 29, 2021.
Notice of Allowance for U.S. Appl. No. 17/088,272 mailed Aug. 5, 2021.
Notice of Allowance for U.S. Appl. No. 17/088,272 mailed Mar. 4, 2022.
Notice of Allowance for U.S. Appl. No. 17/088,272 mailed Nov. 24, 2021.
Notice of Allowance for U.S. Appl. No. 17/330,657 mailed Mar. 16, 2022.
Notice of Allowance for U.S. Appl. No. 17/330,657 mailed Nov. 26, 2021.
Notice of Allowance for U.S. Appl. No. 29/624,661 mailed Apr. 28, 2021.
Notice of Allowance for U.S. Appl. No. 29/624,661 mailed Jul. 10, 2020.
Notice of Allowance for U.S. Appl. No. 29/624,661 mailed May 14, 2020.
Notice of Allowance for U.S. Appl. No. 29/624,661 mailed Sep. 29, 2020.
Notice of Allowance for U.S. Appl. No. 29/694,002 mailed Apr. 29, 2021.
Notice of Allowance for U.S. Appl. No. 29/694,002 mailed Jan. 29, 2021.
Notice of Allowance for U.S. Appl. No. 29/694,002 mailed Oct. 16, 2020.
Notice to File Missing Parts for U.S. Appl. No. 17/179,116 mailed Mar. 3, 2021.
Restriction Requirement for U.S. Appl. No. 16/433,773 mailed Dec. 7, 2021.
Restriction Requirement for U.S. Appl. No. 16/478,180 mailed May 25, 2021.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/171,968, filed Jun. 2, 2016.
U.S. Appl. No. 15/221,106, filed Jul. 27, 2016.
U.S. Appl. No. 15/260,103, filed Sep. 8, 2016.
U.S. Appl. No. 15/384,196, filed Dec. 19, 2016.
U.S. Appl. No. 15/611,587, filed Jun. 1, 2017.
U.S. Appl. No. 15/612,325, filed Jun. 2, 2017.
U.S. Appl. No. 16/245,726, filed Jan. 11, 2019.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl, No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 17/179,116, filed Feb. 18, 2021.
U.S. Appl. No. 17/330,657, filed May 26, 2021.
U.S. Appl. No. 17/378,015, filed Jul. 16, 2021.
U.S. Appl. No. 17/394,055, filed Aug. 4, 2021.
U.S. Appl. No. 17/412,864, filed Aug. 26, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/450,864, filed Oct. 14, 2021.
U.S. Appl. No. 17/451,345, filed Oct. 19, 2021.
U.S. Appl. No. 17/451,354, filed Oct. 19, 2021.
U.S. Appl. No. 17/453,260, filed Nov. 2, 2021.
U.S. Appl. No. 17/453,560, filed Nov. 4, 2021.
U.S. Appl. No. 17/461,036 mailed Aug. 30, 2021.
U.S. Appl. No. 17/494,578, filed Oct. 5, 2021.
U.S. Appl. No. 17/501,591, filed Oct. 14, 2021.
U.S. Appl. No. 17/595,747, filed Nov. 23, 2021.
U.S. Appl. No. 17/597,408, filed Jan. 5, 2022.
U.S. Appl. No. 17/597,673, filed Jan. 18, 2022.
U.S. Appl. No. 17/614,173, filed Nov. 24, 2021.
U.S. Appl. No. 17/631,619, filed Jan. 31, 2022.
U.S. Appl. No. 17/645,821, filed Dec. 23, 2021.
U.S. Appl. No. 17/646,771, filed Jan. 3, 2022.
U.S. Appl. No. 17/653,314, filed Mar. 3, 2022.
U.S. Appl. No. 17/653,920, filed Mar. 8, 2022.
U.S. Appl. No. 17/654,156, filed Mar. 9, 2022.
U.S. Appl. No. 17/655,464, filed Mar. 18, 2022.
U.S. Appl. No. 17/657,474, filed Mar. 31, 2022.
U.S. Appl. No. 17/754,736, filed Apr. 11, 2022.

(56) References Cited

OTHER PUBLICATIONS

U.S. Appl. No. 29/741,751, filed Jul. 15, 2020.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/452,437, filed Jan. 31, 2017.
U.S. Appl. No. 62/485,578, filed Apr. 14, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,279, filed May 28, 2019.
U.S. Appl. No. 62/853,889, filed May 29, 2019.
U.S. Appl. No. 62/864,656, filed Jun. 21, 2019.
U.S. Appl. No. 62/873,045, filed Jul. 11, 2019.
U.S. Appl. No. 62/873,048, filed Jul. 11, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149, filed Aug. 20, 2019.
U.S. Appl. No. 62/923,279, filed Oct. 18, 2019.
U.S. Appl. No. 62/926,767, filed Oct. 28, 2019.
U.S. Appl. No. 62/935,337, filed Nov. 14, 2019.
U.S. Appl. No. 62/938,447, filed Nov. 21, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/967,977, filed Jan. 30, 2020.
U.S. Appl. No. 62/994,912, filed Mar. 26, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/030,685, filed May 27, 2020.
U.S. Appl. No. 63/033,310, filed Jun. 2, 2020.
U.S. Appl. No. 63/047,374, filed Jul. 2, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126, filed Aug. 11, 2020.
U.S. Appl. No. 63/067,542, filed Aug. 19, 2020.
U.S. Appl. No. 63/071,438, filed Aug. 28, 2020.
U.S. Appl. No. 63/071,821, filed Aug. 28, 2020.
U.S. Appl. No. 63/073,545, filed Sep. 2, 2020.
U.S. Appl. No. 63/073,553, filed Sep. 2, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/088,539, filed Oct. 7, 2020.
U.S. Appl. No. 63/094,464, filed Oct. 21, 2020.
U.S. Appl. No. 63/094,498, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/094,646, filed Oct. 21, 2020.
U.S. Appl. No. 63/109,066, filed Nov. 3, 2020.
U.S. Appl. No. 63/109,084, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/124,271, filed Dec. 11, 2020.
U.S. Appl. No. 63/133,892, filed Jan. 5, 2021.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.
U.S. Appl. No. 63/138,878, filed Jan. 19, 2021.
U.S. Appl. No. 63/146,946, filed Feb. 8, 2021.
U.S. Appl. No. 63/147,013, filed Feb. 8, 2021.
U.S. Appl. No. 63/147,299, filed Feb. 9, 2021.
U.S. Appl. No. 63/148,723, filed Feb. 12, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,186, filed Mar. 10, 2021.
U.S. Appl. No. 63/159,210, filed Mar. 10, 2021.
U.S. Appl. No. 63/159,280, filed Mar. 10, 2021.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/192,274, filed May 24, 2021.
U.S. Appl. No. 63/193,235, filed May 26, 2021.
U.S. Appl. No. 63/193,406, filed May 26, 2021.
U.S. Appl. No. 63/193,891, filed May 27, 2021.
U.S. Appl. No. 63/208,262, filed Jun. 8, 2021.
U.S. Appl. No. 63/214,551, filed Jun. 24, 2021.
U.S. Appl. No. 63/214,570, filed Jun. 24, 2021.
U.S. Appl. No. 63/215,017, filed Jun. 25, 2021.
U.S. Appl. No. 63/228,244, filed Aug. 2, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/230,897, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.
U.S. Appl. No. 63/299,208, filed Jan. 13, 2022.
Sage's Second Supplemental Invalidity Contentions Regarding U.S. Pat. Nos. 8,287,508, 10,226,375, 10,390,989, and U.S. Pat. No. 10,376,407, 292 pages.
Plaintiff's Identification of Claim Terms and Proposed Constructions, 3 pages.
Sage's Preliminary Identification of Claim Elements and Proposed Constructions for U.S. Pat. Nos. 8,287,508, 10,226,376, 10,390,989 and U.S. Pat. No. 10,376,407, 7 pages.
Corrected Certificate of Service, 2020, 2 pages.
Excerpts from the 508 (U.S. Pat. No. 8,278,508) Patent's Prosecution History, 2020, 99 pages.
Declaration of Diane K. Newman Curriculum Vitae, 2020, pp. 1-199.
Sage's Supplemental and Initial Invalidity Contentions Regarding U.S. Pat. Nos. 8,287,508; 10,226,375; 10,390,989 and Initial Invalidity Contentions Regarding U.S. Pat. No. 10,376,407, Aug. 21, 2020, 277 pages.
Decision Granting Institution of Inter Partes Review for U.S. Pat. No. 8,287,508, Feb. 17, 2021, 39 pages.
Memorandum Order, Feb. 2021, 14 pgs.
Boehringer CareDry System—Second Generation for Non-Invasive Urinary Management for Females, Mar. 2021, 3 pgs.

(56) References Cited

OTHER PUBLICATIONS

PureWick's Response to Interrogatory No. 9 in *PureWick, LLC* v. *Sage Products, LLC*, Mar. 23, 2020, 6 pages.
Sage's Initial Invalidity Contentions Regarding U.S. Pat. Nos. 8,287,508; 10,226,375; and U.S. Pat. No. 10,390,989, May 29, 2020, 193 pages.
Defendant and Counterclaim Plaintiff Sage Products, LLC's Answer, Defenses, and Counterclaims To Plaintiff's Amended Complaint, Nov. 1, 2019.
Plaintiff's Opening Claim Construction Brief, Oct. 16, 2020, 26 pages.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit Brochure", https://www.omnimedicalsys.com/index.php?page=products, 8 pages.
"AMXDmax In-Flight Bladder Relief", Omni Medical; Omni Medical Systems, Inc., 2015.
"AMXDX—Advanced Mission Extender Device Brochure", Omni Medical, 2 pages.
"External Urine Management for Female Anatomy", https://www.stryker.com/us/en/sage/products/sage-primafit.html, Jul. 2020, 4 pages.
"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.
"How Period Panties Work", www.shethinx.com/pages/thinx-itworks, 2020, 10 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"In Flight Bladder Relief", Omni Medical, 14 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology Jun. 2005", British Department of Health, Nov. 2006, 40 pages.
"Rising Warrior Insulated Gallon Jug Cover", https://www.amazon.com/Rising-Warrior-Insulated-Sleeve, 2021, 2 pages.
"Step by Step How Ur24 WorksHome", http://medicalpatentur24.com, Aug. 30, 2017, 4 pages.
"Underwear that absorbs your period", Thinx!, 7 pages.
"Urine Bag Cover-Catheter Bag Cover 2000 ml Volume-Medline Style-Multiple Sclerosis-Spine Injury-Suprapublic Catheter-Bladder Incontinence", https://www.etsy.com/listing/1142934658/urine-bag-cover-caatheter-bag-cover-2000, 2022, 1 page.
"User & Maintenance Guide", Omni Medical, 2007, 16 pages.
"Vinyl Dust Cover, Janome #741811000, Janome, Sewing Parts Online", https://www.sewingpartsonline.com/vinyl-dust-cover-janome-74181000, 2020, 2 pages.
"Winners Announced for Dare-to-Dream Medtech Design Challenge", https://www.mddionline.com/design-engineering/winners-announced-dare-dream-medtech-design-challenge, 2014, 4 pages.
Ali, "Sustainability Assessment: Seventh Generation Diapers versus gDiapers", The University of Vermont, Dec. 6, 2011, pp. 1-31.
Autumn, et al., "Frictional adhesion: a new angle on gecko attachment", The Journal of Experimental Biology, 2006, pp. 3569-3579.
CAñas, et al., "Effect of nano- and micro-roughness on adhesion of bioinspired micropatterned surfaces", Acta Biomaterialia 8, 2012, pp. 282-288.
Chaudhary, et al., "Bioinspired dry adhesive: Poly(dimethylsiloxane) grafted with poly(2-ethylhexyl acrylate) brushes", European Polymer Journal, 2015, pp. 432-440.
Dai, et al., "Non-sticky and Non-slippery Biomimetic Patterned Surfaces", Journal of Bionic Engineering, Mar. 2020, pp. 326-334.
Espinoza-Ramirez, "Nanobiodiversity and Biomimetic Adhesives Development: From Nature to Production and Application", Journal of Biomaterials and Nanobiotechnology, pp. 78-101, 2019.
Hollister, "Female Urinary and Pouch and Male Urinary Pouch Brochure", 2011, 1 page.
Hollister, "Male Urinary Pouch External Collection Device", http://www.hollister.com/en/products/Continence-Care-Products/Urine-Collectors/Urine-Collection-Accessories/Male-Urinary-Pouch-External-Collection-Device.
Hollister, "Retracted Penis Pouch by Hollister", Vitality Medical.com, 6 pages.
Hwang, et al., "Multifunctional Smart Skin Adhesive Patches for Advanced Health Care", Adv. Healthcare Mater, 2018, pp. 1-20.
Jagota, et al., "Adhesion, friction, and compliance of bio-mimetic and bio-inspired structured interfaces", Materials Science and Engineering, 2011, pp. 253-292.
Jeong, et al., "A nontransferring dry adhesive with hierarchical polymer nanohairs", PNAS, Apr. 7, 2009, pp. 5639-5644.
Jeong, et al., "Nanohairs and nanotubes: Efficient structural elements for gecko-inspired artificial dry adhesives", Science Direct, 2009, pp. 335-346.
Karp, et al., "Dry solution to a sticky problem", Nature., 2011, pp. 42-43.
Lee, et al., "Continuous Fabrication of Wide-Tip Microstructures for Bio-Inspired Dry Adhesives via Tip Inking Process", Journal of Chemistry, Jan. 2, 2019, pp. 1-5.
MacAulay, et al., "A Noninvasive Continence Management System: Development and Evaluation of a Novel Toileting Device for Women", The Wound, Ostomy and Continence Nurses Society, 2007, pp. 641-648.
Newman, et al., "The Urinary Incontinence Sourcebook", Petition for Interparties Review, 1997, 23 pages.
Newton, et al., "Measuring Safety, Effectiveness and Ease of Use of PureWick in the Management of Urinary Incontinence in Bedbound Women: Case Studies", Jan. 8, 2016, 11 pages.
Parmar, "10 Finalists Chosen for Dare-to-Dream Medtech Design Challenge (PureWick)", Design Services, Nov. 10, 2014, 3 pages.
Parness, et al., "A microfabricated wedge-shaped adhesive array displaying gecko-like dynamic adhesion, directionality", J.R. Soc. Interface, 2009, pp. 1223-1232.
Purewick, "Incontinence Relief for Women", Presentation, Sep. 23, 2015, 7 pages.
Pytlik, "Super Absorbent Polymers", University of Buffalo.
Sachtman, "New Relief for Pilots? It Depends", Wired, 2008, 2 pages.
Tsipenyuk, et al., "Use of biomimetic hexagonal surface texture in friction against lubricated skin", Journal of The Royal Society—Interface, 2014, pp. 1-6.
Advisory Action for U.S. Appl. No. 16/245,726 mailed Apr. 19, 2023.
Advisory Action for U.S. Appl. No. 16/369,676 mailed Mar. 24, 2023.
Advisory Action for U.S. Appl. No. 16/433,773 mailed Feb. 15, 2023.
Advisory Action for U.S. Appl. No. 16/452,258 mailed Oct. 26, 2022.
Advisory Action for U.S. Appl. No. 16/478,180 mailed Sep. 21, 2022.
Advisory Action for U.S. Appl. No. 16/478,180 mailed Sep. 7, 2023.
Advisory Action for U.S. Appl. No. 16/904,868 mailed Jun. 15, 2022.
Advisory Action for U.S. Appl. No. 17/051,550 mailed Sep. 8, 2023.
Advisory Action for U.S. Appl. No. 17/444,792 mailed Aug. 25, 2023.
Advisory Action for U.S. Appl. No. 17/662,700 mailed Jan. 30, 2023.
Final Office Action for U.S. Appl. No. 16/245,726 mailed Nov. 25, 2022.
Final Office Action for U.S. Appl. No. 16/369,676 mailed Aug. 31, 2023.

(56) References Cited

OTHER PUBLICATIONS

Final Office Action for U.S. Appl. No. 16/369,676 mailed Dec. 5, 2022.
Final Office Action for U.S. Appl. No. 16/433,773 mailed Oct. 25, 2022.
Final Office Action for U.S. Appl. No. 16/449,039 mailed Aug. 1, 2022.
Final Office Action for U.S. Appl. No. 16/452,258 mailed Jun. 14, 2022.
Final Office Action for U.S. Appl. No. 16/478,180 mailed Jun. 22, 2022.
Final Office Action for U.S. Appl. No. 16/478,180 mailed May 31, 2023.
Final Office Action for U.S. Appl. No. 17/051,399 mailed Mar. 9, 2023.
Final Office Action for U.S. Appl. No. 17/051,550 mailed May 23, 2023.
Final Office Action for U.S. Appl. No. 17/051,585 mailed Jul. 27, 2023.
Final Office Action for U.S. Appl. No. 17/444,792 mailed Jun. 15, 2023.
Final Office Action for U.S. Appl. No. 17/446,256 mailed Sep. 19, 2023.
Final Office Action for U.S. Appl. No. 17/448,811 mailed Aug. 3, 2023.
Final Office Action for U.S. Appl. No. 17/451,345 mailed May 3, 2023.
Final Office Action for U.S. Appl. No. 17/653,137 mailed Sep. 21, 2023.
Final Office Action for U.S. Appl. No. 17/655,464 mailed Sep. 1, 2023.
Final Office Action for U.S. Appl. No. 17/662,700 mailed Sep. 30, 2022.
International Search Report and Written Opinion from International Application No. PCT/IB2021/057173 mailed Nov. 5, 2021.
International Search Report and Written Opinion from International Application No. PCT/US2021/039866 mailed Oct. 7, 2021.
International Search Report and Written Opinion from International Application No. PCT/US2021/049404 mailed Jan. 18, 2022.
International Search Report and Written Opinion from International Application No. PCT/US2021/051456 mailed Jan. 19, 2022.
International Search Report and Written Opinion from International Application No. PCT/US2021/053593 mailed Apr. 11, 2022.
International Search Report and Written Opinion from International Application No. PCT/US2021/055515 mailed Jan. 28, 2022.
International Search Report and Written Opinion from International Application No. PCT/US2022/011108 mailed Apr. 22, 2022.
International Search Report and Written Opinion from International Application No. PCT/US2022/011281 mailed Apr. 25, 2022.
International Search Report and Written Opinion from International Application No. PCT/US2022/011419 mailed Jun. 7, 2022.
International Search Report and Written Opinion from International Application No. PCT/US2022/011421 mailed Jun. 13, 2022.
International Search Report and Written Opinion from International Application No. PCT/US2022/012794 mailed May 3, 2022.
International Search Report and Written Opinion from International Application No. PCT/US2022/014285 mailed Sep. 28, 2022.
International Search Report and Written Opinion from International Application No. PCT/US2022/014749 mailed Sep. 28, 2022.
International Search Report and Written Opinion from International Application No. PCT/US2022/015026 mailed Oct. 31, 2022.
International Search Report and Written Opinion from International Application No. PCT/US2022/015045 mailed Sep. 9, 2022.
International Search Report and Written Opinion from International Application No. PCT/US2022/015073 mailed Sep. 8, 2022.
International Search Report and Written Opinion from International Application No. PCT/US2022/015418 mailed Nov. 11, 2022.
International Search Report and Written Opinion from International Application No. PCT/US2022/015420 mailed Nov. 18, 2022.
International Search Report and Written Opinion from International Application No. PCT/US2022/015471 mailed May 16, 2022.
International Search Report and Written Opinion from International Application No. PCT/US2022/015492 mailed Apr. 26, 2022.
International Search Report and Written Opinion from International Application No. PCT/US2022/015781 mailed May 6, 2022.
International Search Report and Written Opinion from International Application No. PCT/US2022/016942 mailed Jun. 8, 2022.
International Search Report and Written Opinion from International Application No. PCT/US2022/018159 mailed Dec. 12, 2022.
International Search Report and Written Opinion from International Application No. PCT/US2022/018170 mailed May 31, 2022.
International Search Report and Written Opinion from International Application No. PCT/US2022/019254 mailed Jun. 7, 2022.
International Search Report and Written Opinion from International Application No. PCT/US2022/019480 mailed Jun. 13, 2022.
International Search Report and Written Opinion from International Application No. PCT/US2022/021103 mailed Jun. 23, 2022.
International Search Report and Written Opinion from International Application No. PCT/US2022/022111 mailed Oct. 26, 2022.
International Search Report and Written Opinion from International Application No. PCT/US2022/023594 mailed Jul. 12, 2022.
International Search Report and Written Opinion from International Application No. PCT/US2022/026667 mailed Aug. 22, 2022.
International Search Report and Written Opinion from International Application No. PCT/US2022/030685 mailed Oct. 31, 2022.
International Search Report and Written Opinion from International Application No. PCT/US2022/031032 mailed Sep. 9, 2022.
International Search Report and Written Opinion from International Application No. PCT/US2022/032424 mailed Oct. 11, 2022.
International Search Report and Written Opinion from International Application No. PCT/US2022/034457 mailed Oct. 12, 2022.
International Search Report and Written Opinion from International Application No. PCT/US2022/034744 mailed Dec. 9, 2022.
International Search Report and Written Opinion from International Application No. PCT/US2022/039018 mailed Jan. 10, 2023.
International Search Report and Written Opinion from International Application No. PCT/US2022/039022 mailed Jan. 10, 2023.
International Search Report and Written Opinion from International Application No. PCT/US2022/039711 mailed Jan. 12, 2023.
International Search Report and Written Opinion from International Application No. PCT/US2022/039714 mailed Nov. 22, 2022.
International Search Report and Written Opinion from International Application No. PCT/US2022/041085 mailed Mar. 16, 2023.
International Search Report and Written Opinion from International Application No. PCT/US2022/041688 mailed Nov. 21, 2022.
International Search Report and Written Opinion from International Application No. PCT/US2022/042719 mailed Dec. 5, 2022.
International Search Report and Written Opinion from International Application No. PCT/US2022/042725 mailed Dec. 19, 2022.
International Search Report and Written Opinion from International Application No. PCT/US2022/043818 mailed Mar. 24, 2023.
International Search Report and Written Opinion from International Application No. PCT/US2022/044107 mailed Dec. 23, 2022.
International Search Report and Written Opinion from International Application No. PCT/US2022/044208 mailed May 8, 2023.
International Search Report and Written Opinion from International Application No. PCT/US2022/044212 mailed Jan. 20, 2023.
International Search Report and Written Opinion from International Application No. PCT/US2022/044243 mailed Feb. 24, 2023.
International Search Report and Written Opinion from International Application No. PCT/US2022/049300 mailed Jun. 6, 2023.
International Search Report and Written Opinion from International Application No. PCT/US2022/050909 mailed Jul. 24, 2023.
International Search Report and Written Opinion from International Application No. PCT/US2023/012696 mailed Jul. 6, 2023.
Issue Notification for U.S. Appl. No. 16/899,956 mailed Mar. 29, 2023.
Issue Notification for U.S. Appl. No. 16/905,400 mailed Nov. 30, 2022.
Issue Notification for U.S. Appl. No. 17/088,272 mailed Jun. 15, 2022.

(56) References Cited

OTHER PUBLICATIONS

Issue Notification for U.S. Appl. No. 17/330,657 mailed Jun. 22, 2022.
Non-Final Office Action for U.S. Appl. No. 16/433,773 mailed Apr. 11, 2023.
Non-Final Office Action for U.S. Appl. No. 16/449,039 mailed Apr. 27, 2023.
Non-Final Office Action for U.S. Appl. No. 16/452,145 mailed Mar. 28, 2023.
Non-Final Office Action for U.S. Appl. No. 16/452,258 mailed Apr. 26, 2023.
Non-Final Office Action for U.S. Appl. No. 16/478,180 mailed Dec. 20, 2022.
Non-Final Office Action for U.S. Appl. No. 16/904,868 mailed Mar. 15, 2023.
Non-Final Office Action for U.S. Appl. No. 17/051,399 mailed Aug. 18, 2023.
Non-Final Office Action for U.S. Appl. No. 17/051,550 mailed Dec. 15, 2022.
Non-Final Office Action for U.S. Appl. No. 17/051,585 mailed Mar. 29, 2023.
Non-Final Office Action for U.S. Appl. No. 17/179,116 mailed Mar. 24, 2023.
Non-Final Office Action for U.S. Appl. No. 17/326,980 mailed Jul. 11, 2023.
Non-Final Office Action for U.S. Appl. No. 17/444,792 mailed Feb. 10, 2023.
Non-Final Office Action for U.S. Appl. No. 17/446,256 mailed Apr. 13, 2023.
Non-Final Office Action for U.S. Appl. No. 17/446,654 mailed Sep. 8, 2023.
Non-Final Office Action for U.S. Appl. No. 17/448,811 mailed Mar. 1, 2023.
Non-Final Office Action for U.S. Appl. No. 17/450,864 mailed May 10, 2023.
Non-Final Office Action for U.S. Appl. No. 17/451,345 mailed Dec. 7, 2022.
Non-Final Office Action for U.S. Appl. No. 17/451,354 mailed May 3, 2023.
Non-Final Office Action for U.S. Appl. No. 17/453,260 mailed Mar. 14, 2023.
Non-Final Office Action for U.S. Appl. No. 17/501,591 mailed Apr. 25, 2023.
Non-Final Office Action for U.S. Appl. No. 17/646,771 mailed Jul. 5, 2023.
Non-Final Office Action for U.S. Appl. No. 17/653,137 mailed Apr. 7, 2023.
Non-Final Office Action for U.S. Appl. No. 17/655,464 mailed Mar. 14, 2023.
Non-Final Office Action for U.S. Appl. No. 17/657,474 mailed Sep. 12, 2023.
Non-Final Office Action for U.S. Appl. No. 17/662,700 mailed Jul. 22, 2022.
Non-Final Office Action for U.S. Appl. No. 17/663,330 mailed Jun. 29, 2023.
Non-Final Office Action for U.S. Appl. No. 17/664,487 mailed Jun. 8, 2023.
Non-Final Office Action for U.S. Appl. No. 18/139,523 mailed Aug. 17, 2023.
Non-Final Office Action for U.S. Appl. No. 18/140,751 mailed Sep. 14, 2023.
Notice of Allowance for U.S. Appl. No. 16/245,726 mailed Jul. 6, 2023.
Notice of Allowance for U.S. Appl. No. 16/449,039 mailed Dec. 15, 2022.
Notice of Allowance for U.S. Appl. No. 16/899,956 mailed Aug. 10, 2022.
Notice of Allowance for U.S. Appl. No. 16/899,956 mailed Dec. 1, 2022.
Notice of Allowance for U.S. Appl. No. 16/905,400 mailed Aug. 17, 2022.
Notice of Allowance for U.S. Appl. No. 17/051,554 mailed Jul. 6, 2023.
Notice of Allowance for U.S. Appl. No. 17/461,036 mailed Feb. 22, 2023.
Notice of Allowance for U.S. Appl. No. 17/461,036 mailed Jun. 30, 2023.
Notice of Allowance for U.S. Appl. No. 17/461,036 mailed Oct. 6, 2022.
Notice of Allowance for U.S. Appl. No. 17/662,700 mailed Jul. 28, 2023.
Notice of Allowance for U.S. Appl. No. 17/662,700 mailed Mar. 28, 2023.
Notice of Allowance for U.S. Appl. No. 17/663,046 mailed Jan. 30, 2023.
Notice of Allowance for U.S. Appl. No. 18/299,788 mailed Jul. 24, 2023.
Notice of Allowance for U.S. Appl. No. 29/741,751 mailed Jun. 9, 2022.
Restriction Requirement for U.S. Appl. No. 17/051,600 mailed Sep. 21, 2023.
Restriction Requirement for U.S. Appl. No. 17/326,980 mailed Mar. 20, 2023.
Restriction Requirement for U.S. Appl. No. 17/446,256 mailed Jan. 23, 2023.
Restriction Requirement for U.S. Appl. No. 17/645,821 mailed Jul. 12, 2023.
Restriction Requirement for U.S. Appl. No. 17/646,771 mailed Apr. 6, 2023.
Restriction Requirement for U.S. Appl. No. 17/657,474 mailed Jun. 30, 2023.
Text Messages to Lorena Eckert Re Prototype PureWick Holder dated Apr. 16, 2022.
U.S. Appl. No. 17/663,046, filed May 12, 2022.
U.S. Appl. No. 17/664,487, filed May 23, 2022.
U.S. Appl. No. 17/664,914, filed May 25, 2022.
U.S. Appl. No. 17/749,340, filed May 20, 2022.
U.S. Appl. No. 17/756,201, filed May 19, 2022.
U.S. Appl. No. 17/758,152, filed Jun. 29, 2022.
U.S. Appl. No. 17/758,316, filed Jul. 1, 2022.
U.S. Appl. No. 17/759,697, filed Jul. 28, 2022.
U.S. Appl. No. 17/878,268, filed Aug. 1, 2022.
U.S. Appl. No. 17/907,125, filed Sep. 23, 2022.
U.S. Appl. No. 17/912,147, filed Sep. 16, 2022.
U.S. Appl. No. 17/929,887, filed Sep. 6, 2022.
U.S. Appl. No. 17/930,238, filed Sep. 7, 2022.
U.S. Appl. No. 17/933,590, filed Sep. 20, 2022.
U.S. Appl. No. 17/996,064, filed Oct. 12, 2022.
U.S. Appl. No. 17/996,155, filed Oct. 13, 2022.
U.S. Appl. No. 17/996,253, filed Oct. 14, 2022.
U.S. Appl. No. 17/996,468, filed Oct. 18, 2022.
U.S. Appl. No. 17/996,556, filed Oct. 19, 2022.
U.S. Appl. No. 18/003,029, filed Dec. 22, 2022.
U.S. Appl. No. 18/006,807, filed Jan. 25, 2023.
U.S. Appl. No. 18/007,105, filed Jan. 27, 2023.
U.S. Appl. No. 18/041,109, filed Feb. 9, 2023.
U.S. Appl. No. 18/042,842, filed Feb. 24, 2023.
U.S. Appl. No. 18/043,618, filed Mar. 1, 2023.
U.S. Appl. No. 18/115,444, filed Feb. 28, 2023.
U.S. Appl. No. 18/134,857, filed Apr. 14, 2023.
U.S. Appl. No. 18/140,163, filed Apr. 27, 2023.
U.S. Appl. No. 18/140,751, filed Apr. 28, 2023.
U.S. Appl. No. 18/164,800, filed Feb. 6, 2023.
U.S. Appl. No. 18/198,464, filed May 17, 2023.
U.S. Appl. No. 18/246,121, filed Mar. 21, 2023.
U.S. Appl. No. 18/247,986, filed Apr. 5, 2023.
U.S. Appl. No. 18/259,626, filed Jun. 28, 2023.
U.S. Appl. No. 18/260,122, filed Jun. 30, 2023.
U.S. Appl. No. 18/260,391, filed Jul. 5, 2023.
U.S. Appl. No. 18/260,394, filed Jul. 5, 2023.
U.S. Appl. No. 18/263,800, filed Aug. 1, 2023.
U.S. Appl. No. 18/264,004, filed Aug. 2, 2023.

(56) References Cited

OTHER PUBLICATIONS

U.S. Appl. No. 18/265,736, filed Jun. 7, 2023.
U.S. Appl. No. 18/299,788, filed Apr. 13, 2023.
U.S. Appl. No. 18/335,579, filed Jun. 15, 2023.
U.S. Appl. No. 18/373,424, filed Sep. 27, 2023.
U.S. Appl. No. 18/376,274, filed Oct. 3, 2023.
U.S. Appl. No. 18/548,152, filed Aug. 28, 2023.
U.S. Appl. No. 18/549,387, filed Sep. 7, 2023.
U.S. Appl. No. 18/549,658, filed Sep. 8, 2023.
U.S. Appl. No. 18/553,625, filed Oct. 2, 2023.
U.S. Appl. No. 62/967,158, filed Jan. 26, 2020.
U.S. Appl. No. 62/991,754, filed Mar. 19, 2020.
U.S. Appl. No. 63/150,640, filed Feb. 18, 2021.
U.S. Appl. No. 63/191,558, filed May 21, 2021.
U.S. Appl. No. 63/192,289, filed May 24, 2021.
U.S. Appl. No. 63/241,328, filed Sep. 7, 2021.
U.S. Appl. No. 63/308,190, filed Feb. 9, 2022.
*PureWick Corporation* v. *Sage Products, LLC* Transcripts vol. 2, Mar. 29, 2022.
*PureWick Corporation* v. *Sage Products, LLC* Transcripts vol. 3, Mar. 30, 2022.
*PureWick Corporation* v. *Sage Products, LLC* Transcripts vol. 4, Mar. 31, 2022.
*PureWick Corporation* v. *Sage Products, LLC* Transcripts vol. 5, Apr. 1, 2022.
*PureWick Corporation* v. *Sage Products, LLC* Transcripts vol. 1, Mar. 28, 2022.
"AMXD Control Starter Kit", Omni Medical Systems, Inc., 1 page.
"AMXDmax Advanced Mission Extender Device User & Maintenance Guide", Omni Medical, Jan. 11, 2010, 10 pages.
"AMXDmax Development History 2002-2014", Omni Medical Systems, Inc., 2 pages.
"Combat Force Multiplier in Flight Bladder Relief Cockpit Essential Equipment Brochure", Omni Medical, 20 pages.
"GSA Price List", Omni Medical, Apr. 2011, 2 pages.
"How is Polypropylene Fiber Made", https:www.yarnsandfibers.com/textile-resources/synthetic-fibers/polypropylene-fiber/polypropylene-fiber-production-raw-materials/how-is-polypropylene-fiber-made/ last accessed 2020, Oct. 7, 2020, 3 pages.
"Letter to Mark Harvie of Omni Measurement Systems", Department of Veterans Affairs, Nov. 1, 2007, 11 pages.
"Revised AMXDmax Advanced Mission Extender Device User & Maintenance Guide", Omni Medical Systems, Oct. 8, 2019, 52 pages.
Merriam-Webster Dictionary, "Embed Definition & Meaning", https://www.merriam-webster.com/dictionary/embed last accessed Aug. 3, 2023, 2003.
Pieper, et al., "An external urine-collection device for women: A clinical trial", Journal of ER Nursing, vol. 20, No. 2, Mar./Apr. 1993, pp. 51-55.
Vinas, "A Solution For An Awkward—But Serious—Subject", http://www.aero-news.net/index.cfm?do=main.textpost&id=69ae2bb1-838b-4098-a7b5-7flbb2505688 last accessed Feb. 8, 2021.
Advisory Action for U.S. Appl. No. 16/433,773 mailed Dec. 29, 2023.
Advisory Action for U.S. Appl. No. 16/449,039 mailed Jan. 25, 2024.
Advisory Action for U.S. Appl. No. 16/904,868 mailed Jan. 2, 2024.
Advisory Action for U.S. Appl. No. 17/051,585 mailed Oct. 17, 2023.
Advisory Action for U.S. Appl. No. 17/179,116 mailed Jan. 8, 2024.
Advisory Action for U.S. Appl. No. 17/446,256 mailed Dec. 8, 2023.
Advisory Action for U.S. Appl. No. 17/448,811 mailed Nov. 15, 2023.
Advisory Action for U.S. Appl. No. 17/451,345 mailed Oct. 20, 2023.
Advisory Action for U.S. Appl. No. 17/451,354 mailed Jan. 30, 2024.
Advisory Action for U.S. Appl. No. 17/453,260 mailed Dec. 22, 2023.
Advisory Action for U.S. Appl. No. 17/501,591 mailed Feb. 22, 2024.
Advisory Action for U.S. Appl. No. 17/646,771 mailed Feb. 29, 2024.
Advisory Action for U.S. Appl. No. 17/653,137 mailed Dec. 1, 2023.
Advisory Action for U.S. Appl. No. 17/655,464 mailed Dec. 13, 2023.
Advisory Action for U.S. Appl. No. 18/164,800 mailed Feb. 12, 2024.
Communication of Notice of Opposition of European Application No. 17807547.9 mailed Jan. 5, 2024.
Corrected Notice of Allowability for U.S. Appl. No. 16/369,676 mailed Dec. 7, 2023.
Corrected Notice of Allowability for U.S. Appl. No. 17/326,980 mailed Feb. 8, 2024.
Final Office Action for U.S. Appl. No. 16/433,773 mailed Oct. 10, 2023.
Final Office Action for U.S. Appl. No. 16/449,039 mailed Nov. 21, 2023.
Final Office Action for U.S. Appl. No. 16/452,258 mailed Dec. 21, 2023.
Final Office Action for U.S. Appl. No. 16/478,180 mailed Feb. 28, 2024.
Final Office Action for U.S. Appl. No. 16/904,868 mailed Nov. 2, 2023.
Final Office Action for U.S. Appl. No. 17/051,399 mailed Jan. 8, 2024.
Final Office Action for U.S. Appl. No. 17/179,116 mailed Oct. 31, 2023.
Final Office Action for U.S. Appl. No. 17/446,654 mailed Jan. 31, 2024.
Final Office Action for U.S. Appl. No. 17/450,864 mailed Dec. 28, 2023.
Final Office Action for U.S. Appl. No. 17/451,354 mailed Oct. 30, 2023.
Final Office Action for U.S. Appl. No. 17/453,260 mailed Oct. 5, 2023.
Final Office Action for U.S. Appl. No. 17/501,591 mailed Nov. 14, 2023.
Final Office Action for U.S. Appl. No. 17/646,771 mailed Dec. 21, 2023.
Final Office Action for U.S. Appl. No. 17/663,330 mailed Dec. 12, 2023.
Final Office Action for U.S. Appl. No. 17/664,487 mailed Jan. 4, 2024.
Final Office Action for U.S. Appl. No. 18/139,523 mailed Dec. 22, 2023.
Final Office Action for U.S. Appl. No. 18/140,751 mailed Jan. 17, 2024.
Final Office Action for U.S. Appl. No. 18/164,800 mailed Dec. 6, 2023.
International Search Report and Written Opinion from International Application No. PCT/US2023/018474 mailed Sep. 11, 2023.
International Search Report and Written Opinion from International Application No. PCT/US2023/024805 mailed Dec. 14, 2023.
Issue Notification for U.S. Appl. No. 16/245,726 mailed Oct. 18, 2023.
Issue Notification for U.S. Appl. No. 17/461,036 mailed Oct. 11, 2023.
Issue Notification for U.S. Appl. No. 17/663,046 mailed Dec. 20, 2023.
Issue Notification for U.S. Appl. No. 18/299,788 mailed Feb. 21, 2024.
Non-Final Office Action for U.S. Appl. No. 16/369,676 mailed Feb. 29, 2024.
Non-Final Office Action for U.S. Appl. No. 16/433,773 mailed Feb. 26, 2024.
Non-Final Office Action for U.S. Appl. No. 16/452,145 mailed Nov. 2, 2023.

(56) References Cited

OTHER PUBLICATIONS

Non-Final Office Action for U.S. Appl. No. 16/478,180 mailed Nov. 7, 2023.
Non-Final Office Action for U.S. Appl. No. 17/051,550 mailed Oct. 24, 2023.
Non-Final Office Action for U.S. Appl. No. 17/051,585 mailed Jan. 8, 2024.
Non-Final Office Action for U.S. Appl. No. 17/051,600 mailed Jan. 17, 2024.
Non-Final Office Action for U.S. Appl. No. 17/179,116 mailed Feb. 26, 2024.
Non-Final Office Action for U.S. Appl. No. 17/444,792 mailed Nov. 17, 2023.
Non-Final Office Action for U.S. Appl. No. 17/446,256 mailed Feb. 13, 2024.
Non-Final Office Action for U.S. Appl. No. 17/447,123 mailed Jan. 24, 2024.
Non-Final Office Action for U.S. Appl. No. 17/448,811 mailed Jan. 17, 2024.
Non-Final Office Action for U.S. Appl. No. 17/451,345 mailed Jan. 17, 2024.
Non-Final Office Action for U.S. Appl. No. 17/453,560 mailed Oct. 16, 2023.
Non-Final Office Action for U.S. Appl. No. 17/645,821 mailed Oct. 25, 2023.
Non-Final Office Action for U.S. Appl. No. 17/653,137 mailed Jan. 18, 2024.
Non-Final Office Action for U.S. Appl. No. 17/664,914 mailed Jan. 31, 2024.
Non-Final Office Action for U.S. Appl. No. 17/808,354 mailed Nov. 28, 2023.
Non-Final Office Action for U.S. Appl. No. 18/134,857 mailed Jan. 25, 2024.
Non-Final Office Action for U.S. Appl. No. 18/140,163 mailed Nov. 9, 2023.
Non-Final Office Action for U.S. Appl. No. 18/198,464 mailed Dec. 7, 2023.
Notice of Allowance for U.S. Appl. No. 16/369,676 mailed Nov. 14, 2023.
Notice of Allowance for U.S. Appl. No. 17/051,550 mailed Feb. 7, 2024.
Notice of Allowance for U.S. Appl. No. 17/051,554 mailed Oct. 18, 2023.
Notice of Allowance for U.S. Appl. No. 17/326,980 mailed Jan. 29, 2024.
Notice of Allowance for U.S. Appl. No. 17/453,560 mailed Jan. 31, 2024.
Notice of Allowance for U.S. Appl. No. 17/662,700 mailed Nov. 15, 2023.
Notice of Allowance for U.S. Appl. No. 18/299,788 mailed Nov. 6, 2023.
Restriction Requirement for U.S. Appl. No. 18/134,857 mailed Oct. 23, 2023.
Submission in Opposition Proceedings for European Application No. 17807547.9 filed Jan. 10, 2024.
Supplemental Notice of Allowance for U.S. Appl. No. 17/051,550 mailed Feb. 21, 2024.
Supplemental Notice of Allowance for U.S. Appl. No. 17/051,554 mailed Feb. 14, 2024.
U.S. Appl. No. 17/451,719, filed Oct. 19, 2021.
U.S. Appl. No. 18/294,370, filed Feb. 1, 2024.
U.S. Appl. No. 18/294,403, filed Feb. 1, 2024.
U.S. Appl. No. 18/389,009, filed Nov. 13, 2023.
U.S. Appl. No. 18/415,080, filed Jan. 17, 2024.
U.S. Appl. No. 18/426,795, filed Jan. 30, 2024.
U.S. Appl. No. 18/556,945, filed Oct. 24, 2023.
U.S. Appl. No. 18/558,502, filed Nov. 1, 2023.
U.S. Appl. No. 18/562,626, filed Nov. 20, 2023.
U.S. Appl. No. 18/563,672, filed Nov. 22, 2023.
U.S. Appl. No. 18/569,711, filed Dec. 13, 2023.
U.S. Appl. No. 18/569,778, filed Dec. 13, 2023.
U.S. Appl. No. 18/584,002, filed Feb. 22, 2024.
U.S. Appl. No. 18/681,987, filed Feb. 7, 2024.
U.S. Appl. No. 18/682,006, filed Feb. 7, 2024.
U.S. Appl. No. 18/687,117, filed Feb. 27, 2024.
U.S. Appl. No. 18/688,023, filed Feb. 29, 2024.
U.S. Appl. No. 63/596,012, filed Nov. 3, 2023.
U.S. Appl. No. 63/608,553, filed Dec. 11, 2023.
Wikipedia Article, "Zylinder (Geometrie)", https://de.wikipedia.org/w/index.php?title=Zylinder_(Geometrie)&oldid=154862081, version of Jun. 1, 2016, 7 pages.
Advisory Action for U.S. Appl. No. 16/452,258 mailed Apr. 8, 2024.
Advisory Action for U.S. Appl. No. 16/478,180 mailed Jun. 7, 2024.
Advisory Action for U.S. Appl. No. 17/444,792 mailed Jul. 8, 2024.
Advisory Action for U.S. Appl. No. 17/446,654 mailed Apr. 15, 2024.
Advisory Action for U.S. Appl. No. 17/450,864 mailed Mar. 21, 2024.
Advisory Action for U.S. Appl. No. 17/451,345 mailed Jul. 3, 2024.
Advisory Action for U.S. Appl. No. 17/645,821 mailed Jul. 2, 2024.
Advisory Action for U.S. Appl. No. 17/664,487 mailed Mar. 13, 2024.
Advisory Action for U.S. Appl. No. 17/808,354 mailed Jun. 12, 2024.
Advisory Action for U.S. Appl. No. 18/139,523 mailed Apr. 24, 2024.
Advisory Action for U.S. Appl. No. 18/140,163 mailed Jun. 3, 2024.
Advisory Action for U.S. Appl. No. 18/140,751 mailed Apr. 24, 2024.
Corrected Notice of Allowability for U.S. Appl. No. 17/501,591 mailed Aug. 9, 2024.
Corrected Notice of Allowability for U.S. Appl. No. 17/657,474 mailed Mar. 13, 2024.
Corrected Notice of Allowability for U.S. Appl. No. 17/657,474 mailed May 14, 2024.
Corrected Notice of Allowability for U.S. Appl. No. 17/664,914 mailed Aug. 9, 2024.
Final Office Action for U.S. Appl. No. 17/051,585 mailed Jul. 5, 2024.
Final Office Action for U.S. Appl. No. 17/051,600 mailed Jun. 27, 2024.
Final Office Action for U.S. Appl. No. 17/444,792 mailed Apr. 3, 2024.
Final Office Action for U.S. Appl. No. 17/446,256 mailed Aug. 7, 2024.
Final Office Action for U.S. Appl. No. 17/447,123 mailed May 14, 2024.
Final Office Action for U.S. Appl. No. 17/451,345 mailed Apr. 18, 2024.
Final Office Action for U.S. Appl. No. 17/645,821 mailed Apr. 3, 2024.
Final Office Action for U.S. Appl. No. 17/653,137 mailed Aug. 7, 2024.
Final Office Action for U.S. Appl. No. 17/653,920 mailed Aug. 14, 2024.
Final Office Action for U.S. Appl. No. 17/808,354 mailed Apr. 10, 2024.
Final Office Action for U.S. Appl. No. 18/134,857 mailed Jul. 25, 2024.
Final Office Action for U.S. Appl. No. 18/140,163 mailed Mar. 27, 2024.
International Search Report and Written Opinion from International Application No. PCT/US2023/025192 mailed Feb. 7, 2024.
International Search Report and Written Opinion from International Application No. PCT/US2023/025939 mailed Feb. 7, 2024.
International Search Report and Written Opinion from International Application No. PCT/US2023/030365 mailed Mar. 13, 2024.
International Search Report and Written Opinion from International Application No. PCT/US2023/030373 mailed Mar. 13, 2024.
International Search Report and Written Opinion from International Application No. PCT/US2023/031433 mailed Mar. 4, 2024.
International Search Report and Written Opinion from International Application No. PCT/US2023/031740 mailed Mar. 4, 2024.

(56) References Cited

OTHER PUBLICATIONS

International Search Report and Written Opinion from International Application No. PCT/US2023/036238 mailed Jul. 22, 2024.
International Search Report and Written Opinion from International Application No. PCT/US2023/036868 mailed Jun. 5, 2024.
International Search Report and Written Opinion from International Application No. PCT/US2023/075507 mailed Jun. 13, 2024.
International Search Report and Written Opinion from International Application No. PCT/US2023/077168 mailed Jun. 24, 2024.
International Search Report and Written Opinion from International Application No. PCT/US2023/077208 mailed May 10, 2024.
International Search Report and Written Opinion from International Application No. PCT/US2023/080680 mailed Jul. 22, 2024.
Issue Notification for U.S. Appl. No. 16/449,039 mailed Jun. 19, 2024.
Issue Notification for U.S. Appl. No. 17/051,550 mailed Mar. 13, 2024.
Issue Notification for U.S. Appl. No. 17/051,554 mailed Mar. 6, 2024.
Issue Notification for U.S. Appl. No. 17/326,980 mailed Jul. 10, 2024.
Issue Notification for U.S. Appl. No. 17/448,811 mailed Jul. 3, 2024.
Issue Notification for U.S. Appl. No. 17/453,260 mailed Jul. 10, 2024.
Issue Notification for U.S. Appl. No. 17/453,560 mailed Aug. 7, 2024.
Issue Notification for U.S. Appl. No. 17/657,474 mailed Jun. 19, 2024.
Non-Final Office Action for U.S. Appl. No. 16/452,258 mailed Jun. 20, 2024.
Non-Final Office Action for U.S. Appl. No. 16/478,180 mailed Aug. 7, 2024.
Non-Final Office Action for U.S. Appl. No. 16/904,868 mailed Mar. 12, 2024.
Non-Final Office Action for U.S. Appl. No. 17/378,015 mailed Jul. 5, 2024.
Non-Final Office Action for U.S. Appl. No. 17/446,654 mailed Jun. 25, 2024.
Non-Final Office Action for U.S. Appl. No. 17/450,864 mailed May 29, 2024.
Non-Final Office Action for U.S. Appl. No. 17/451,345 mailed Jul. 25, 2024.
Non-Final Office Action for U.S. Appl. No. 17/451,354 mailed Apr. 4, 2024.
Non-Final Office Action for U.S. Appl. No. 17/595,747 mailed Jun. 7, 2024.
Non-Final Office Action for U.S. Appl. No. 17/597,408 mailed Aug. 15, 2024.
Non-Final Office Action for U.S. Appl. No. 17/597,673 mailed Mar. 20, 2024.
Non-Final Office Action for U.S. Appl. No. 17/646,771 mailed Apr. 24, 2024.
Non-Final Office Action for U.S. Appl. No. 17/653,920 mailed Mar. 15, 2024.
Non-Final Office Action for U.S. Appl. No. 17/655,464 mailed Mar. 26, 2024.
Non-Final Office Action for U.S. Appl. No. 17/663,330 mailed Jul. 1, 2024.
Non-Final Office Action for U.S. Appl. No. 17/664,487 mailed Jun. 17, 2024.
Non-Final Office Action for U.S. Appl. No. 17/749,340 mailed Aug. 14, 2024.
Non-Final Office Action for U.S. Appl. No. 18/003,029 mailed Mar. 26, 2024.
Non-Final Office Action for U.S. Appl. No. 18/140,751 mailed Jun. 21, 2024.
Non-Final Office Action for U.S. Appl. No. 18/164,800 mailed Mar. 22, 2024.
Non-Final Office Action for U.S. Appl. No. 18/389,009 mailed May 24, 2024.
Non-Final Office Action for U.S. Appl. No. 18/426,795 mailed Aug. 9, 2024.
Non-Final Office Action for U.S. Appl. No. 18/451,080 mailed Jul. 30, 2024.
Notice of Allowance for U.S. Appl. No. 16/369,676 mailed Jun. 17, 2024.
Notice of Allowance for U.S. Appl. No. 16/449,039 mailed Mar. 28, 2024.
Notice of Allowance for U.S. Appl. No. 16/452,145 mailed Jul. 11, 2024.
Notice of Allowance for U.S. Appl. No. 17/326,980 mailed Apr. 5, 2024.
Notice of Allowance for U.S. Appl. No. 17/447,123 mailed Jul. 26, 2024.
Notice of Allowance for U.S. Appl. No. 17/448,811 mailed Jun. 14, 2024.
Notice of Allowance for U.S. Appl. No. 17/453,260 mailed Apr. 8, 2024.
Notice of Allowance for U.S. Appl. No. 17/501,591 mailed Jul. 31, 2024.
Notice of Allowance for U.S. Appl. No. 17/657,474 mailed Mar. 5, 2024.
Notice of Allowance for U.S. Appl. No. 17/657,474 mailed May 2, 2024.
Notice of Allowance for U.S. Appl. No. 17/662,700 mailed Jun. 12, 2024.
Notice of Allowance for U.S. Appl. No. 17/662,700 mailed Mar. 6, 2024.
Notice of Allowance for U.S. Appl. No. 17/664,914 mailed Jul. 26, 2024.
Notice of Allowance for U.S. Appl. No. 18/198,464 mailed Apr. 17, 2024.
Notice of Allowance for U.S. Appl. No. 18/198,464 mailed Jul. 30, 2024.
Restriction Requirement for U.S. Appl. No. 17/527,769 mailed Jun. 17, 2024.
Restriction Requirement for U.S. Appl. No. 17/625,941 mailed Aug. 7, 2024.
Restriction Requirement for U.S. Appl. No. 17/667,097 mailed Mar. 20, 2024.
U.S. Appl. No. 17/013,822, filed Sep. 7, 2020.
U.S. Appl. No. 17/444,792, filed Aug. 10, 2021.
U.S. Appl. No. 18/249,577, filed Oct. 19, 2021.
U.S. Appl. No. 18/610,523, filed Mar. 20, 2024.
U.S. Appl. No. 18/662,216, filed May 13, 2024.
U.S. Appl. No. 18/693,638, filed Mar. 20, 2024.
U.S. Appl. No. 18/694,090, filed Mar. 21, 2024.
U.S. Appl. No. 18/728,604, filed Jul. 12, 2024.
U.S. Appl. No. 18/757,964, filed Jun. 28, 2024.
U.S. Appl. No. 18/758,025, filed Jun. 28, 2024.
U.S. Appl. No. 18/834,115, filed Jul. 29, 2024.
U.S. Appl. No. 18/834,176, filed Jul. 29, 2024.
U.S. Appl. No. 18/834,340, filed Jul. 30, 2024.
U.S. Appl. No. 18/835,068, filed Aug. 1, 2024.
U.S. Appl. No. 18/835,444, filed Aug. 2, 2024.
U.S. Appl. No. 18/836,204, filed Aug. 6, 2024.
U.S. Appl. No. 63/561,893, filed Dec. 11, 2023.
U.S. Appl. No. 63/568,615, filed Mar. 22, 2024.
U.S. Appl. No. 63/683,428, filed Aug. 15, 2024.
"Oblong", Cambridge Dictionary, https://dictionary.cambridge.org/dictionary/english/oblong, 2024, 1 page.
Britannica, "Polyolefin", Britannica Online Encyclopedia, T. Editors of Encyclopaedia, https://www.britannica.com/science/polyolefin, Jul. 26, 2012.
Martin, et al., "Chapter 5 Applications of Polyethylene Oxide (POLYOX) in Hydrophilic Matrices", Hydrophilic Matrix Tablets for Oral Controlled Release, AAPS Advances in the Pharmaceutical Sciences vol. 16, 2014, pp. 123-141.
Wikipedia Article, "Decibel", https://web.archive.org/web/20200415219l7/https://en.wikipedia.org/wiki/Decibel last accessed Mar. 11, 2024, 21 pages.

(56) References Cited

OTHER PUBLICATIONS

Wikipedia Article, "Fiberglass", https://web.archive.org/web/20200309194847/https://en.wikipedia.org/wiki/Fiberglass last accessed Mar. 11, 2024.

* cited by examiner

FLUID COLLECTION ASSEMBLIES INCLUDING AT LEAST ONE LENGTH ADJUSTING FEATURE

BACKGROUND

A patient may have limited or impaired mobility such that typical urination processes are challenging or impossible. For example, the patient may have surgery or a disability that impairs mobility. In another example, the patient may have restricted travel conditions such as those experience by pilots, drivers, and workers in hazardous areas. Additionally, fluid collection from the patient may be needed for monitoring purposes or clinical testing.

Bed pans and urinary catheters, such as a Foley catheter, may be used to address some of these circumstances. However, bed pans and urinary catheters have several problems associated therewith. For example, bed pans may be prone to discomfort, spills, and other hygiene issues. Urinary catheters be may be uncomfortable, painful, and may cause urinary tract infections.

SUMMARY

Embodiments are directed towards fluid collection assemblies that include at least one length adjusting feature, fluid collection systems including the same, and methods of using the same. In an embodiment, a fluid collection assembly is disclosed. The fluid collection assembly includes a distal region, at least one proximal end region spaced from the distal region, at least one intermediate portion extending from the at least one proximal end region to the distal region, and at least one length adjusting feature extending from the at least one proximal end region towards the distal region. The at least one length adjusting feature is configured to allow a length of the fluid collection assembly to change. The fluid collection assembly also includes a fluid impermeable barrier forming at least a portion of the distal region, the at least one proximal end region, and the at least one intermediate portion. The fluid impermeable barrier at least defining a chamber, an opening at the proximal end region, and a fluid outlet. The fluid collection assembly further includes at least one porous material disposed in the chamber.

In an embodiment, a fluid collection assembly is disclosed. The fluid collection assembly includes a fluid storage container configured to hold one or more bodily fluids. The fluid collection assembly also includes a fluid collection assembly. The fluid collection assembly includes a distal region, at least one proximal end region spaced from the distal region, at least one intermediate portion extending from the at least one proximal end region to the distal region, and at least one length adjusting feature extending from the at least one proximal end region towards the distal region. The at least one length adjusting feature is configured to allow a length of the fluid collection assembly to change. The fluid collection assembly also includes a fluid impermeable barrier forming at least a portion of the distal region, the at least one proximal end region, and the at least one intermediate portion. The fluid impermeable barrier at least defining a chamber, an opening at the proximal end region, and a fluid outlet. The fluid collection assembly further includes at least one porous material disposed in the chamber. The fluid collection system further includes a vacuum source fluidly coupled to one or more of the fluid storage container or the fluid collection assembly via the conduit. The vacuum source is configured to draw fluid from the fluid collection assembly via the conduit.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Figure 1A:
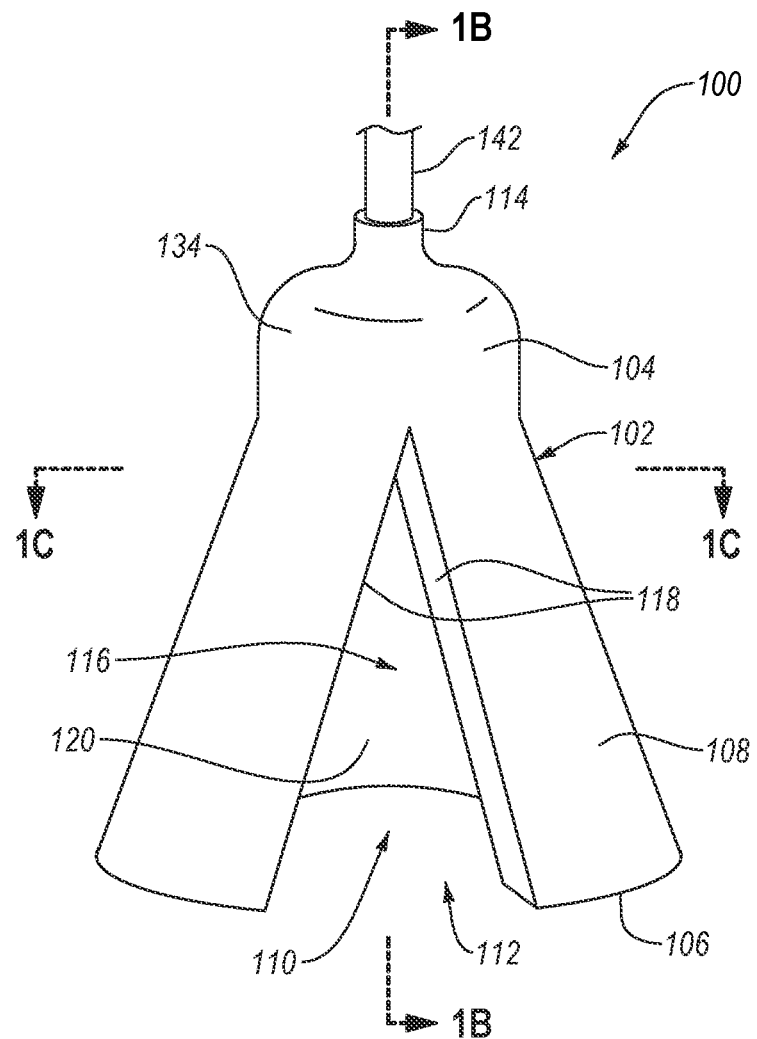
FIG. 1A is an isometric view of a fluid collection assembly, according to an embodiment.

Embodiments are directed towards fluid collection assemblies that include at least one length adjusting feature ("LAF"), fluid collection systems including the same, and methods of using the same. An example fluid collection assembly includes a fluid impermeable barrier. The fluid impermeable barrier includes a distal region, at least one proximal end region spaced from the distal region, and at least one intermediate portion extending from the distal region to the proximal end region. The fluid impermeable barrier also defines at least one LAF extending from the proximal end region towards the distal region. The LAF forms one or more lateral edges of the at least one intermediate portion. The LAF allows the length of the fluid collection assembly to change. The ability of the fluid collection assembly to change the length thereof allows a penis of a patient (i.e., an individual using the fluid collection assembly) to be disposed in preferential locations within the fluid collection assembly.

Condom male external catheters ("CMECs") are devices that are configured to have a penis disposed therein and remove bodily fluids (e.g., urine) that are discharged from the penis. CMECs are generally configured to be used with any penis, regardless of size, to at least one of minimize inventory, allow the penis to become erect without compressing the erect penis, or to prevent the need to use different CMECs depending on whether the penis is flaccid or erect. As such, the CMECs may be configured to be used with penises that, when erect, exhibit an above average size (e.g., an erect penis exhibiting a length greater than 20 cm, measured from a tip of the penis, such as the urethral opening of the penis, to the location where the shaft meets the mons pubis) and, thus, the CMEC may exhibit a length that is greater than 8 inches. However, the CMECs may be used with buried penises, flaccid penises, and penises exhibiting average to below average sizes when erect. Due to the large length of the CMECs, CMECs may exhibit a large distance between the fluid outlet of the CMEC (which is typically at a distal end region of the CMEC) and the penis when the penis is buried, flaccid, or exhibits an average or below average size when erect. The large distance between the penis and the fluid outlet may allow the bodily fluids discharged from the penis to flow in the wrong direction (e.g., away from the fluid outlet) and allow for greater loss of vacuum when a vacuum is used to remove the bodily fluids from the CMECs. Bodily fluids flowing in the wrong direction and/or the loss of vacuum may prevent or inhibit the removal of the bodily fluids from the CMECs which may cause patient discomfort (i.e., the patient remains in contact with the bodily fluids), create unsanitary conditions, and increase the likelihood that the bodily fluids leak from the CMECs.

The fluid collection assemblies disclosed herein may resolve at least some of the above discussed issues of the CMECs. For example, the fluid collection assemblies may exhibit a maximum length that is sufficiently large that the fluid collection assemblies may be used with above average sized erect penises. The fluid collection assemblies may be positioned on a penis such that the urethral opening of the penis is adjacent or at least proximate to the fluid outlet and/or distal region of the fluid collection assemblies. The LAF allows the length of the fluid collection assembly to be effectively changed (e.g., reduced) such that the urethral opening of buried penises, flaccid penises, and erect penis exhibiting average or below average lengths may be positioned adjacent or at least proximate to the fluid outlet and/or the distal region. The LAF allows the portions of the fluid collection assembly to flare outwardly (e.g., increase a width thereof) or be folded to reduce the effective length of the fluid collection assembly. Thus, the LAF may reduce the distance from the urethral opening of the penis and the fluid outlet and/or distal region thereby inhibiting the bodily fluids flowing in the wrong direction and/or inhibiting loss of vacuum.

Figure 1B:
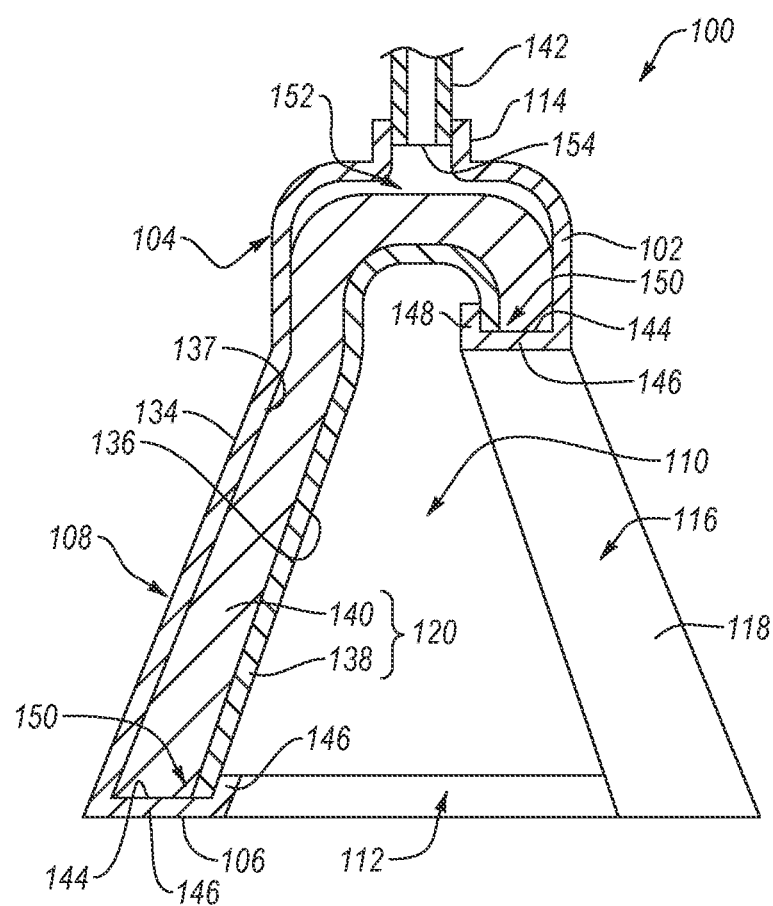
FIGS. 1B and 1C are cross-sectional schematics of the fluid collection assembly taken along planes 1B-1B and 1C-1C illustrated in FIG. 1A, respectively.
Figure 1C:
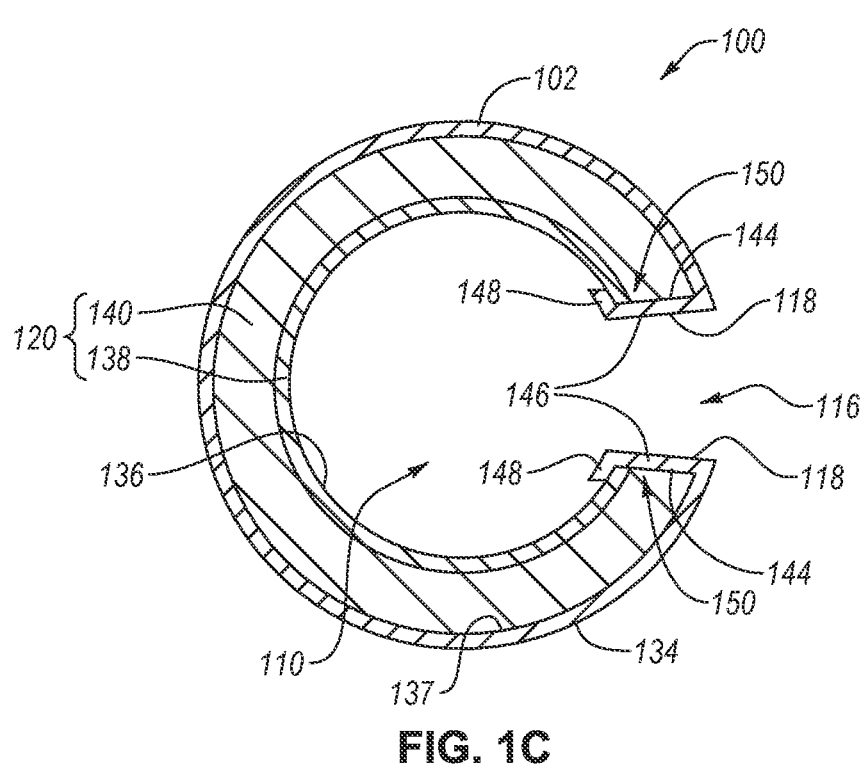

FIG. 1A is an isometric view of a fluid collection assembly 100, according to an embodiment. FIGS. 1B and 1C are cross-sectional schematics of the fluid collection assembly 100 taken along planes 1B-1B and 1C-1C illustrated in FIG. 1A, respectively, according to an embodiment. The fluid collection assembly 100 includes a distal region 104, a proximal end region 106, and an intermediate portion 108 extending from the distal region 104 to the proximal end region 106. The fluid collection assembly 100 includes a fluid impermeable barrier 102 that forms at least a portion of the distal region 104, the proximal end region 106, and the intermediate portion 108. The fluid impermeable barrier 102 also defines a chamber 110, an opening 112 at the proximal end region 106 that allows a penis 124 (partially shown in FIG. 1D) to be disposed in the chamber 110, a fluid outlet 114 at or near the distal region 104 that allows bodily fluids to be removed from the chamber 110, and at least one LAF extending from the proximal end region 106 to the distal region 104. In the illustrated embodiment, the LAF is a slit 116 that extends from the proximal end region 106 to the distal region 104. The LAF forms the lateral edges 118 of the intermediate portion 108. The fluid collection assembly 100 also includes at least one porous material 120 disposed in the chamber 110.

The distal region 104 is a portion of the fluid collection assembly 100 that is configured to have a urethral opening of the penis 124 disposed adjacent or at least proximate thereof. As such, the distal region 104 (e.g., the porous material 120 of the distal region 104) may receive bodily fluids that are discharged from the urethral opening preferentially and/or before the other portions of the fluid collection assembly 100. For example, a stream of bodily fluids that are omitted from the urethral opening may first contact the distal region 104 of the fluid collection assembly 100 though, it is noted, that the stream may contact other regions of the fluid collection assembly since the penis 124 may be flimsy when flaccid which may allow the bodily fluids to be omitted at a variety of angles even when the urethral opening is adjacent or proximate to the distal region 104.

The distal region 104 includes a portion of the fluid collection assembly 100 that is spaced from proximal end region 106 and the lateral edges 118 of the intermediate portion 108 (e.g., the LAF is not present in the distal region 104). For example, the proximal end region 106 and the lateral edges 118 represent locations through which the bodily fluids may leak from the chamber 110. As such, spacing the distal region 104 from the proximal end region 106 and the lateral edges 118 may minimize the likelihood that the bodily fluids leak from the fluid collection assembly 100.

Figure 7A:
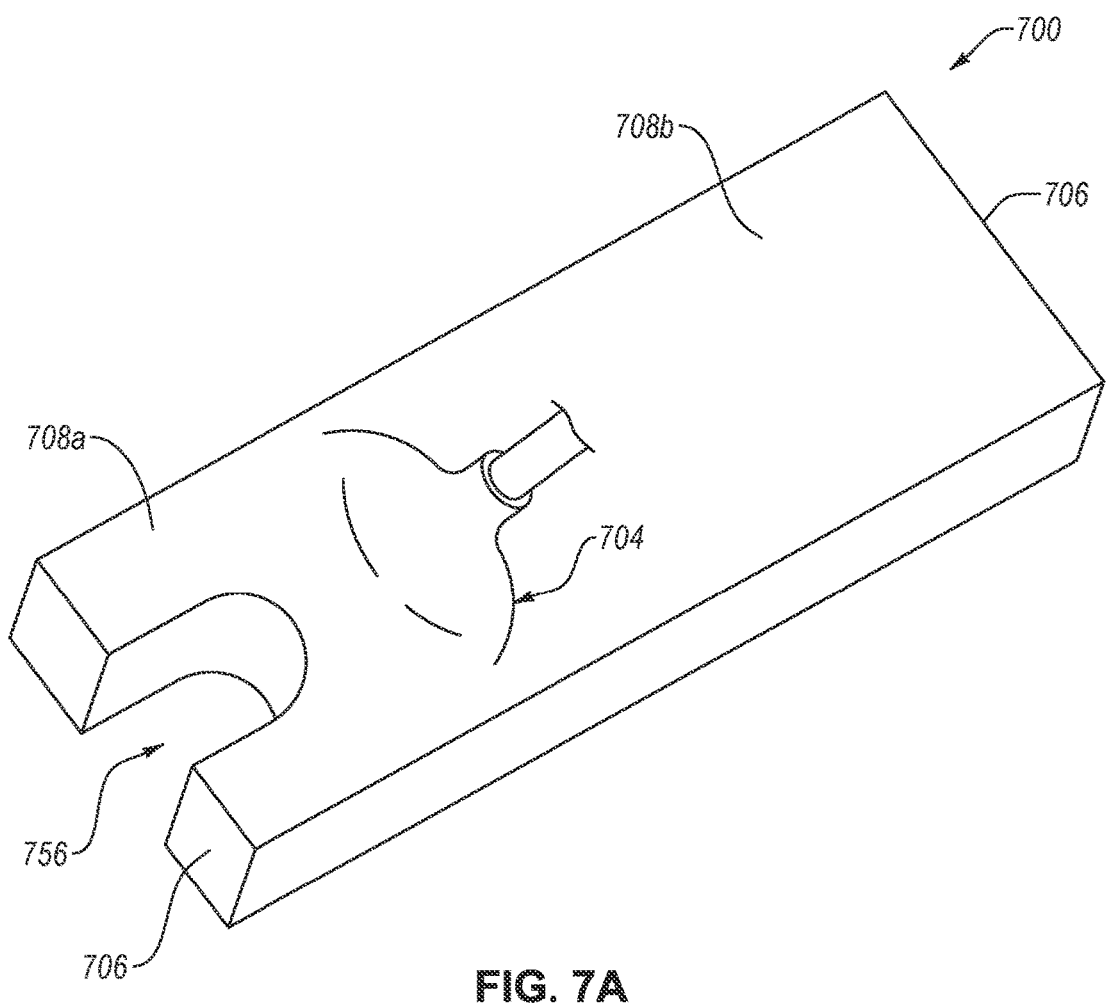
FIG. 7A is an isometric view of a fluid collection assembly, according to an embodiment.
Figure 7B:
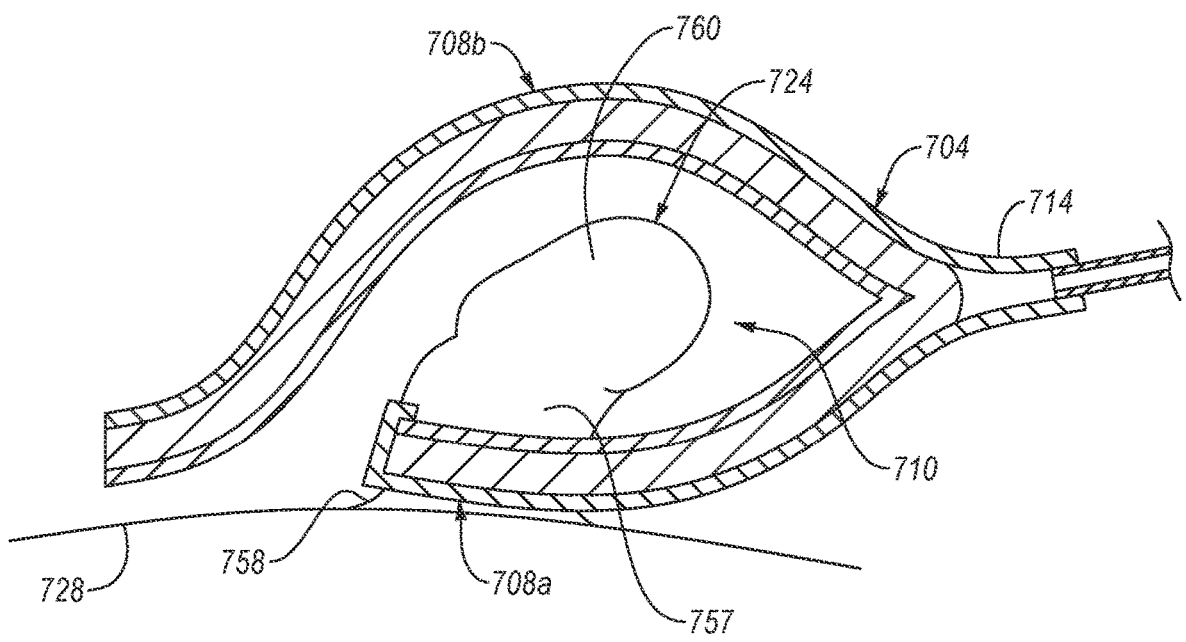
FIG. 7B is a cross-sectional schematic of the fluid collection assembly being used with a penis, according to an embodiment.

In an embodiment, as illustrated, the distal region 104 is spaced substantially equidistantly from the all portions of the proximal end region 106 which decreases the likelihood that the bodily fluids may preferentially leak from one portion of the proximal end region 106. In other words, the distal region 104 is located substantially in the middle of the fluid collection assembly 100. In an embodiment, as shown in FIGS. 7A and 7B, the distal region 104 may not be substantially equidistantly spaced from all the portions of the proximal end region 106. In other words, the distal region 104 is located off-center. However, in such an embodiment, the distal region 104 is still spaced from the proximal end region 106 and the lateral edges 118 to minimize leakage of the bodily fluids from the fluid collection assembly 100.

In an embodiment, as shown, the distal region 104 may form a sump. The distal region 104 forms a sump when the intermediate portion 108 is fully flared (e.g., the length and maximum width of the fluid collection assembly 100 cannot be smaller and bigger, respectively) and pressed against a flat surface, the portions of the distal region 104 in addition to the fluid outlet 114 may protrude upwardly from the intermediate portion 108. The sump provides a location for at least a portion of the glans (head) of the penis 124 to be disposed in. The sump may optionally provide a location for at least a portion of the shaft of the penis 124 to be disposed in. Providing a location for the glans of the penis to be positioned in may prevent inadvertently compressing the glans of the penis when the fluid collection assembly 100 is secured to the patient, as discussed in more detail below. Further, the sump may increase a distance from the urethral opening of the penis and the proximal end region 106 and the lateral edges 118 thereby decreasing the likelihood that the bodily fluids leak from the chamber 110. In an embodiment, as shown, the sump may exhibit a hollow generally cylindrical shape which generally corresponds to the shape of the penis. In an embodiment, the sump may exhibit a non-cylindrical shape, such as a generally spherical or conical shape. In an embodiment, illustrated in FIG. 8, the distal region 104 does not form a sump. In such an embodiment, the fluid outlet 114 may optionally protrude from the surface when the intermediate portion 108 is fully flared and pressed against the surface.

The fluid outlet 114 may be located on the distal region 104 since the urethral opening of the penis is positioned adjacent to or at least proximate to the distal region 104 thereby reducing the distance between the urethral opening and the fluid outlet 114. However, it is noted that the fluid outlet 114 may be spaced from the distal region 104. In an example, the fluid outlet 114 may be positioned on the intermediate portion 108 at a location that is proximate to (e.g., within about 8 cm, within about 6 cm, within about 5 cm, within about 4 cm, within about 3 cm, within about 2 cm, within about 1 cm, within about 0.5 cm, within 0.25 cm of) the distal region 104. In an example, the fluid outlet 114 may be positioned at or near an expected gravimetric low point of the chamber 110 since at least some of the bodily fluids, once received by the porous material 120, may generally flow in the direction of gravity and the distal region 104 may not be located at the gravimetric low point of the chamber 110.

As previously discussed, the fluid collection assembly 100 includes an LAF. In the illustrated embodiment, the LAF includes a slit 116 that extends from the proximal end region 106 towards (e.g., to) the distal region 104. The slit 116 is configured to control the length of the fluid collection assembly 100. In particular, the slit 116 allows at least a portion of the intermediate portion 108 to be flared (e.g., a width thereof increased) and/or folded back onto the rest of the fluid collection assembly 100. Flaring the intermediate portion 108 or folding the intermediate portion 108 back onto the rest of the fluid collection assembly 100 decreases the effective length of the fluid collection assembly 100. As used herein, the effective length refers to the maximum distance the fluid collection assembly 100 may extend from a base of a penis 124 when at least a portion of the fluid collection assembly 100 is adjacent to the base of the penis 124.

Figure 1D:
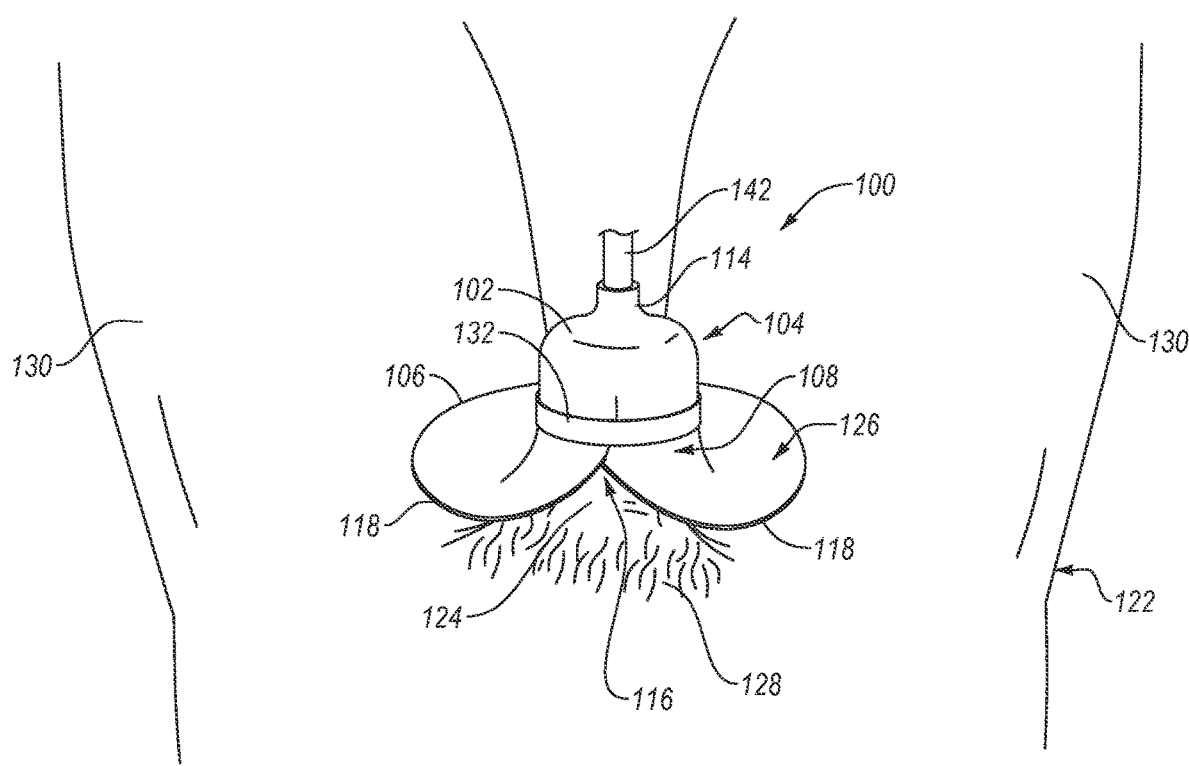
FIG. 1D is an isometric view of the fluid collection assembly shown in FIG. 1A during use, according to an embodiment.

FIG. 1D is an isometric view of the fluid collection assembly 100 during use, according to an embodiment. FIG. 1D illustrates how the LAF (e.g., slit 116) allows the length of the fluid collection assembly 100 to change. FIG. 1D illustrates a patient 122 having a penis 124 (partially obscured) that exhibits a length that is smaller than a maximum length of the fluid collection assembly 100 (e.g., a length of the fluid collection assembly 100 when no portion of the intermediate portion 108 is flared or folded). It is desirable for the urethral opening of the penis 124 to be disposed in, adjacent, or proximate to the distal region 104 for reasons previously discussed. The LAF allows the length of the fluid collection assembly 100 to be decreased such that the urethral opening of the penis 124 is in, adjacent, or proximate to the distal region 104.

In an embodiment, as shown, the length of the fluid collection assembly 100 may be changed (e.g., decreased) by flaring at least a portion of the intermediate portion 108. Flaring at least a portion of the intermediate portion 108 refers to increasing the width of at least a portion of the intermediate portion 108. The portions of the intermediate portion 108 that flare are referred to as the flared portions 126. For example, the width of the intermediate portion 108 may be increased until flared portion 126 is generally flat or exhibits a shape that generally corresponds to the shape of the region about the penis 124 (e.g., the mons pubis 128, the thighs 130, the testicles (not shown), or other anatomical feature about the penis 124). The flared portion 126 may be formed by moving corresponding portions of the lateral edges 118 (i.e., portions of the lateral edges 118 that are adjacent to each other when the slit 116 is closed) of the intermediate portion 108 away from each other. That is, the flared portion 126 may be formed by increasing a distance between corresponding portions of the lateral edges 118. Increasing the width of the flared portion 126 decreases the length of the fluid collection assembly 100.

In an embodiment, the length of the fluid collection assembly 100 may be changed by folding at least a portion of the intermediate portion 108 back onto itself and/or onto the distal region 104. In such an embodiment, folding the intermediate portion 108 may be formed, at least initially, by flaring at least a portion of the intermediate portion 108 to form a flared portion 126. After forming the flared portion 126, corresponding portions of the lateral edges 118 are brought back together (e.g., a distance between corresponding portions of the lateral edges 118 are decreased) such that an interior of at least a portion of the intermediate portion 108 faces outwardly. For example, folding the intermediate portion 108 may cause a portion of the porous material 120 to be exposed. In other words, the fluid impermeable barrier 102 of the portions of the intermediate portion 108 that were initially flared are positioned proximate to the fluid impermeable barrier 102 of the portions of the fluid collection assembly 100 that were not flared.

The change in the length of the fluid collection assembly 100 is controlled by either flaring or folding all, some, or none of the intermediate portion 108. In particular, increasing the percentage of the intermediate portion 108 that is flared or folded decreases the length of the fluid collection assembly 100. For example, flaring or folding none of the intermediate portion 108 maintains the maximum length of the fluid collection assembly 100, flaring or folding all of the intermediate portion 108 minimizes the length of the collection assembly 100, and flaring or folding only a portion of the intermediate portion 108 causes the fluid collection assembly 100 to exhibit a length that is between the maximum and minimum length. When only a portion of the intermediate portion 108 is flared or folded, greater than 0% to about 20%, about 10% to about 30%, about 20% to about 40%, about 30% to about 50%, about 40% to about 60%, about 50% to about 70%, about 60% to about 80%, about 70% to about 90%, or about 80% to about 99% of a length of the intermediate portion 108 may be flared or folded. Whether all, none, or only some of the intermediate portion 108 is flared or folded may be selected based on the size of the penis 124 that the fluid collection assembly 100 is used with so that the length of the fluid collection assembly 100 allows the urethral opening of the penis 124 to be positioned within, adjacent, or proximate to the distal region 104.

In an embodiment, the fluid collection assembly 100 may exhibit a maximum length that is greater than about 14 cm, such as about 14 cm to about 16 cm when configured to be used with average or below average sized penises only or greater than 16 cm (e.g., about 16 cm to about 20 cm or about 18 cm to about 22 cm) when configured to be used with substantially all penises. The maximum length is the maximum distance from the distal region 104 to the proximal end region 106. The fluid collection assembly 100 may exhibit a final length after at least a portion of the intermediate portion 108 is flared or folded. The final length is less than the maximum length. For example, the final length may be 0 (the distal region 104 does not include a sump) to about 2 cm, about 1 cm to about 3 cm, about 2 cm to about 4 cm, about 3 cm to about 5 cm, about 4 cm to about 6 cm, about 5 cm to about 7 cm, about 6 cm to about 8 cm, about 7 cm to about 9 cm, about 10 cm to about 12.5 cm, about 12 cm to about 15 cm, or about 14 cm to about 20 cm. The final length may be the minimum length of the fluid collection assembly 100 or a length between the maximum length and the minimum length.

In an embodiment, as previously discussed, none or only a portion of the intermediate portion 108 may be flared or folded. In such an embodiment, the fluid collection assembly 100 may include at least one retainer 132. The retainer 132 may be configured to prevent unflared or folded portions of the intermediate portion 108 from flaring or folded (e.g., prevent a distance between corresponding portions of the lateral edges 118 that do not form part of the flared portion 126 from increasing). For example, the retainer 132 may maintain the lateral edges 118 adjacent (e.g., abutting) to each other or overlap portions of the intermediate portion 108, either of which may minimize leakage through the slit 116. The retainer 132 may be positioned on (e.g., attached to, disposed on, fitted around) an exterior surface 134 of the fluid impermeable barrier 102 thereby preventing or at least inhibiting the distance between the corresponding portions lateral edges 118 adjacent to retainer 132 or between the retainer 132 and the distal region 104 from increasing. As such, the retainer 132 may inhibit a length of the fluid collection assembly 100 from changing after positioning the retainer 132 on the exterior surface 134. In an example, the retainer 132 may maintain the lateral edges 118 adjacent (e.g., abutting) to each other.

In an example, the retainer 132 may cause the unflared or unfolded portions of the intermediate portions 108 to overlap. Overlapping the unflared or unfolded portions of the intermediate portions 108 may cause the fluid collection assembly 100 to clasp a shaft of the penis 124 thereby facilitating attachment of the fluid collection assembly 100 to the patient 122. Overlapping the unflared or unfolded portions of the intermediate portions 108 may also decrease the volume of the chamber 110, thereby increasing the likelihood that the bodily fluids discharged into the chamber 110 are received into the porous material 110 instead of leaking. Other structures that may be used to clasp against the shaft of the penis 134, thereby facilitating attachment of the fluid collection assembly 100 to the patient 122 are disclosed in U.S. Provisional Patent Application No. 63/133,892 filed on Jan. 5, 2021, the disclosure of which is incorporated herein, in its entirety, by this reference.

The retainer 132 may include any device that may prevent the distance between corresponding portions of the lateral edges 118 adjacent to the retainer 132 and/or between the retainer 132 and the distal region 104 from increasing. In an example, the retainer 132 may include tape that is disposed across the slit 116. In an example, the retainer 132 may include a sleeve (e.g., ring) that fits around the exterior surface 134. The sleeve may not be adhesively attached to the exterior surface 134 of the fluid impermeable barrier 102 and, instead, may rely on friction to maintain the sleeve on the exterior surface 134. In an example, the retainer 132 may include a Velcro strap that is attached to and/or extends around the exterior surface 134. In an example, the retainer 132 may include an elastic band, rope or other string, or any other suitable device.

The intermediate portion 108 is defined by at least the distal region 104, the proximal end region 106, and the lateral edges 118 of the intermediate portion 108. The shape of the intermediate portion 108 may depend whether the intermediate portion 108 is unflared or flared. For example, the intermediate portion 108 may exhibit a generally cylindrical shape when the intermediate portion 108 is unflared, a generally truncated cylindrical shape when the intermediate portion 108 is flared, and a generally flat shape when the intermediate portion 108 is completely flared. The intermediate portion 108 may exhibit other shapes, such as a generally rectangular shape, a generally semi-cylindrical shape, at least a portion of a generally parallelepiped shape, or any other suitable shape.

In an embodiment, the intermediate portion 108 is configured to attach the fluid collection assembly 100 to the patient 122. In such an embodiment, at least a portion of the intermediate portion 108 includes an adhesive (e.g., hydrogel) on an interior surface 137 of the fluid impermeable barrier 104 or the interior surface 136 of the porous material 120. The adhesive may be configured to attach the intermediate portion 108 to the shaft of the penis and/or the region about the penis 124 thereby securing the fluid collection assembly 100 to the patient. In an example, the portions of the fluid impermeable barrier 102 that form a portion of the interior surface 137 (e.g., the inwardly extending portion 146 and/or the chamber portion 148) may include the adhesive. In an example, at least a portion of the porous material 120 that forms the interior surface 136 includes the adhesive. In an example, only portions of the interior surface 136 adjacent or proximate to the proximal end region 106 and the lateral edges 118 include the adhesive. In such an example, the adhesive may be configured to form a seal that prevents the bodily fluids from flow out of the chamber 110.

Referring back to FIGS. 1A-1C, as previously discussed, the fluid collection assembly 100 includes a fluid impermeable barrier 102. The fluid impermeable barrier 102 temporarily stores the bodily fluids discharged from a penis in the chamber 110. The fluid impermeable barrier 102 stores the bodily fluids in the chamber 110. The fluid impermeable barrier 102 may be formed of any suitable fluid impermeable material(s), such as a fluid impermeable polymer (e.g., silicone, polypropylene, polyethylene, polyethylene terephthalate, neoprene, a polycarbonate, etc.), a metal film, natural rubber, another suitable material, or combinations thereof. As such, the fluid impermeable barrier 102 substantially prevents the bodily fluids from passing through the fluid impermeable barrier 102. In an example, the fluid impermeable barrier 102 may be air permeable and fluid impermeable. In such an example, the fluid impermeable barrier 102 may be formed of a hydrophobic material that defines a plurality of pores. At least one or more portions of at least an exterior surface 134 of the fluid impermeable barrier 102 may be formed from a soft and/or smooth material, thereby reducing chaffing.

The fluid impermeable barrier 102 at least partially defines the chamber 110. For example, the interior surface 137 of the fluid impermeable barrier 102 at least partially defines the perimeter of the chamber 110. The chamber 110 may at least temporarily retain fluids therein. In an example, portions of the chamber 110 may be substantially empty due to the varying sizes and rigidity of the male penis. However, in some examples, the outermost regions of the chamber 110 may include porous material 120 (e.g., one or more of the fluid permeable membrane 138 and fluid permeable support 140). For example, the porous material 120 may be bonded to at least a portion of the interior surface 137 of the fluid impermeable barrier 102. The porous material 120 may be positioned (e.g., at the distal end of the chamber 110) to blunt a stream of urine from the male urethra thereby limiting splashing and/or to direct the bodily fluids to a selected region of the chamber 110. Since the chamber 110 is substantially empty, the fluids are likely to pool at a gravimetrically low point of the chamber 110. The gravimetrically low point of the chamber 110 may be at an intersection of the skin of a patient and the fluid collection assembly 100, the distal region 104, or another suitable location depending on the orientation of the patient. It is noted that the varying length of the fluid collection assembly 100 may allow the penis to substantially completely occupy any portions of the chamber 110 that are not occupied by the porous material 120 or that forms the reservoir 152. Substantially completely occupying such portions of the chamber 110 may position the porous material 120 adjacent to the urethral opening, thereby causing the porous material 120 to receive substantially all of the bodily fluids discharged from the urethral opening and prevent the bodily fluids remaining in the unoccupied portions of the chamber 110.

The fluid impermeable barrier 102 may also define an opening 112 extending through the fluid impermeable barrier 102 that is configured to have the penis 124 positioned therethrough. The opening 112 may be defined by the portions of the fluid impermeable barrier 102 that form the proximal end region 106. For example, the opening 112 is formed in an extends through the fluid impermeable barrier 102, from the exterior surface 134 to the interior surface 137, thereby enabling the penis 124 and bodily fluids (e.g., when the penis 124 is buried) to enter the chamber 110. The opening 112 may also be formed in and extend through the porous material 120.

In some examples, the fluid impermeable barrier 102 may define the fluid outlet 114 that is sized to receive the conduit 142. The at least one conduit 142 may be disposed in the chamber 110 via the fluid outlet 114. The fluid outlet 114 may be sized and shaped to form an at least substantially fluid tight seal against the conduit 142 or the at least one tube thereby substantially preventing the bodily fluids from escaping the chamber 110.

The porous material 120 may include one or more of the fluid permeable membrane 138 or the fluid permeable support 140. One or more of the fluid permeable membrane 138 or the fluid permeable support 140 may be disposed between the fluid impermeable barrier 102 and a penis inserted into the chamber 110. The fluid permeable membrane 138 may be positioned between the fluid impermeable barrier 102 and a penis inserted into the chamber 110, such as between the fluid permeable support 140 and penis of a patient as shown. The fluid permeable support 140 may be positioned between the fluid permeable membrane 138 and the fluid impermeable barrier 102. The interior surface 137, optionally including the end of the chamber 110 substantially opposite the opening 112, may be covered with one or both the fluid permeable membrane 138 or the fluid permeable support 140. The fluid permeable support 140 or the fluid permeable membrane 138 may be affixed (e.g., adhered) to the fluid impermeable barrier 102. The fluid permeable support 140 or the fluid permeable membrane 138 may be affixed to each other.

The fluid collection assembly 100 includes assembly porous material 120 disposed in the chamber 110. The assembly porous material 120 may cover at least a portion (e.g., all) of the opening 112. The assembly porous material 120 may include a fluid permeable membrane 138 and a fluid permeable support 140. The assembly porous material 120 is exposed to the environment outside of the chamber 110 through the opening 112. In an embodiment, the assembly porous material 120 may be configured to wick any bodily fluids away from the opening 112, thereby preventing the bodily fluids from escaping the chamber 110. The permeable properties referred to herein may be wicking, capillary action, diffusion, or other similar properties or processes, and are referred to herein as "permeable" and/or "wicking." Such "wicking" and/or "permeable" properties may not include absorption of the bodily fluids into at least a portion of the wicking material, such as not include adsorption of the bodily fluids into the fluid permeable support 140. Put another way, substantially no absorption or solubility of the bodily fluids into the material may take place after the material is exposed to the bodily fluids and removed from the bodily fluids for a time. While no absorption or solubility is desired, the term "substantially no absorption" may allow for nominal amounts of absorption and/or solubility of the bodily fluids into the wicking material (e.g., absorbency), such as less than about 30 wt % of the dry weight of the wicking material, less than about 20 wt %, less than about 10 wt %, less than about 7 wt %, less than about 5 wt %, less than about 3 wt %, less than about 2 wt %, less than about 1 wt %, or less than about 0.5 wt % of the dry weight of the wicking material. The porous material may also wick the bodily fluids generally towards an interior of the chamber 110, as discussed in more detail below. In an embodiment, the assembly porous material 120 may include at least one absorbent or adsorbent material.

The fluid permeable membrane 138 may be composed to wick the bodily fluids away from the opening 112, thereby preventing the bodily fluids from escaping the chamber 110. The fluid permeable membrane 138 may include any material that may wick the bodily fluids. For example, the fluid permeable membrane 138 may include fabric, such as a gauze (e.g., a silk, linen, or cotton gauze), another soft fabric, or another smooth fabric. Forming the fluid permeable membrane 138 from gauze, paper, soft fabric, and/or smooth fabric may reduce chaffing caused by the fluid collection assembly 100. In an embodiment, the fluid permeable membrane 138 may become quickly saturated with the bodily fluids after the porous material 120 received the bodily fluids from the penis. The fluid permeable membrane 138 may become substantially impermeable to gases when the fluid permeable membrane 138 becomes saturated with the bodily fluids thereby preventing or at least minimizing loss of a vacuum through the fluid permeable membrane 138. Preventing or minimizing the loss of the vacuum through the fluid permeable membrane 138 may increase the quantity of and rate at which the bodily fluids are removed from the chamber 110.

The fluid collection assembly 100 may include the fluid permeable support 140 disposed in the chamber 110. The fluid permeable support 140 is configured to support the fluid permeable membrane 138 since the fluid permeable membrane 138 may be formed from a relatively foldable, flimsy, or otherwise easily deformable material. For example, the fluid permeable support 140 may be positioned such that the fluid permeable membrane 138 is disposed between the fluid permeable support 140 and the fluid impermeable barrier 102. As such, the fluid permeable support 140 may support and maintain the position of the fluid permeable membrane 138. The fluid permeable support 140 may include any material that may wick or be permeable to the bodily fluids, such as any of the fluid permeable membrane materials disclosed herein above. For example, the fluid permeable membrane material(s) may be utilized in a more dense or rigid form than in the fluid permeable membrane 138 when used as the fluid permeable support 140. The fluid permeable support 140 may be formed from any fluid permeable material that is less deformable than the fluid permeable membrane 138. For example, the fluid permeable support 140 may include a porous polymer (e.g., nylon, polyester, polyurethane, polyethylene, polypropylene, etc.) structure or an open cell foam, such as spun nylon fiber. In some examples, the fluid permeable support 140 may be formed from a natural material, such as cotton, wool, silk, or combinations thereof. In an example, the fluid permeable support 140 may include a nonwoven material or a woven material (e.g., spun nylon fibers). In some examples, the fluid permeable support 140 may be formed from fabric, felt, gauze, or combinations thereof.

In an embodiment, the fluid permeable support 140 may be hydrophobic. The fluid permeable support 140 may be hydrophobic when the fluid permeable support 140 exhibits a contact angle with water (a major constituent of bodily fluids) that is greater than about 90°, such as in ranges of about 90° to about 120°, about 105° to about 135°, about 120° to about 150°, about 135° to about 175°, or about 150° to about 180°. The hydrophobicity of the fluid permeable support 140 may limit absorption, adsorption, and solubility of the bodily fluids in the fluid permeable support 140 thereby decreasing the amount of bodily fluids held in the assembly porous material 120. In an embodiment, the fluid permeable membrane 138 is hydrophobic or hydrophilic. In an embodiment, the fluid permeable support 140 is more hydrophobic (e.g., exhibits a larger contact angle with water) than the fluid permeable membrane 138. The lower hydrophobicity of the fluid permeable membrane 138 may help the assembly porous material 120 receive the bodily fluids from the urethral opening while the hydrophobicity of the fluid permeable support 140 limits the bodily fluids that are retained in the assembly porous material 120.

In some examples, the fluid permeable membrane 138 may be optional. For example, the porous material 120 may include only the fluid permeable support 140. In some examples, the fluid permeable support 140 may be optionally omitted from the fluid collection assembly 100. For example, the porous material 120 may only include the fluid permeable membrane 138. In some examples, the porous material 120 may include one or more additional layers in addition to or instead of at least one of the fluid permeable membrane 138 or the fluid permeable support 140.

In an embodiment, at least a portion of the porous material 120 at or near the proximal end region 106 may exhibit a tube-like structure (not shown) extending circumferentially about the proximal end region between the LAF. The tube-like structure of the porous material may include the fluid permeable membrane 138 rolled up into a generally curved cylindrical shape that may or may not define a channel. The fluid permeable support 140 may surround the fluid permeable membrane 138. Examples of a porous material 120 that exhibits a tube-like structure is disclosed in U.S. Pat. No. 10,376,406 filed on Jul. 27, 2016, the disclosure of which is disclosed herein, in its entirety, by this reference.

In an embodiment, the porous material 120 may be adjacent to substantially all of the interior surface 137 of the fluid impermeable barrier 102 such that there are substantially no gaps between the porous material 120 and the fluid impermeable barrier 102 ignoring the inherent porosity of the porous material 120. In an embodiment, the porous material 120 may not be adjacent to one or more portions of the interior surface 137 of the fluid impermeable barrier 102. In such an embodiment, the chamber 110 includes at least one reservoir 152 that is a substantially unoccupied portion of the chamber 110 that is between the fluid impermeable barrier 102 and the porous material 120. The bodily fluids that are in the chamber 110 may flow through the porous material 120 to the reservoir 152. The reservoir 152 may retain the bodily fluids therein until the bodily fluids are removed from the chamber 110. The reservoir 152 is depicted in the distal region 104 since the fluid outlet 114 is at or near the distal region 104. However, the reservoir 152 may be located in any portion of the chamber 110 between the fluid impermeable barrier 102 and the porous material 120, such as the proximal end region 106. The reservoir 152 may be located adjacent or proximate to the fluid outlet 114 or a gravimetrically low point of the fluid collection assembly 100 when the fluid collection assembly 100 is worn.

The fluid impermeable barrier 102 and the porous material 120 may be configured to prevent leaks from the chamber 110. In an example, the fluid impermeable barrier 102 may be configured such that the fluid impermeable barrier 102 that defines at least a portion of the lateral edges 118 contact each other when the when the slit 116 is closed (e.g., the lateral edges 118 contact each other or a portion of the intermediate portion 108 overlaps another portion of the intermediate portion 108). The fluid impermeable barrier 102 contacting itself prevents the formation of gaps through which the bodily fluids may leak and vacuum may be lost. In an example, as previously discussed, the fluid permeable membrane 138 may be configured to be substantially impermeable to gas when the fluid permeable membrane 138 becomes saturated with the bodily fluids. The saturated fluid permeable membrane 138 decreases vacuum loss which pulls the bodily fluids towards the fluid outlet 114, inhibits movement of the bodily fluids towards the slit 116 and the opening 112, and increases the quantity and rate at which the bodily fluids are removed from the chamber 110.

In an example, the fluid impermeable barrier 102 at least partially covers (e.g., extends around at least a portion of) one or more edges 144 of the porous material 120. In such an example, the fluid impermeable barrier 102 may include at least one inwardly extending portion 146 extending inwardly from a portion of the fluid impermeable barrier 102 that extends generally parallel to the porous material 120. The fluid impermeable barrier 102 may optionally include at least one chamber portion 148 extending from the inwardly extending portion 146 into the chamber 110. The inwardly extending portion 146 and/or the chamber portion 148 of the fluid impermeable barrier 102 form at least one of at least a portion of the proximal end region 106 (e.g., define a portion of the opening 112) or at least a portion of the lateral edges 118. The inwardly extending portion may prevent or at least inhibit bodily fluids from flowing out of the porous material 120 through the edges 144 thereof. The inwardly extending portion may also prevent or at least inhibit the vacuum being lost through the edges 144 of the porous material 120. The inwardly extending portion 146 and the chamber portion 148 of the fluid impermeable barrier 102 may also form a channel 150 that may store bodily fluids that reach the proximal end region 106 or the lateral edges 118. The bodily fluids stored in the channel 150 may be pulled from the channel 150 as bodily fluids are removed from the chamber 110 due to hydrogen bonding. The inwardly extending portion 146 and/or the chamber portion 148 may also increase contact between the fluid impermeable barrier 102 when the slit 116 is closed and/or a portion of the intermediate portion 108 overlaps another portion of the intermediate portion 108. The increased contact between the fluid impermeable barrier 102 reduces the likelihood that the bodily fluids leak through the slit 116.

The conduit 142 may be used to remove the bodily fluids from the chamber 110. The conduit 142 (e.g., a tube) includes an inlet 154 and an outlet (not shown) positioned downstream from the inlet 154. The outlet may be operably coupled to a vacuum source, such as a vacuum pump for withdrawing fluid from the chamber 110 through the conduit 142. For example, the conduit 142 may extend into the fluid impermeable barrier 102 from to the fluid outlet 114 to a point proximate to the reservoir 152 therein such that the inlet 154 is in fluid communication with the reservoir 152. The conduit 142 fluidly couples the chamber 110 with the fluid storage container (not shown) or the vacuum source (not shown).

The conduit 142 may include a flexible material such as plastic tubing (e.g., medical tubing). Such plastic tubing may include a thermoplastic elastomer, polyvinyl chloride, ethylene vinyl acetate, polytetrafluoroethylene, etc., tubing. In some examples, the conduit 142 may include silicon or latex. In some examples, the conduit 142 may include one or more portions that are resilient, such as to by having one or more of a diameter or wall thickness that allows the conduit to be flexible.

As described in more detail below, the conduit 142 is configured to be coupled to, and at least partially extend between, one or more of the fluid storage container (not shown) and the vacuum source (not shown). In an example, the conduit 142 is configured to be directly connected to the vacuum source (not shown). In such an example, the conduit 142 may extend from the fluid impermeable barrier 102 by at least one foot, at least two feet, at least three feet, at least six feet, or at least eight feet. In another example, the conduit 142 is configured to be indirectly connected to at least one of the fluid storage container (not shown) and the vacuum source (not shown). In some examples, the conduit is secured to a patient's skin with a catheter securement device, such as a STATLOCK® catheter securement device available from C. R. Bard, Inc., including but not limited to those disclosed in U.S. Pat. Nos. 6,117,163; 6,123,398; and 8,211,063, the disclosures of which are all incorporated herein by reference in their entirety.

The inlet 154 and the outlet are configured to fluidly couple (e.g., directly or indirectly) the vacuum source (not shown) to the chamber 110 (e.g., the reservoir 152). As the vacuum source (FIG. 9) applies a vacuum/suction in the conduit 142, the bodily fluids in the chamber 110 (e.g., at the distal region 104, such as in the reservoir 152) may be drawn into the inlet 154 and out of the fluid collection assembly 100 via the conduit 142. In some examples, the conduit may be frosted or opaque (e.g., black) to obscure visibility of the bodily fluids therein.

Figure 2A:
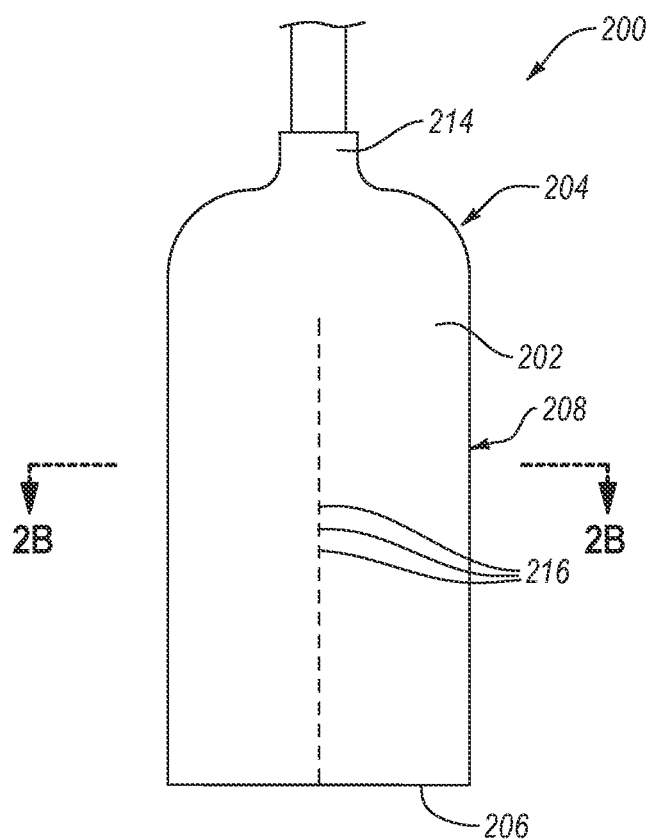
FIG. 2A is a side elevational view of a fluid collection assembly that includes a length adjusting feature other than at least one slit, according to an embodiment.
Figure 2B:
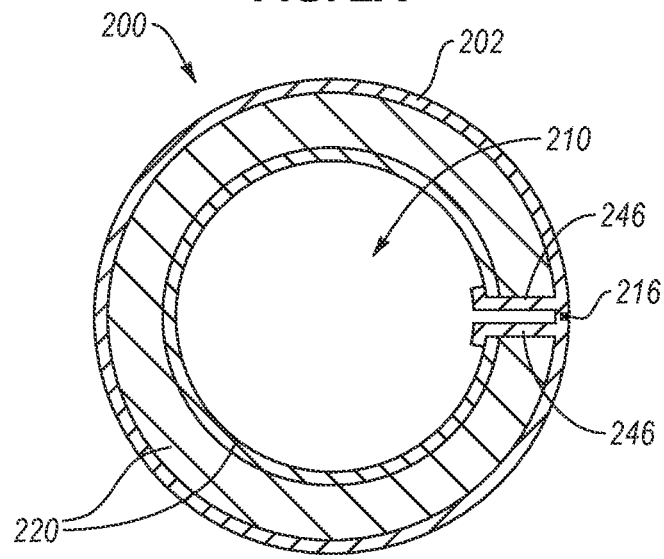
FIG. 2B is a cross-sectional schematic of the fluid collection assembly taken along plane 2B-2B illustrated in FIG. 2A, according to an embodiment.

The slit 116 illustrated in FIGS. 1A-1D is merely one example of the LAF that may be included in any of the fluid collection assemblies disclosed herein. FIG. 2A is a side elevational view of a fluid collection assembly 200 that includes a LAF other than at least one slit, according to an embodiment. FIG. 2B is a cross-sectional schematic of the fluid collection assembly 200 taken along plane 2B-2B illustrated in FIG. 2A, according to an embodiment. Except as otherwise disclosed herein, the fluid collection assembly 200 is the same of substantially similar to any of the fluid collection assemblies disclosed herein. For example, the fluid collection assembly 200 includes a distal region 204, a proximal end region 206, at least one intermediate portion 208 extending from the distal region 204 to the proximal end region 206, and at least one LAF. The fluid collection assembly also includes a fluid impermeable barrier 202 defining a chamber 210 and at least one porous material 220 disposed in the chamber 210.

The LAF of the fluid collection assembly 200 includes a plurality of perforations 216 that extend through at least a portion of the fluid impermeable barrier 202. The perforations 216 may be arranged in a path, such as a substantially straight path. The plurality of perforations 216 may extend from the proximal end region 206 to the distal region 204. The perforations 216 weaken the fluid impermeable barrier 202 such that the fluid impermeable barrier 202 is configured to tear along the path. Tearing the fluid impermeable barrier 202 along the path formed by the perforations 216 forms a slit that functions substantially similar to the slit 116 illustrated in FIGS. 1A-1D.

The slit formed using the perforations 216 does not need to extend the whole length of the path formed by the perforations 216. Instead, the slit formed using the perforations 216 may only extend a portion of the length of the path depending on the size of the penis that the fluid collection assembly 200 is used with. For example, the slit formed using the perforations 216 may only extend about greater than 0% to about 20%, about 10% to about 30%, about 20% to about 40%, about 30% to about 50%, about 40% to about 60%, about 50% to about 70%, about 60% to about 80%, about 70% to about 90%, or about 80% to about 100% the length of the path formed by the perforations 216. The percentage of the length of the path that the slit extends may be selected based on the length of the path, the maximum length of the fluid collection assembly 100, the final length of the fluid collection assembly 200, and the length of the penis. Only tearing the a portion of the path formed by the protrusion 216 allows the slit to exhibit a length that was specifically selected for a specific sized penis. In other words, the length of the slit formed from the perforations may be selected to only be as large as necessary. The selected length of the slit formed from the perforations 216 may exhibit a length that is less than the slit 116 illustrated in FIGS. 1A-1D thereby decreasing the likelihood that the bodily fluids leak from the chamber 210.

Referring to FIG. 2B, the perforations 216 may only extend a portion of a distance through the fluid impermeable barrier 202. Only extending the perforations 216 through a portion of the fluid impermeable barrier 202 may prevent bodily fluids leaking through perforations 216 that were not torn. When the fluid impermeable barrier 202 includes two inwardly extending portions 246, the perforations 216 may be positioned between the two inwardly extending portions 246.

The LAF may include features other than a slit or a plurality of perforations. In an example, the LAF may include a portion of the fluid collection assembly that is weakened, such as by selectively thinning a portion of one or more components of the fluid collection assembly or forming a portion of one or more components of the fluid collection assembly from a weaker, more easily tear-able material. The weakened portions may facilitate tearing of a portion of the fluid collection assembly similar to the plurality of perforations. In an example, the LAF may include a flexible material that extends across a recess that extends through the fluid impermeable barrier and porous material. The flexible material and the recess allows the intermediate portion of the fluid collection assembly to flare but the flexible material may prevent or at least inhibit flow of bodily fluids through the recess. In an example, the LAF may include a combination of any of the LAFs disclosed herein, such as a slit and a plurality of protrusions extending from the slit towards the distal region.

Referring back to FIG. 1B, the inlet 154 of the conduit 142 is positioned to be within the fluid inlet 114, within the fluid reservoir 152, or adjacent to the porous material 120 that is in or adjacent to the distal region 104. The inlet 154 of the conduit 142 may facilitate removal of the bodily fluids from the chamber 110 when the distal region 104 is or near the gravimetric low point of the chamber 110. For example, the bodily fluids received by the porous material 120 may predominately flow in the direction of gravity towards the distal region 104 which allows the conduit 142 to remove the bodily fluids. The conduit 142 may still remove bodily fluids when the distal region 104 is not at or near the gravimetric low point of the chamber 110. For example, the conduit 142 may still receive some of the bodily fluids and the bodily fluids received by the conduit 142 may pull additional quantities of the bodily fluids into the conduit 142 due to hydrogen bonding. However, the conduit 142 may be unable to remove bodily fluids from portions of the chamber 110 spaced from the distal region 104 when the porous material 120 is not saturated with bodily fluids and when the distal region 104 is not at or near the gravimetric low point of the chamber 110.

As such, the fluid collection assemblies disclosed herein may include positioning the inlet of the conduit at or near the expected gravimetric low point of the chamber even when the expected gravimetric low point of the chamber is not at or near the distal region. In an embodiment, the fluid outlet of the fluid collection assembly may be at or near the gravimetric low point of the chamber and spaced from the distal region. In an embodiment, as illustrated in FIGS. 3A and 3B, the conduit may extend from the fluid outlet that is spaced from the expected gravimetric low point to a location in the chamber that is at or near the expected gravimetric low point.

Figure 3A:
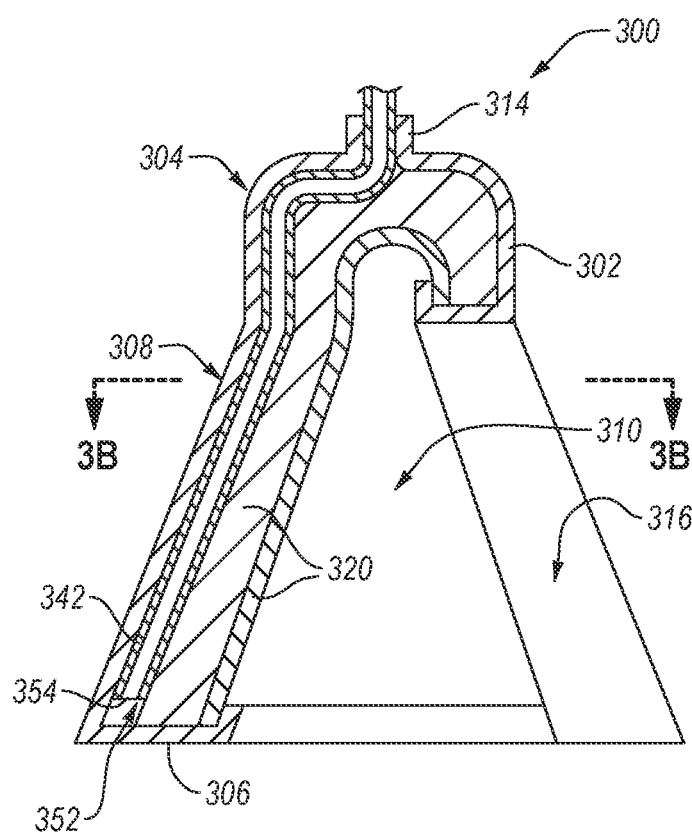
FIG. 3A is a cross-sectional schematic of a fluid collection assembly, according to an embodiment.
Figure 3B:
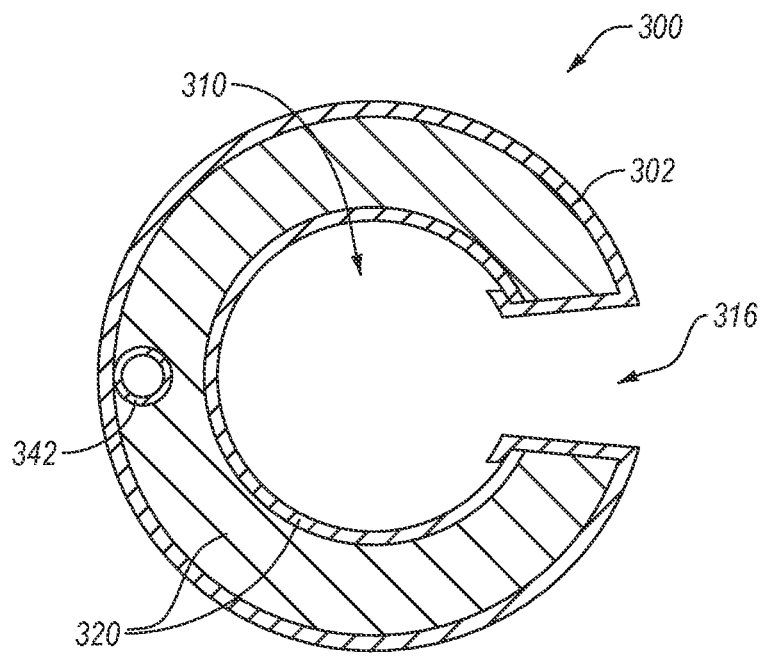
FIG. 3B is a cross-sectional schematic of the fluid collection assembly taken along plane 3B-3B shown in FIG. 3A.

FIG. 3A is a cross-sectional schematic of a fluid collection assembly 300, according to an embodiment. FIG. 3B is a cross-sectional schematic of the fluid collection assembly 300 taken along plane 3B-3B shown in FIG. 3A, according to an embodiment. Except as otherwise disclosed herein, the fluid collection assembly 300 may be the same or substantially similar to any of the fluid collection assemblies disclosed herein. For example, the fluid collection assembly 300 may include distal region 304, a proximal end region 306, at least one intermediate portion 308 extending from the distal region 304 to the proximal end region 306, and at least one LAF 316. The fluid collection assembly 300 may also include a fluid impermeable barrier 302 defining at least a chamber 310 and a fluid outlet 314. The fluid collection assembly 300 may further includes at least one porous material 320 disposed in the chamber 310.

In an embodiment, the gravimetric low point of the chamber 310 is expected to be at a location that is spaced from the fluid outlet 314. For example, the fluid outlet 314 may be located at or near the distal region 304 of the fluid collection assembly 300 while the gravimetric low point of the chamber 310 is expected to be at or near the proximal end region 306. It is noted that the fluid outlet 314 may be located at a location other than the distal region 304 (e.g., the intermediate portion 308 and/or near the proximal end region 306). It is also noted that the gravimetric low point of the chamber 310 may be at a location other than near the proximal end region 306 depending on at least one of the position of the patient (e.g., standing, sitting, or lying down) and/or the direction that the penis extends when the penis is erect or flaccid.

The conduit 342 may extend from the fluid outlet 314 to the expected gravimetric low point of the chamber 310 such that the inlet 354 of the conduit 342 is at or near the expected gravimetric low point. For example, in the illustrated embodiment, the conduit 342 may extend from the fluid outlet 314, at least one of between the fluid impermeable barrier 302 and the porous material 320, through the porous material 320 (e.g., through a bore formed in the porous material 320), or in an unoccupied spaced defined partially by the porous material 320 that also receives the penis (not shown). Positioning the inlet 354 of the conduit 342 at or near the expected gravimetric low point of the chamber 310 may facilitate removal of the bodily fluids from the chamber 310 since at least some of the bodily fluids may flow towards the gravimetric low point of the chamber 310.

In an embodiment, the chamber 310 may include a substantially unoccupied space at or near the proximal end region 306 or any other location that may be expected to be the gravimetric low point of the chamber 310. The substantially unoccupied space may be a reservoir 352 that is configured to temporarily store the bodily fluids therein.

In an embodiment, the conduit of any of the fluid collection assemblies disclosed herein may define a plurality of inlets thereby allowing the conduit to receive bodily fluids from a variety of locations in the chamber. In an embodiment, the conduit of any of the fluid collection assemblies disclosed herein may include a plurality of conduits and an inlet of at least one of the plurality of conduits is positioned in a location that is different than an inlet of at least one other one of the plurality of conduits thereby allowing the conduits to receive bodily fluids from a variety of locations in the chamber.

The fluid collection assemblies illustrated in FIGS. 1A-3B are illustrated as including only a single intermediate portion. However, it is noted that the fluid collection assemblies disclosed herein may include any suitable number of intermediate portions, such as 2 intermediate portions, 3 intermediate portions, 4 intermediate portions, 5 intermediate portions, or 6 or more intermediate portions. Each of the plurality of intermediate portions may be separated by an LAF (e.g., slit, perforations, etc.).

Figure 4A:
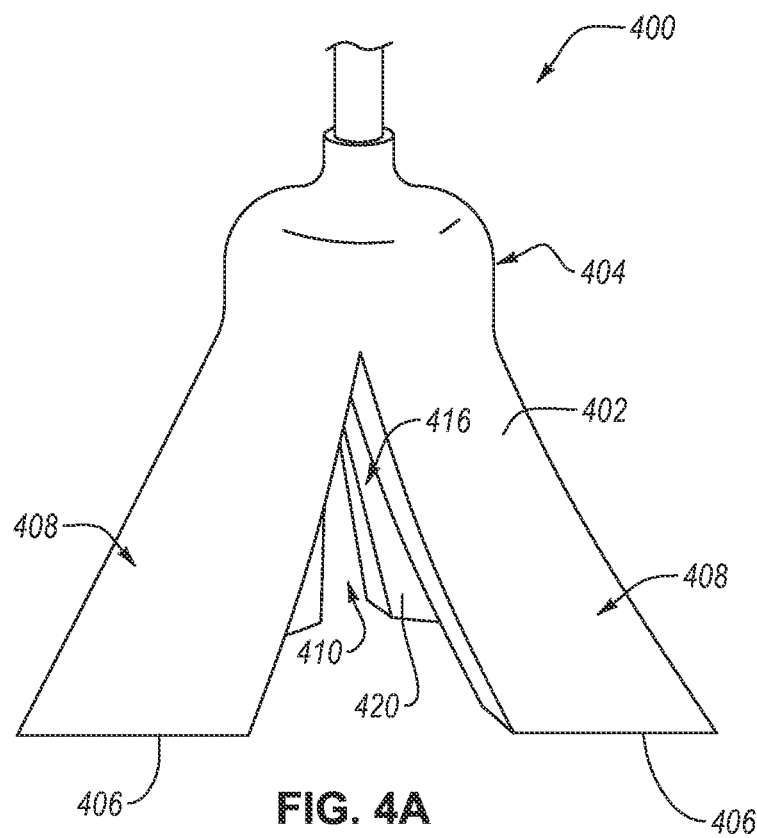
FIG. 4A is an isometric view of a fluid collection assembly that includes a two intermediate portions, according to an embodiment.

FIG. 4A is an isometric view of a fluid collection assembly 400 that includes a two intermediate portions 408, according to an embodiment. Except as otherwise disclosed herein, the fluid collection assembly 400 is the same or substantially similar to any of the fluid collection assemblies disclosed herein. For example, the fluid collection assembly 400 may include a distal region 404 and proximal end regions 406 spaced from the distal region 404. The fluid collection assembly 400 also includes a fluid impermeable barrier 402 defining at least a chamber 410 and at least one porous material 420 disposed in the chamber 410.

The fluid collection assembly 400 includes two intermediate portions 408 each extending from the distal region 404 to the proximal end regions 406. The two intermediate portions 408 are separated from each other by two LAFs 416. In the illustrated embodiment, the two intermediate portions 408 may be generally aligned linearly and/or may extend generally parallel to each other as the two intermediate portions 408 extend from the distal region 404. However, the two intermediate portions 408 may also extend from the distal region 404 while not being at least one of generally aligned linearly with each other or generally parallel to each other.

The intermediate portions 408 may be the same or substantially similar to any of the intermediate portions disclosed herein. For example, the intermediate portions 408 may include a fluid impermeable barrier 402 and at least one porous material 420 disposed adjacent to at least a portion of the fluid impermeable barrier 402 of each of the intermediate portions 408. The intermediate portions 408 may also exhibit any shape disclosed herein. For example, the intermediate portions 408 may exhibit a generally rectangular shape, a generally semi-cylindrical shape, a generally parallelepiped shape, or any other suitable shape.

In an embodiment, the two intermediate portions 408 are substantially the same. For example, the two intermediate portions 408 may exhibit the same size, the same shape, etc. In an embodiment, the two intermediate portions 408 may be different from each other in one or more aspects. For example, the intermediate portions 408 may exhibit different sizes, different shapes, one of the intermediate portions 408 may include a porous material 420 that is different than a porous material 420 of the other intermediate portion 408, one intermediate portion 408 may include a reservoir and/or a conduit extending therethrough while the other intermediate portion 408 does not, one intermediate portion 408 may include the fluid outlet 414, etc.

Figure 4B:
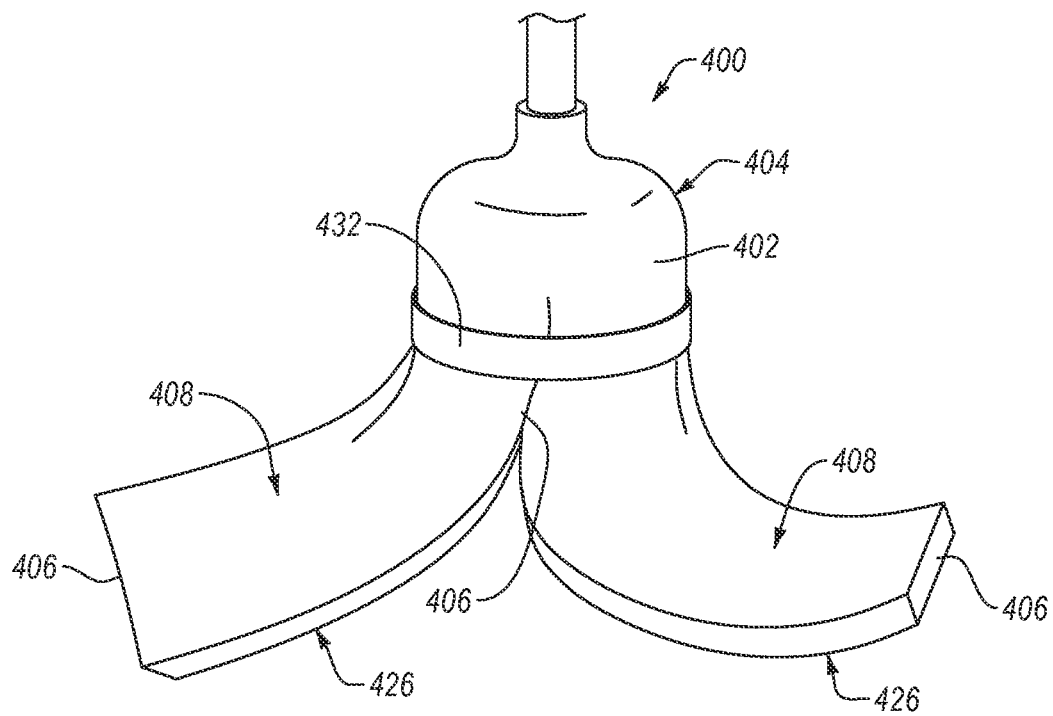
FIG. 4B is an isometric view of the fluid collection assembly during use, according to an embodiment.

FIG. 4B is an isometric view of the fluid collection assembly 400 during use, according to an embodiment. The penis (patient not shown for clarity) may be disposed in the chamber 410 such that the penis is adjacent or at least proximate to the distal region 404. At least a portion of intermediate portions 408 may be flared (as shown) or folded to reduce the length of the fluid collection assembly 400 such that the penis is within, adjacent or at least proximate to the distal region 404. The fluid collection assembly 400 may include a retainer 432 to prevent or at least inhibit the unflared portions of the intermediate portions 408 from flaring.

In an embodiment, the flared portions 426 of the intermediate portions 408 may be flared outwardly until each of the flared portions 426 exhibits a shape that generally corresponds to the shape of the region about the penis that the flared portions 426 contact. The portions of the body that the flared portions 426 correspond to may depend on the orientation (e.g., rotation) of the fluid collection assembly 400 exhibit relative to the patient. In an example, the flared portions 426 may be flared until at least a portion of the flared portions 426 exhibit a shape that generally corresponds to the shape of the thighs of the patient. In an example, the flared portions 426 may be flared until at least a portion of the flared portion 426 of one of the intermediate portions 408 exhibit a shape that generally corresponds to the shape of at least a portion of the testicles of the patient while the flared portion 426 of the other intermediate portions 408 exhibits a shape that generally corresponds to the shape of the mons pubis. In an embodiment, the flared portions 426 may be flared such that the flared portions 426 do not exhibit a shape that corresponds to the shape of the region about the penis. For example, the flared portions 426 may be folded upwardly such that at least a portion of the fluid impermeable barrier 402 of the flared portions 426 is adjacent to the fluid impermeable barrier 402 of at least a portion of the rest of the fluid collection assembly 400.

Figure 5A:
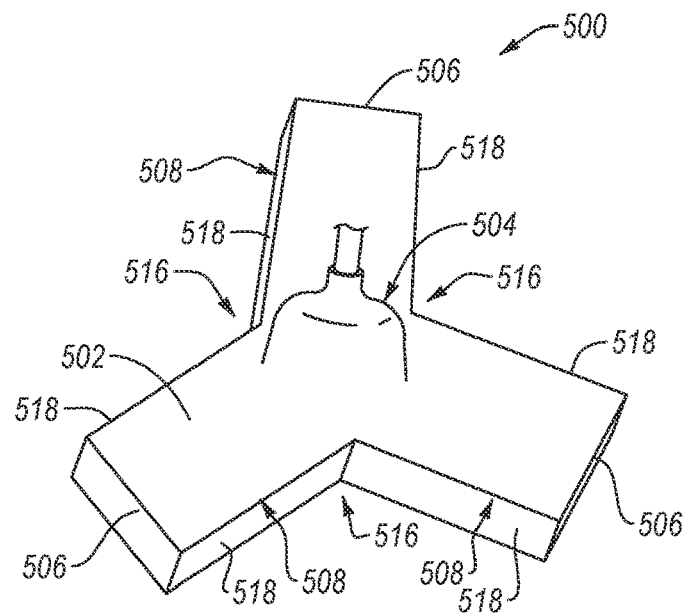
FIG. 5A is an isometric view of a fluid collection assembly, according to an embodiment.
Figure 5B:
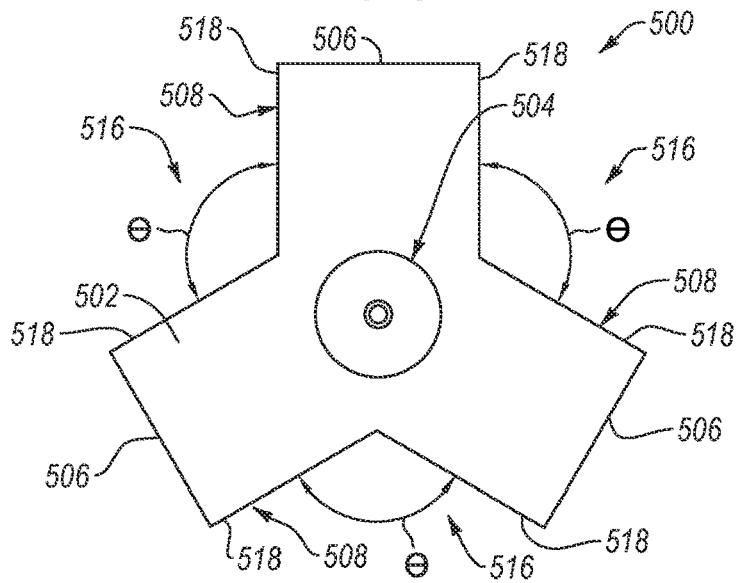
FIG. 5B is a top plan view of the fluid collection assembly, according to an embodiment.
Figure 5C:
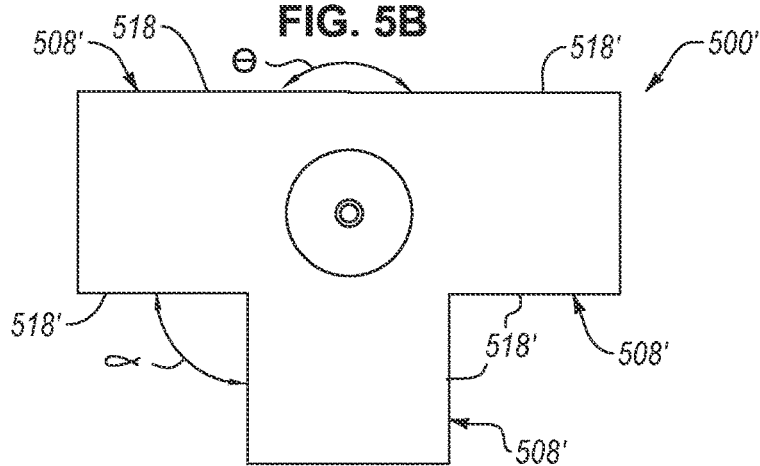
FIG. 5C is a top plan view of a fluid collection assembly that includes a plurality of intermediate portions that are not equidistantly spaced, according to an embodiment.

As previously discussed, the fluid collection assembly 400 includes two intermediate portions. However, any of the fluid collection assemblies disclosed herein may include more than two intermediate portions, such as three intermediate portions as illustrated in FIGS. 5A-5C. FIG. 5A is an isometric view of a fluid collection assembly 500, according to an embodiment. FIG. 5B is a top plan view of the fluid collection assembly 500, according to an embodiment. Except as otherwise disclosed herein, the fluid collection assembly 500 may be the same or substantially similar to any of the fluid collection assemblies disclosed herein. For example, the fluid collection assembly 500 may include a distal region 504, proximal end regions 506 spaced from the distal region 504, three intermediate portions 508, and at least one LAF 516 disposed between each of the three intermediate portions 508. For illustrative purposes, the intermediate portions 508 are illustrated as being flared though, it is noted, the intermediate portions 508 may not be flared. The fluid collection assembly 500 also includes a fluid impermeable barrier 502 and at least one porous material (not shown).

As previously discussed, the fluid collection assembly 500 includes three intermediate portions 508. The three intermediate portions 508 allows the fluid collection assembly 500 to be attached to more regions of the body of the patient that is using the fluid collection assembly 500 than if the fluid collection assembly 500 only included one or two intermediate portions. In an example, the three intermediate portions 308 allows the fluid collection assembly 500 to be attached to the two thighs and the mons pubis of the patient. Allowing the fluid collection assembly 500 to be attached to more portions of the bodily causes the fluid collection assembly 500 to pull less on each portion of the patient thereby increasing patient comfort In an example, the three intermediate portions 508 allows two of the intermediate portions 508 to be attached above the penis (i.e., in a region generally between the penis and head of the patient) or to the side of the penis while the remaining intermediate portion 508 may be attached below the penis (i.e., in a region generally between the penis and the feet of the patient). In an example, the three intermediate portions 508 allows two of the intermediate portions 508 to be attached below or to the sides of the penis while the remaining intermediate portion 508 may be attached above the penis. In an embodiment, the three intermediate portions 508 may minimize pivoting and increase the likelihood that the fluid collection assembly 500 stays attached to the patient than if the fluid collection assembly 500 included fewer intermediate portions.

The three intermediate portions 508 may allow the fluid collection assembly 500 to be attached to the patient without attaching one or more of the intermediate portions 508 to sensitive portions of the patient (e.g., testicles) compared to a fluid collection assembly that includes two or fewer intermediate portions. In an example, the intermediate portions 508 may be attached to the mons pubis without also attaching the intermediate portions 508 to the testicles whereas attaching one of the intermediate portions 408 of the fluid collection assembly 400 illustrated in FIG. 4A to the mons pubis may also cause the other intermediate portion to be attached to the testicles. In an example, the fluid collection assembly 500 may be positioned on the patient such that one of the intermediate portions 508 may be attached to the testicles.

It is noted that generally, increasing the number of intermediate portions increases the comfort of using the fluid collection assembly by increasing the number of locations to which the intermediate portions may be attached while also avoiding more sensitive portions of the patient.

Referring to FIG. 5B, the intermediate portions 508 may be "equidistantly spaced" when each angle θ between two adjacent lateral edges 518 of different intermediate portions 508 are the same or substantially the same. In the illustrated embodiment, the angle θ is about 120° when the three intermediate portions 508 are equidistantly spaced. Equidistantly spacing intermediate portions 508 may allow each of the intermediate portions 508 to more equally carry the weight of the fluid collection assembly 500 when the intermediate portions 508 are attached to the patient as the patient moves. It is noted that the other fluid collection assemblies disclosed herein may have their intermediate portions equidistantly spaced. In an example, the fluid collection assembly 400 illustrated in FIGS. 4A and 4B may have equidistantly spaced intermediate portions 408 when the angle between the two intermediate portions is about 180° (i.e., aligned linearly). In an example, a fluid collection assembly with four equidistantly spaced intermediate portions has an angle between adjacent set of intermediate portions that is about 90°, a fluid collection assembly with five equidistantly spaced intermediate portions has an angle between adjacent set of intermediate portions that is about 72°, and so forth.

The intermediate portions of any of the fluid collection assemblies disclosed herein may have non-equidistantly spaced intermediate portions (e.g., an angle between two adjacent lateral edges of a first set of two different intermediate portions is different than an angle between two other adjacent lateral edges of a second set of two different intermediate portions). For example, FIG. 5C is a top plan view of a fluid collection assembly 500' that includes a plurality of intermediate portions 508' that are not equidistantly spaced, according to an embodiment. The fluid collection assembly 500' is similar to any of the fluid collection assemblies disclosed herein (e.g., the fluid collection assembly 500 illustrated in FIGS. 5A and 5B) in one or more aspects. For example, the fluid collection assembly 500' includes a plurality (e.g., three) intermediate portions 508'. However, unlike the other fluid collection assemblies disclosed herein, the intermediate portions 508' are not equidistantly spaced. For example, an angle θ is measure between adjacent lateral edges 518' of two different intermediate portions 508' and an angle α is measured between other adjacent lateral edges 518' of two different intermediate portions 508', where the angle θ and the angle α are different. The angles between the other adjacent set of intermediate portion(s) may be the same or different than at least one of the angle θ and the angle α.

The angle θ and the angle α may be selected such that the intermediate portions 508' are attached to selected portions of the body and/or avoid certain portions of the body. For example, the angle θ may be selected such that the intermediate portions 508' that the angle θ is measured between avoids the testicles. For instance, the angle θ may be selected to be about 120° to about 200° (e.g., about 180°) thereby allowing the corresponding set of adjacent intermediate portions 508' are attached to the thighs instead of the testicles. The angle α may be selected such that one of the intermediate portions 508' that the angle α is measured between contacts the mons pubis or another location other than the testicles. As such, the angle θ and the angle α are selected to avoid attaching or contacting one of the intermediate portions 508' against the testicles.

Figure 6:
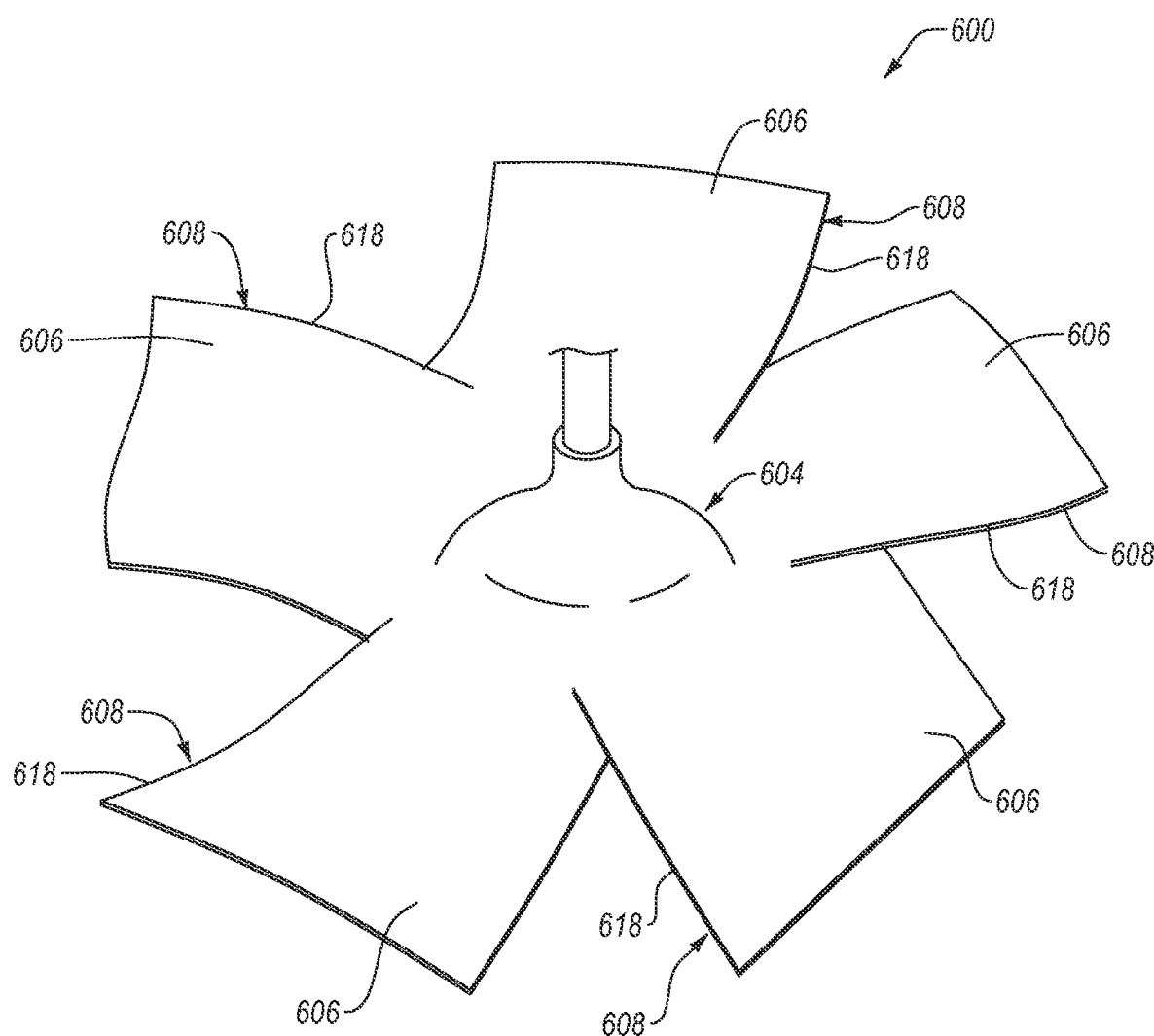
FIG. 6 is an isometric view of a fluid collection assembly that includes overlapping intermediate portions, according to an embodiment.

In some embodiments, the intermediate portions of any of the fluid collection assemblies disclosed herein may overlap. For example, FIG. 6 is an isometric view of a fluid collection assembly 600 that includes overlapping intermediate portions 608, according to an embodiment. Except as otherwise disclosed herein, the fluid collection assembly 600 is the same of substantially similar to any of the fluid collection assemblies disclosed herein. For example, the fluid collection assembly 600 includes a distal region 604, proximal end regions 606 spaced from the distal region 604, and a plurality of intermediate portions 608 extending from the distal region 604 to the proximal end regions 606.

As previously discussed, the fluid collection assembly 600 includes a plurality of intermediate portions 608 and at least a portion of at least some of the plurality of intermediate portions 608 overlap with each other. The intermediate portions 608 overlap when one intermediate portion 608 covers a portion of another intermediate portion 608 (e.g., an adjacent intermediate portion 608) when the intermediate portions 608 are completely flared. The overlapping intermediate portion 608 generally covers a portion of the adjacent intermediate portion 608 that is adjacent to the distal region 604.

The overlapping of the intermediate portions 608 prevents or at least inhibits bodily fluids from leaking from the chamber (not shown) of the fluid collection assembly 600. For example, one of the more likely locations of the fluid collection assembly 600 that the bodily fluids may leak from is through the LAF adjacent to the distal region 604. In fluid collection assemblies that do not include overlapping intermediate portions, any bodily fluids that flow around the lateral edge of an intermediate portion adjacent to the distal region may be able to leak from the such a fluid collection assembly. However, in the fluid collection assembly 600 illustrated in FIG. 6, the bodily fluids that flow around a lateral edge 618 of a first intermediate portion 608 that is adjacent to the distal region 604 must flow between the first intermediate portion 608 and the intermediate portion 608 that overlaps the first intermediate portion 608 without being received by the porous material before the bodily fluids may leak from the fluid collection assembly 600. As such, the overlapping intermediate portions 608 decrease the likelihood that the bodily fluids leak from the fluid collection assembly 600 than if the intermediate portions 608 did not overlap.

In an embodiment, all of the intermediate portions 608 are partially overlapped by another intermediate portion 608 and, by extension, all of the intermediate portions 608 partially overlap another intermediate portion 608. In an embodiment, at least one of the intermediate portions 608 is overlapped by two intermediate portions adjacent intermediate portion 608. In an embodiment, at least one of the intermediate portion 608 is not overlapped and/or does not overlap another intermediate portion 608.

The fluid collection assemblies illustrated in FIGS. 1A-6 are illustrated as having 1, 2, 3, or 5 intermediate portions. However, the fluid collection assemblies disclosed herein may include any number of intermediate portions. For example, the fluid collection assemblies disclosed herein may include 4 or 6 or more intermediate portions. It is noted that it is generally believed that increasing the number of intermediate portions beyond 6 may adversely affect the operation of the fluid collection assembly. For instance, increasing the number of intermediate portions of a fluid collection assembly beyond 6 may make attaching the fluid collection assembly patient without attaching the intermediate portions to themselves or to the wrong portion of the patient difficult. Further, increasing the number of intermediate portions of the fluid collection assembly beyond 6 may increase the chances of bodily fluids leaking from the fluid collection assembly due to the number of LAFs through which the bodily fluids may leak.

The fluid collection assemblies illustrated in FIGS. 4A-6 include intermediate portions that extend a substantially equal distance from the distal regions thereof. However, the fluid collection assemblies disclosed herein may include intermediate portions that do not extend a substantially equal distance from the distal regions thereof, as shown in FIGS. 7A-7B. The fluid collection assembly that includes intermediate portions that do not extend a substantially equal distance from the distal regions thereof may allow such a fluid collection assembly to be positioned against the penis that would be difficult to do if the intermediate portions extended a substantially equal distance from the distal region. FIG. 7A is an isometric view of a fluid collection assembly 700, according to an embodiment. Except as otherwise disclosed herein, the fluid collection assembly 700 is the same or substantially similar to any of the fluid collection assemblies disclosed herein. For example, the fluid collection assembly 700 includes a distal region 704, proximal end regions 706 spaced from the distal region 704, and a plurality of intermediate portions extending from the distal region 704 to the proximal end region 706.

The fluid collection assembly 700 includes a first intermediate portion 708*a* and a second intermediate portion 708*b*. The first intermediate portion 708*a* extends a first distance from the distal region 704 and the second intermediate portion 708*b* extends a second distance from the distal region 704, wherein the second distance is greater than the first distance. In other words, the first intermediate portion 708*a* exhibits a length that is less than a length of the second intermediate portion 708*b*. As will be discussed in more detail with regards to FIG. 7B, the different lengths of the first and second intermediate portion 708*a*, 708*b* may facilitate attachment of the fluid collection assembly 700 to a penis 724 (shown in FIG. 7B).

The proximal end region 706 formed by the first intermediate portion 708*a* or a portion of the first intermediate portion 708*a* adjacent to the proximal end region 706 is configured to abut or at least partially surround the penis 724 (shown in FIG. 7B). For example, some of the bodily fluids discharged from the penis 724 into the chamber 710 (shown in FIG. 7B) may flow down the shaft 757 of the penis 724 or the penis may lay on either side rather than straight up. The portion(s) of the first intermediate portion 708*a* that abut or at least partially surround the penis 724 may receive or at least maintain in the chamber 710 at least some of the bodily fluids that flow down the shaft 757 of the penis 724 or receive bodily fluids that otherwise remain on the shaft. Thus, the portion(s) of the first intermediate portion 708*a* that abut or at least partially surround the penis 724 may minimize leakage of bodily fluids from the chamber 710.

In an embodiment, the first intermediate portion 708*a* may define a cutout 756. The cutout 756 may extend inwardly from (as shown) from the proximal end region 706 or may be a hole proximate the proximal end region 706 that is completely surrounded by the first intermediate portion 708. The cutout 756 is configured to receive the penis 724 such that the first intermediate portion 708*a* partially surrounds (when the cutout 756 extends inwardly from the proximal end region 706) or completely surrounds (when the cutout 756 is a hole) the penis 724. The cutout 756 allows the first intermediate portion 708*a* to be adjacent to or abut more of the penis 724 than if the first intermediate portion 708*a* did not include the cutout 756. As such, the cutout 756 allows the first intermediate portion 708*a* to receive or at least maintain in the chamber 710 more of the bodily fluids that if the first intermediate portion 708*a* did not include the cutout 756.

FIG. 7B is a cross-sectional schematic of the fluid collection assembly 700 being used with a penis 724, according to an embodiment. As shown, the first intermediate portion 708*a* is positioned adjacent to or abuts the penis 724, such as the shaft 757 or the base 758 of the penis 724. When the first intermediate portion 708*a* includes a cutout 756, the penis 724 may be at least partially positioned in the cutout 756. The urethral opening (e.g., glans 760) of the penis 724 is positioned within or adjacent to the distal region 704 such that bodily fluids discharged from the urethral opening may be preferentially received by the distal region 704 and removed from the chamber 710 using the fluid outlet 714. A portion of the second intermediate portion 708*b* may then be positioned adjacent to an opposing side of the shaft 757 of the penis 724 than the first intermediate portion 708*a*. The portion of the second intermediate portion 708*b* that is not adjacent to the shaft 757 of the penis 724 may be positioned against the mons pubis 728 of the patient. As illustrated in FIG. 7B, the second intermediate portion 708*b* may travel a longer distance from the distal region 704 than the first intermediate portion 708*a* and, for this reason, the second intermediate portion 708*b* may exhibit a length that is greater than the first intermediate portion 708*a*. A portion of the first intermediate portion 708*a* (e.g., edges of the first intermediate portion 708*a*) and a portion of the second intermediate portion 708*b* (e.g., edges of the second intermediate portion 708*b*) may be attached together or at least positioned adjacent to each other to minimize bodily fluids leaking between the first and second intermediate portions 708*a*, 708*b*.

Figure 8:
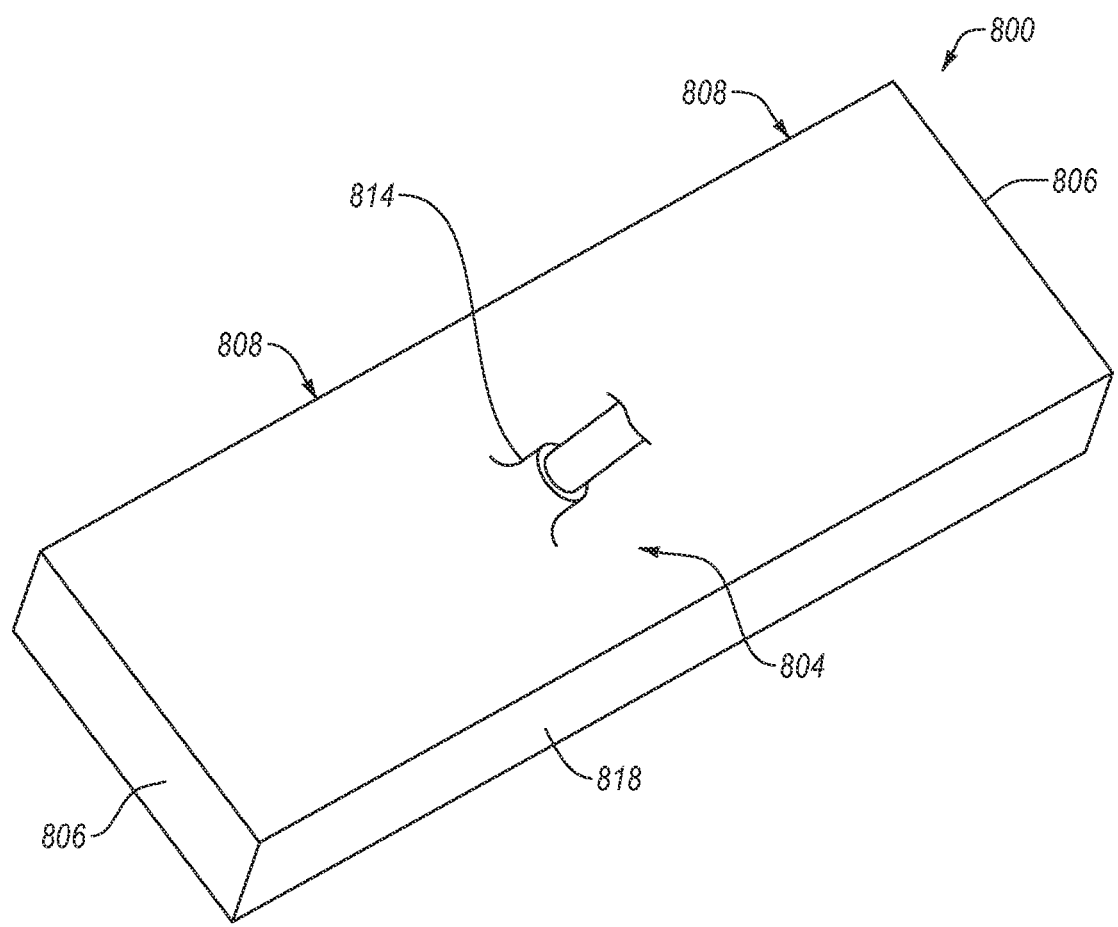
FIG. 8 is an isometric view of a fluid collection assembly that includes a distal region that is not a sump, according to an embodiment.

The fluid collection assemblies illustrated in FIGS. 1A-7B are illustrated as including a distal region that is a sump. However, in some embodiments, the fluid collection assemblies disclosed herein may include a distal region that is not a sump. For example, FIG. 8 is an isometric view of a fluid collection assembly 800 that includes a distal region 804 that is not a sump, according to an embodiment. Except as otherwise disclosed herein, the fluid collection assembly 800 is the same or substantially similar to any of the fluid collection assemblies disclosed herein. For example, the fluid collection assembly 800 may include the distal region 804, at least one proximal end region 806, and at least one intermediate portion 808 extending from the distal region 804 to the proximal end region 806.

As previously discussed, the distal region 804 of the fluid collection assembly 800 is not a sump. Such a distal region 804 may allow the fluid collection assembly 800 to lie flat on a surface or otherwise conform to the shape of a surface. The ability of the fluid collection assembly 800 to lie flat on a surface or otherwise conform to the shape of the surface may allow the fluid collection assembly 800 to be more effectively used with a buried penis. For example, the distal region 804 of the fluid collection assembly 800 may lie flat across the buried penis thereby allowing the urethral opening to be positioned closer to the fluid outlet 814 than if the distal region 804 included a sump. It is noted that a fluid collection assembly may still be used with a buried penis if the distal region thereof is a sump but that the sump may increase the distance between the urethral opening of the buried penis and the fluid outlet.

The at least one intermediate portion 808 of the fluid collection assembly 800 allows the fluid collection assembly 800 to be used with non-buried penises. For example, at least a portion of the lateral edges 818 may be positioned together thereby allowing the intermediate portion 808 in conjunction with the distal region 804 to form a sump-like shape. The non-buried penis may be disposed in the sump-like shape.

It is noted that the fluid outlet 814 may extend outwardly from the rest of the fluid collection assembly 800 when the fluid collection assembly 800 lies flat. Extending the fluid outlet 814 outwardly from the rest of the fluid collection assembly 800 may facilitate attaching the conduit 842 thereto. However, the fluid outlet 814 is too small to form a sump in which the glans of the penis may be positioned therein. Thus, the fluid collection assembly 800 may include a distal region 804 that is not a sump but also include a fluid outlet 814 extending outwardly from the rest of the fluid collection assembly 800.

Figure 9:
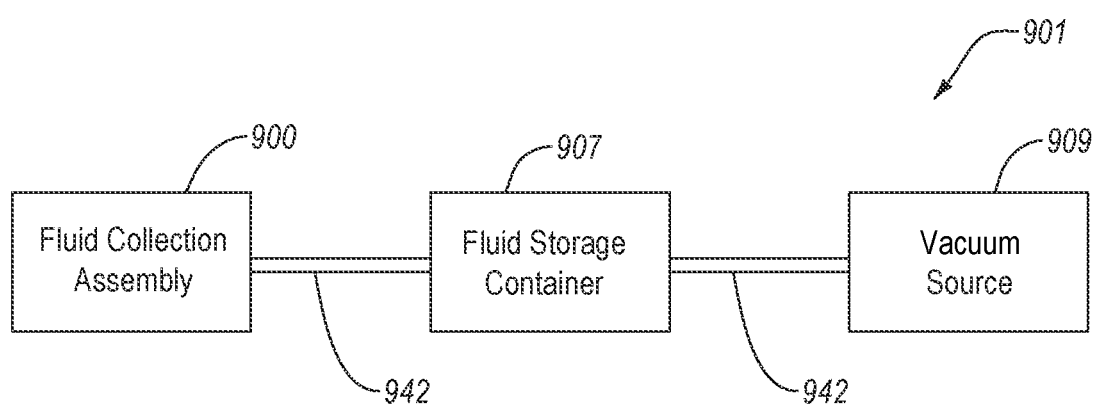
FIG. 9 is a block diagram of a fluid collection system for fluid collection, according to an embodiment.

FIG. 9 is a block diagram of a fluid collection system 901 for fluid collection, according to an embodiment. The fluid collection system 901 includes a fluid collection assembly 900 that is similar or identical to any of the fluid collection assemblies disclosed herein in one or more aspects. The fluid collection system 901 also includes a fluid storage container 907, and a vacuum source 909. The fluid collection assembly 900, the fluid storage container 907, and the vacuum source 909 may be fluidly coupled to each other via one or more conduits 942. For example, fluid collection assembly 900 may be operably coupled to one or more of the fluid storage container 907 or the vacuum source 909 via the conduit 942. Bodily fluids (e.g., urine or other bodily fluids) collected in the fluid collection assembly 900 may be removed from the fluid collection assembly 900 via the conduit 942 which protrudes into the fluid collection assembly 900. For example, an inlet of the conduit 942 may extend into the fluid collection assembly 900, such as to a reservoir therein. The outlet of the conduit 942 may extend into the fluid storage container 907 or the vacuum source 909. Suction force may be introduced into the chamber of the fluid collection assembly 900 via the inlet of the conduit 942 responsive to suction (e.g., vacuum) force applied at the outlet of the conduit 942.

The suction force may be applied to the outlet of the conduit 942 by the vacuum source 909 either directly or indirectly. The suction force may be applied indirectly via the fluid storage container 907. For example, the outlet of the conduit 942 may be disposed within the fluid storage container 907 and an additional conduit 942 may extend from the fluid storage container 907 to the vacuum source 909. Accordingly, the vacuum source 909 may apply suction to the fluid collection assembly 900 via the fluid storage container 907. The suction force may be applied directly via the vacuum source 909. For example, the outlet of the conduit 942 may be disposed within the vacuum source 909. An additional conduit 942 may extend from the vacuum source 909 to a point outside of the fluid collection assembly 900, such as to the fluid storage container 907. In such examples, the vacuum source 909 may be disposed between the fluid collection assembly 900 and the fluid storage container 907.

The fluid storage container 907 is sized and shaped to retain the bodily fluids therein. The fluid storage container 907 may include a bag (e.g., drainage bag), a bottle or cup (e.g., collection jar), or any other enclosed container for storing bodily fluids such as urine. In some examples, the conduit 942 may extend from the fluid collection assembly 900 and attach to the fluid storage container 907 at a first point therein. An additional conduit 942 may attach to the fluid storage container 907 at a second point thereon and may extend and attach to the vacuum source 909. Accordingly, a vacuum (e.g., suction) may be drawn through fluid collection assembly 900 via the fluid storage container 907. Fluid, such as urine, may be drained from the fluid collection assembly 900 using the vacuum source 909.

The vacuum source 909 may include one or more of a manual vacuum pump, and electric vacuum pump, a diaphragm pump, a centrifugal pump, a displacement pump, a magnetically driven pump, a peristaltic pump, or any pump configured to produce a vacuum. The vacuum source 909 may provide a vacuum or suction to remove fluid from the fluid collection assembly 900. In some examples, the vacuum source 909 may be powered by one or more of a power cord (e.g., connected to a power socket), one or more batteries, or even manual power (e.g., a hand operated vacuum pump). In some examples, the vacuum source 909 may be sized and shaped to fit outside of, on, or within the fluid collection assembly 900. For example, the vacuum source 909 may include one or more miniaturized pumps or one or more micro pumps. The vacuum sources 909 disclosed herein may include one or more of a switch, a button, a plug, a remote, or any other device suitable to activate the vacuum source 909.

The fluid collection assemblies disclosed herein are discussed as being used with a penis. For example, the fluid collection assemblies are disclosed as being positioned on, around, or above a penis. However, it is noted that the fluid collection assemblies disclosed herein may collect bodily fluids from anatomy other than a penis. In an embodiment, the fluid collection assemblies disclosed herein may be positioned on, around, or above a female urethral opening (e.g., vaginal) thereby allowing the fluid collection assemblies to remove urine, blood, vagina discharge, or other relevant bodily fluids from the vagina. In an embodiment, the fluid collection assemblies disclosed herein may be positioned on, around, or above a wound thereby allowing the fluid collection assemblies to receive and remove blood, puss, serous fluid, or other relevant bodily fluids from the wound. In an embodiment, the fluid collection assemblies may be disposed on any other anatomical feature of a patient to remove moisture, oil, or other bodily fluids from the anatomical feature, such as a finger of a surgeon.

While various aspects and embodiments have been disclosed herein, other aspects and embodiments are contemplated. The various aspects and embodiments disclosed herein are for purposes of illustration and are not intended to be limiting.

Terms of degree (e.g., "about," "substantially," "generally," etc.) indicate structurally or functionally insignificant variations. In an example, when the term of degree is included with a term indicating quantity, the term of degree is interpreted to mean±10%, ±5%, or ±2% of the term indicating quantity. In an example, when the term of degree is used to modify a shape, the term of degree indicates that the shape being modified by the term of degree has the appearance of the disclosed shape. For instance, the term of degree may be used to indicate that the shape may have rounded corners instead of sharp corners, curved edges instead of straight edges, one or more perforations extending therefrom, is oblong, is the same as the disclosed shape, etc.

What is claimed is:

1. A fluid collection assembly, comprising:
   a distal region;
   at least one proximal end region spaced from the distal region;
   at least one intermediate portion extending from the at least one proximal end region to the distal region;
   at least one length adjusting feature extending from the at least one proximal end region towards the distal region, the at least one length adjusting feature configured to allow a length of the fluid collection assembly to change;
   a fluid impermeable barrier forming at least a portion of the distal region, the at least one proximal end region, and the at least one intermediate portion, the fluid impermeable barrier at least defining a chamber, an opening at the proximal end region, and a fluid outlet; and
   at least one porous material disposed in the chamber, the at least one porous material configured to receive bodily fluids and move the bodily fluids towards an interior of the chamber and the fluid outlet, the at least one porous material including at least one porous material slit adjacent to the at least one length adjusting feature, the at least one porous material including one or more edges adjacent to the proximal end region and adjacent to the at least one porous material slit;
   wherein the fluid impermeable barrier includes at least one inwardly extending portion extending distally into the chamber from an exterior portion of the fluid impermeable barrier, the at least one inwardly extending portion at least partially covering the one or more edges adjacent to the proximal end region and the one or more edges adjacent to the at least one porous material slit.

2. The fluid collection assembly of claim 1, wherein the distal region is a sump.

3. The fluid collection assembly of claim 1, wherein the distal region is not a sump.

4. The fluid collection assembly of claim 1, wherein the distal region defines a fluid reservoir.

5. The fluid collection assembly of claim 1, wherein the distal region includes the fluid outlet.

6. The fluid collection assembly of claim 1, wherein the at least one length adjusting feature includes at least one slit.

7. The fluid collection assembly of claim 1, wherein the at least one length adjusting feature includes a plurality of perforations.

8. The fluid collection assembly of claim 1, further comprising at least one retainer configured to be disposed adjacent to an exterior surface of the fluid impermeable barrier and to maintain a length of the fluid collection assembly.

9. The fluid collection assembly of claim 1, wherein the at least one length adjusting feature includes a single length adjusting feature and the at least one intermediate portion includes a single intermediate portion.

10. The fluid collection assembly of claim 1, wherein the at least one length adjusting feature includes a plurality of length adjusting features and the at least one intermediate portion includes a plurality of intermediate portions between adjacent ones of the plurality of length adjusting features.

11. The fluid collection assembly of claim 10, wherein at least one of the plurality of intermediate portions includes an inner surface that partially overlaps an outer surface another one of the plurality of intermediate portions at or near the distal region when the plurality of intermediate portions are completely flared.

12. The fluid collection assembly of claim 10, wherein an angle between two adjacent lateral edges of a first set of two different intermediate portions is different than an angle between two other adjacent lateral edges of a second set of two different intermediate portions when the plurality of intermediate portions are completely flared.

13. The fluid collection assembly of claim 10, wherein each angle between two adjacent lateral edges of two different intermediate portions is the same when the plurality of intermediate portions are completely flared.

14. The fluid collection assembly of claim 10, wherein the plurality of intermediate portions includes 2 to 5 intermediate portions.

15. The fluid collection assembly of claim 1, wherein the at least one intermediate portion includes an adhesive on an interior surface thereof.

16. The fluid collection assembly of claim 1, wherein the at least one inwardly extending portion of the fluid impermeable barrier at least partially covers the one or more edges adjacent to the proximal end region.

17. The fluid collection assembly of claim 1, wherein the at least one inwardly extending portion of the fluid impermeable barrier at least partially covers the one or more edges adjacent to the at least one length adjusting feature.

18. The fluid collection assembly of claim 1, further comprising at least one conduit extending through the fluid outlet to a location proximate to the proximal end region.

19. The fluid collection assembly of claim 1, wherein the fluid impermeable barrier includes at least one chamber extending portion extending from the at least one inwardly extending portion into the chamber.

20. The fluid collection assembly of claim 2, wherein the at least one porous material extends into and across the sump.

21. The fluid collection assembly of claim 1, wherein the fluid impermeable barrier includes:
   an outer portion abutting at least one first surface of the porous material;
   at least one chamber portion abutting a portion of at least one second surface of the porous material;
   wherein the at least one second surface of is opposite the at least one first surface;
   wherein the one or more edges of the porous material adjacent to the proximal end region extend between the at least one first surface and the at least one second surface; and
   wherein the at least one inwardly extending portion extends between the outer portion and the at least one chamber portion, the at least one inwardly extending portion completely covering the one or more edges adjacent to the proximal end region.

22. A fluid collection system, comprising:
   a fluid storage container configured to hold one or more bodily fluids;
   a fluid collection assembly including:
      a distal region;
      at least one proximal end region spaced from the distal region;
      at least one intermediate portion extending from the at least one proximal end region to the distal region;
      at least one length adjusting feature extending from the at least one proximal end region towards the distal region, the at least one length adjusting feature configured to allow a length of the fluid collection assembly to change;

a fluid impermeable barrier forming at least a portion of the distal region, the at least one proximal end region, and the at least one intermediate portion, the fluid impermeable barrier at least defining a chamber, an opening at the proximal end region, and a fluid outlet; and at least one porous material disposed in the chamber, the at least one porous material configured to receive bodily fluids and move the bodily fluids towards an interior of the chamber and the fluid outlet, the at least one porous material including at least one porous material slit adjacent to the at least one length adjusting feature, the at least one porous material including one or more edges adjacent to the proximal end region and adjacent to the at least one length adjusting feature;

wherein the fluid impermeable barrier includes at least one inwardly extending portion extending distally into the chamber from an exterior portion of the fluid impermeable barrier, the at least one inwardly extending portion at least partially covering the one or more edges adjacent to the proximal end region and the one or more edges adjacent to the at least one porous material slit; and a vacuum source fluidly coupled to one or more of the fluid storage container or the fluid collection assembly via the conduit, the vacuum source configured to draw fluid from the fluid collection assembly via the conduit.

\* \* \* \* \*